(12) United States Patent
Solan et al.

(10) Patent No.: US 7,217,675 B2
(45) Date of Patent: May 15, 2007

(54) CATALYST COMPOSITION

(75) Inventors: Gregory Adam Solan, Leicester (GB); Christopher James Davies, Lancashire (GB)

(73) Assignee: ExxonMobil Chemical Patents Inc., Houston, TX (US)

( * ) Notice: Subject to any disclaimer, the term of this patent is extended or adjusted under 35 U.S.C. 154(b) by 357 days.

(21) Appl. No.: 10/802,514

(22) Filed: Mar. 17, 2004

(65) Prior Publication Data
US 2004/0242893 A1  Dec. 2, 2004

(51) Int. Cl.
C07F 15/00 (2006.01)
C08F 4/44 (2006.01)
B01J 31/00 (2006.01)

(52) U.S. Cl. ............... 502/117; 502/152; 502/165; 502/166; 502/167; 548/101

(58) Field of Classification Search .......... 502/117, 502/152, 165, 166, 167; 548/101
See application file for complete search history.

(56) References Cited

U.S. PATENT DOCUMENTS

| 3,651,065 | A | 3/1972 | Yagi et al. | 260/270 |
| 6,689,848 | B2* | 2/2004 | Nagy et al. | 526/129 |
| 6,809,058 | B2* | 10/2004 | Boffa et al. | 502/167 |
| 2003/0166806 | A1* | 9/2003 | Nagy et al. | 526/172 |
| 2004/0266961 | A1* | 12/2004 | Solan et al. | 526/114 |

FOREIGN PATENT DOCUMENTS

| WO | WO 99/02472 | 1/1999 |
| WO | WO 99/12981 | 3/1999 |
| WO | WO 00/58320 | 5/2000 |
| WO | WO 00/50470 | 8/2000 |
| WO | 00/68280 | 11/2000 |
| WO | WO 01/14391 | 3/2001 |
| WO | WO 01/83571 | 11/2001 |
| WO | 03/076481 | 9/2003 |

OTHER PUBLICATIONS

Weitzer et al., "Low Temperature Stopped-flow Studies in Inorganic Chemistry", Journal of the Chemical Society, Dalton Transactions, 2002, pp. 686-694.

Wang et al., "Late Transition Metal Complexes bearing 2,9-bis(imino)-1,10-phenanthrolinyl Ligands: Synthesis, Characterization and their Ethylene Activity", Journal of Organometallic Chemistry 658 (2002) pp. 62-70.

Kobayashi et al., "Release of free Nucleobases from Oligomers by Copper(II)-Peroxide Adduct", Polyhedron, 19, 2000, pp. 2639-2648.

(Continued)

Primary Examiner—Karl Group
(74) Attorney, Agent, or Firm—Catherine L. Bell

(57) ABSTRACT

This invention relates to transition metal catalyst compounds represented by the formula: $LMX_2$ wherein M is a Group 7 to 11 metal; L is a tridentate or tetradentate neutrally charged ligand that is bonded to M by least three or four nitrogen atoms, and at least one terminal nitrogen atom is part of a pyridinyl ring, a different terminal nitrogen atom is substituted with one $C_3$–$C_{50}$ hydrocarbyl, and one hydrogen atom or two hydrocarbyls; wherein at least one hydrocarbyl is a $C_3$–$C_{50}$ hydrocarbyl, and the central nitrogen atom is bonded to at least three different carbon atoms or two different carbon atoms, and one hydrogen atom; X is independently a monoanionic ligand or both X are joined together to form a bidentate dianionic ligand.

23 Claims, 4 Drawing Sheets

OTHER PUBLICATIONS

Kooistra et al., "Cobalt Chloride Complexes of $N_3$ and $N_4$ Donor Ligands", *Eur. J. Inorg. Chemistry*, 2003, pp. 648-655.

Prokopchuk et al., "Methyl(hydrido)platinum(IV) Complexes with Flexible Tridentate Nitrogen-Donor Ligands", *Organometallics*, vol. 22, pp. 787-796, (2003).

Markies et al., "Synthesis and Structural Studies of Ionic Monoorganopalladium(II) Complexes with Tridentate Nitrogen-Donor Ligands," *Organometallics*, vol. 13, pp. 3244-3258, (1994).

Johnson et al., "Cooper ATRP Catalysts with Quadridentate Amine Ligands: The Effects of Steric and Electronic Tuning on the Polymerization of Methyl Methacrylate," *Macromolecules*, vol. 33, pp. 8618-8628, (2000).

Dey et al., "Crystal Structure and Magnetic Interactions in Nickel(II) Dibridged Complexes Formed by Two Azide Groups or by Both Phenolate Oxygen-Azide, -Thiocyanate,—Carboxylate, or-Cyanate Groups," *Inorganic Chemistry*, vol. 43, pp. 2427-2434, (2004).

Britovsek et al., "Oligomerisation of Ethylene by Bis(imino)pyridyliron and -cobalt Complexes", *Chem. Eur. J.*, vol. 6, No. 12, pp. 2221-2231 (2000).

Britovsek et al., "Bis(imino)pyridyl iron and cobalt complexes: the effect of nitrogen substituents on ethylene oligomerisation and polymerisation," *J. Chem. Soc., Dalton Trans.*, pp. 1639-1644, (2001).

Britovsek et al., "The role of bulky substituents in the Polymerization of ethylene using late transition metal catalysts: a comparative study of nickel and iron catalyst systems," *Inorganica Chimica Acta*, vol. 345, pp. 279-291, (2003).

Small et al., "Iron Based Catalysts with Exceptionally High Activities and Selectivities for Oligomerization of Ethylene to Linear α-Olefins," *J. Am. Chem. Soc.*, vol. 120, pp. 7143-7144, (1998).

B. Elvers, et al., Ed. Ullmann's Encyclopedia of Industrial Chemistry, vol. A13, VCH Verlagsgesellschaft mbH, Weinheim, pp. 243-247 and 275-276, (1989).

* cited by examiner

Schulz-Flory distribution: ln Mol% of each fraction vs. carbon number

Oligomer distribution: yield of oligomer fraction vs. carbon number

CATALYST COMPOSITION

FIELD OF THE INVENTION

This invention relates to late transition metal catalysts for olefin oligomerizations or polymerization and to methods for making and using these catalysts.

BACKGROUND OF THE INVENTION

Alpha-olefins, especially those containing 6 to 20 carbon atoms, are important items of commerce. They are used as intermediates in the manufacture of detergents, as monomers (especially in linear low-density polyethylene), and as intermediates for many other types of products. Consequently, improved methods of making these compounds are desired. Especially desired, is a process capable of making a range of linear α-olefins such as 1-butene and 1-hexene.

Most commercially produced alpha-olefins are made by the oligomerization of ethylene, catalyzed by various types of compounds, see for instance B. Elvers, et al., Ed. Ullmann's Encyclopedia of Industrial Chemistry, Vol. A13, VCH Verlagsgesellschaft mbH, Weinheim, 1989, p. 243–247 and 275–276, and B. Cornils, et al., Ed., Applied Homogeneous Catalysis with Organometallic Compounds, A Comprehensive Handbook, Vol. 1, VCH Verlagsgesellschaft mbH, Weinheim, 1996, p. 245–258. The major types of commercially used catalysts are alkylaluminum compounds, certain nickel-phosphine complexes, and a titanium halide with a Lewis acid. In all of these processes, significant amounts of branched internal olefins and diolefins are produced. Since in most instances these are undesirable and often difficult to separate, these byproducts are avoided commercially.

More recently, some iron complexes bearing tridentate chelating bis(imino)pyridine ligands have been reported, produce oligomers when activated (B. L. Small and M. Brookhart, J. Am. Chem. Soc. 1998, 120, 7143; M. Brookhart and B. L. Small, PCT Int. Appl. WO9902472, 1999 (DuPont)). Imino-bipyridine based iron complexes when activated produce low molecular weight oligomers (G. J. P. Britovsek, S. D. Baugh, O. Hoarau, V. C. Gibson, D. F. Wass, A. J. P. White, D. J. Williams, Inorg. Chim. Acta 2003, 345, 279. Bis(hydrazone)pyridine complexes of iron afford mixtures of low molecular weight polymer and oligomers (G. J. P. Britovsek, V. C. Gibson, B. S. Kimberley, S. Mastroianni, C. Redshaw, G. A. Solan, A. J. P. White, D. J. Williams, J. Chem. Soc., Dalton Trans. 2001, 1639; M. O. Kristen, A. Gonioukh, D. Lilge, S. Lehmann, B. Bildstein, C. Amort, M. Malaun PCT Int. Appl. WO0114391, 2001 (BASF); L. S. Moody, P. B. MacKenzie, C. M. Killian, G. G. Lavoie, J. A. Ponasik Jr., T. W. Smith, J. C. Pearson, A. G. M. Barrett, G. W. Coates, PCT Int. Appl. WO0183571, 2001 (Eastman); L. S. Moody, P. B. MacKenzie, C. M. Killian, G. G. Lavoie, J. A. Ponasik Jr., A. G. M. Barrett, T. W. Smith, J. C. Pearson, PCT Int. Appl. WO0050470, 2000 (Eastman)). Iron based oligomerization catalysts have been reported in G. J. P. Britovsek, S. Mastroianni, G. A. Solan, S. P. D. Baugh, C. Redshaw, V. C. Gibson, A. J. P. White, D. J. Williams and M. Elsegood, Chem. Eur. J., 2000, 6, 221, and in G. J. Britovsek, B. Dorer, V. C. Gibson, B. S. Kimberley and G. A. Solan, WO9912981, 1999 (BP Chemicals Ltd.).

Hence new oligomerization catalysts are of great interest in the industry because they offer many new opportunities for providing new processes and products in a cheaper and more efficient manner. The following invention relates to new oligomerization technology based upon new late transition metal catalyst compounds.

SUMMARY OF THE INVENTION

The present invention is directed toward Group 7, 8, 9, 10, or 11 transition metal compounds containing neutral tridentate or tetradentate nitrogen based ligands and an activator that are useful for oligomerizing or polymerizing olefins, particularly α-olefins, or other unsaturated monomers. For purposes of this disclosure, "α-olefins" includes ethylene.

Catalyst components of this invention comprise transition metal compounds (precatalyst or catalyst precursor) of formula: $LMX_2$ or $(LMX_2)_2$ wherein each M is, independently, a Group 7, 8, 9, 10 or 11 metal, preferably a Group 7, 8, 9, or 10 metal; L is, independently, a tridentate or tetradentate neutrally charged ligand that is bonded to M by three or four nitrogen atoms, where at least one of the nitrogen atoms is a central nitrogen atom, and at least two of the nitrogen atoms are terminal nitrogen atoms, and at least one terminal nitrogen atom is part of a pyridinyl ring, a different terminal nitrogen atom is substituted with one $C_3$–$C_{50}$ hydrocarbyl and one hydrogen atom or two hydrocarbyls wherein at least one hydrocarbyl is a $C_3$–$C_{50}$ hydrocarbyl, and the central nitrogen atom is bonded to three different carbon atoms or two different carbon atoms, and one hydrogen atom; X is, independently a monoanionic ligand or, two X are joined together to form a bidentate dianionic ligand. "Independently" means that when two or more of the substituents are present, they may differ one from the other.

Accordingly, in one aspect of the present invention, a catalyst precursor comprises a compound represented by the formula: $LMX_2$ or the formula $(LMX_2)_2$ wherein each M is, independently, a Group 7, 8, 9, 10 or 11 transition metal; L is, independently, a tridentate or tetradentate neutrally charged ligand that is bonded to M by at least three nitrogen atoms; at least one of the nitrogen atoms is a central nitrogen atom; at least two of the nitrogen atoms are terminal nitrogen atoms; at least one terminal nitrogen atom is part of a pyridinyl ring; at least one other terminal nitrogen atom is substituted with at least one $C_3$–$C_{50}$ hydrocarbyl; the central nitrogen atom is bonded to at least two different carbon atoms; and X is, independently, an anionic monodentate ligand or two X may join together to form a bidentate dianionic ligand.

This invention further relates to compositions or transition metal compounds represented by formula 1:

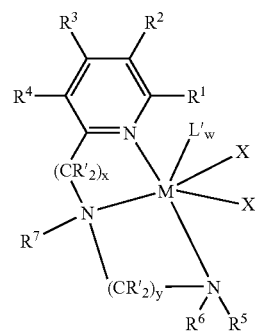

-continued formula 2:

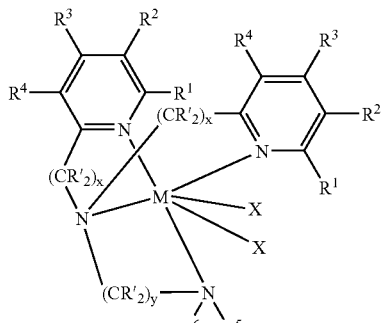

formula 3:

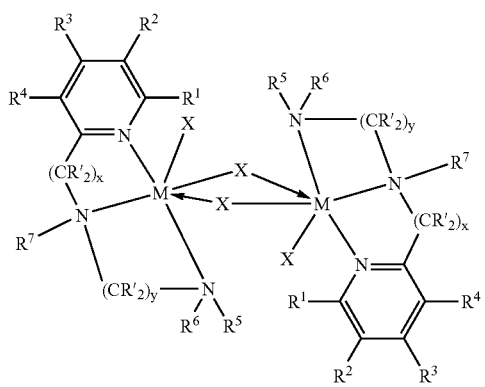

or formula 4:

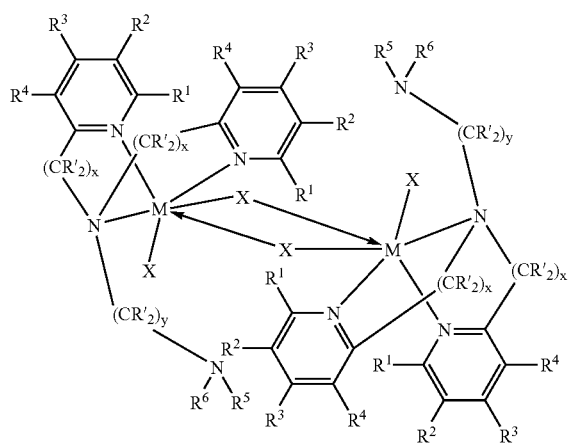

wherein each M is, independently, a group 7, 8, 9, 10, or 11 transition metal; N is nitrogen; C is carbon; X is, independently, an anionic monodentate ligand, or two X groups together form a bidentate dianionic ligand; R' is, independently, a hydrogen, a hydrocarbyl, a substituted hydrocarbyl, a halocarbyl, or a substituted halocarbyl; or independently, two R' groups on the same carbon join to form a cyclic or polycyclic ring structure; when x is 2, 3, or 4, and/or when y is 2, 3, or 4, two or more R' groups on adjacent carbon atoms may join to form a cyclic or polycyclic ring structure; x is, independently, 1, 2, 3 or 4; y is, independently, 1, 2, 3 or 4; $R^1$, $R^2$, $R^3$ and $R^4$ or, independently, a hydrogen, a hydrocarbyl, a substituted a hydrocarbyl, a halocarbyl, or a substituted halocarbyl, or independently, two adjacent $R^1$, $R^2$, $R^3$ or $R^4$ join together to form a cyclic or polycyclic ring structure; $R^5$ is, independently, a hydrogen, hydrocarbyl or halocarbyl; $R^6$ is, independently, a $C_3$ to $C_{50}$ hydrocarbyl or a $C_3$ to $C_{50}$ halocarbyl; $R^7$ is, independently, hydrogen, a hydrocarbyl, a substituted hydrocarbyl, a halocarbyl, or a substituted halocarbyl; $R^7$ may be bonded to M through the heteroatom of a substituted hydrocarbyl or a substituted halocarbyl; L' is a neutral ligand bonded to M; and w is 0 or 1.

Accordingly, in another aspect of the present invention is a catalyst precursor represented by formula 1, 2, 3, and/or 4, wherein M is a Group 7, 8, 9, 10, or 11 transition metal; N is nitrogen; C is carbon; X is, independently, an anionic monodentate ligand, or both X groups together form a bidentate dianionic ligand; R' is, independently, a hydrogen, a hydrocarbyl, a substituted hydrocarbyl, a halocarbyl, a substituted halocarbyl, a cyclic ring comprising two R' groups on the same carbon, a polycyclic ring comprising two R' groups on the same carbon, a cyclic ring comprising two or more R' groups on adjacent carbons, or a polycyclic ring comprising two or more R' groups on adjacent carbons; x is 1, 2, 3, or 4; y is 1, 2, 3, or 4, $R^1$, $R^2$, $R^3$ or $R^4$ is, independently, a hydrogen, a hydrocarbyl, a substituted a hydrocarbyl, a halocarbyl, a substituted halocarbyl, a cyclic ring structure comprising two adjacent $R^1$, $R^2$, $R^3$ or $R^4$, or a polycyclic ring structure comprising two adjacent $R^1$, $R^2$, $R^3$ or $R^4$; $R^5$ is a hydrogen, a hydrocarbyl or a halocarbyl; $R^6$ is a $C_3$ to $C_{50}$ hydrocarbyl or a $C_3$ to $C_{50}$ halocarbyl; $R^7$ is a hydrogen, a hydrocarbyl, a substituted hydrocarbyl, a halocarbyl, a substituted halocarbyl; substituted hydrocarbyl comprising a heteroatom, wherein the heteroatom is bonded to M, or a substituted halocarbyl comprising a heteroatom, wherein the heteroatom is bonded to M; L' is a neutral ligand bonded to M; and w is 0 or 1.

This invention further relates to a catalyst system comprising any one of the above catalyst precursors and an activator, and a process to oligomerize and/or polymerize an unsaturated monomer using the catalyst system described herein.

BRIEF DESCRIPTION OF THE DRAWINGS

FIG. 1 represents the molecular structure of 3a.
FIG. 3 represents the molecular structure of 4a.
FIG. 5 represents the molecular structure of 7a.

DEFINITIONS

Figure 1:
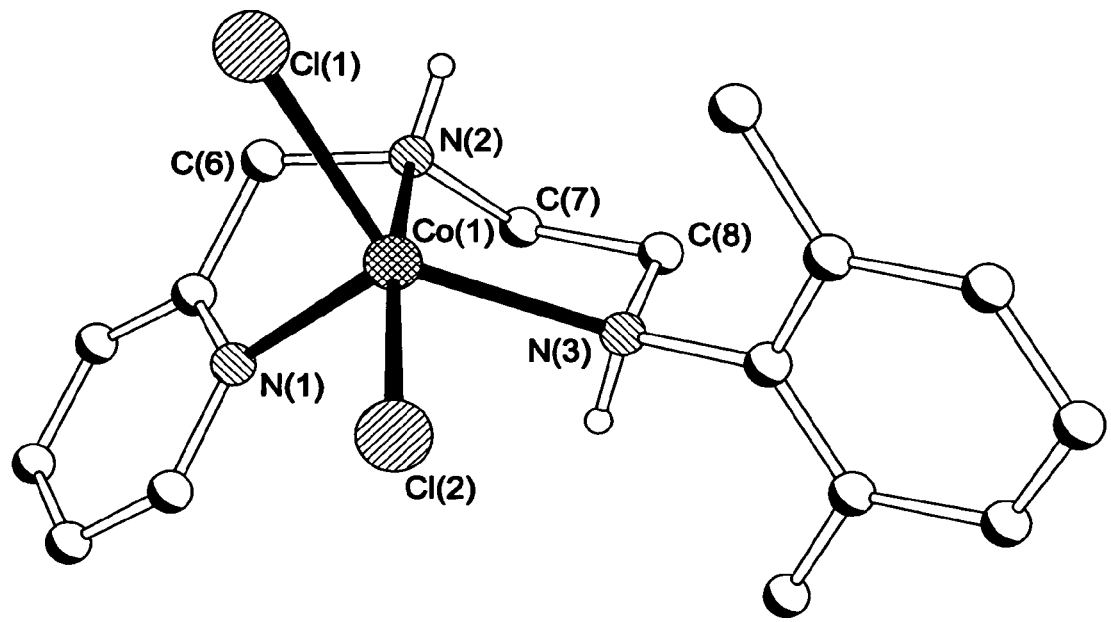

As used herein, the new numbering scheme for the Periodic Table Groups are used as in Chemical and Engineering News, 63(5), 27 (1985).

When a polymer is referred to as "comprising an olefin", the olefin present in the polymer is the polymerized form of the olefin. Likewise when catalyst components are described as comprising neutral stable forms of the components, it is well understood by one of ordinary skill in the art, that the ionic form of the component is the form that reacts with the monomers to produce polymers. In the description herein the transition metal catalyst compound may be described as a catalyst precursor, a pre-catalyst compound or a catalyst compound, and these terms are used interchangeably. A catalyst system is a combination of a transition metal catalyst compound and an activator. An activator is also interchangeably referred to as a cocatalyst.

The term "hydrocarbyl radical" is sometimes used interchangeably with "hydrocarbyl," and encompasses $C_1$–$C_{50}$ radicals. These radicals can be linear, branched, or cyclic (including polycyclic). These radicals can be saturated, partially unsaturated or fully unsaturated, and when cyclic, may be aromatic or non-aromatic.

In describing a ligand, a terminal nitrogen atom is a nitrogen atom that is indirectly bonded to only one other nitrogen atom. A central nitrogen atom is a nitrogen atom that is indirectly bonded to two or more other nitrogen atoms. An example is illustrated below:

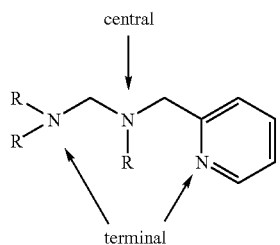

Substituted hydrocarbyl radicals are radicals in which at least one hydrogen atom has been replaced with a heteroatom or with at least one functional group such as $NR''_2$, $OR''$, $PR''_2$, $SR''$, $BR''_2$, $SiR''_3$, $GeR''_3$ and the like or where at least one non-hydrocarbon atom or group has been inserted within the hydrocarbyl radical, such as O, S, $NR''$, $PR''$, $BR''$, $SiR''_2$, $GeR''_2$, and the like, where $R''$ is independently a hydrocarbyl or halocarbyl radical. The functional group can be an organometalloid radical.

Halocarbyl radicals are radicals in which one or more hydrocarbyl hydrogen atoms have been substituted with at least one halogen or halogen-containing group (e.g. F, Cl, Br, I).

Substituted halocarbyl radicals are radicals in which at least one hydrocarbyl hydrogen or halogen atom has been substituted with at least one functional group such as $NR''_2$, $OR''$, $PR''_2$, $SR''$, $BR''_2$, $SiR'_3$, $GeR''_3$ and the like, or where at least one non-carbon atom or group has been inserted within the halocarbyl radical such as O, S, $NR''$, $PR''$, $BR''$, $SiR''_2$, $GeR''_2$, and the like where $R''$ is independently a hydrocarbyl or halocarbyl radical provided that at least one halogen atom remains on the original halocarbyl radical. The functional group can be an organometalloid radical.

In some embodiments, the hydrocarbyl radical is independently selected from methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, ethenyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, or triacontynyl isomers.

For this disclosure, when a radical is listed it indicates that radical type and all other radicals formed when that radical type is subjected to the substitutions defined above. Alkyl, alkenyl and alkynyl radicals listed include all isomers including where appropriate cyclic isomers. For example, butyl includes n-butyl, 2-methylpropyl, 1-methylpropyl, tert-butyl, and cyclobutyl (and analogous substituted-cyclopropyls); pentyl includes n-pentyl, cyclopentyl, 1-methylbutyl, 2-methylbutyl, 3-methylbutyl, 1-ethylpropyl, and neopentyl (and analogous substituted cyclobutyls and cyclopropyls); butenyl includes E and Z forms of 1-butenyl, 2-butenyl, 3-butenyl, 1-methyl-1-propenyl, 1-methyl-2-propenyl, 2-methyl-1-propenyl and 2-methyl-2-propenyl (and cyclobutenyls and cyclopropenyls).

Cyclic compounds having substitutions include all isomer forms, for example, methylphenyl would include ortho-methylphenyl, meta-methylphenyl and para-methylphenyl; dimethylphenyl would include 2,3-dimethylphenyl, 2,4-dimethylphenyl, 2,5-dimethylphenyl, 2,6-diphenylmethyl, 3,4-dimethylphenyl, and 3,5-dimethylphenyl.

The term oligomer refers to compositions having 2–75 mer units and the term polymer refers to compositions having 76 or more mer units. A "mer" is defined as a unit of an oligomer or polymer that originally corresponded to the olefin(s) used in the oligomerization or polymerization reaction. For example, the mer of polyethylene would be ethylene.

Anionic monodentate ligands, also called abstractable ligands, are ligands that are removed from the catalyst precursor to activate it. They are sometimes assigned the label X in this disclosure. X is independently a hydride radical, hydrocarbyl radical, or hydrocarbyl-substituted organometalloid radical; or two X's are connected and form a 3-to-50-atom metallacycle ring. Specifically, this metallacycle ring may take the form of a bidentate dianionic ligand.

When Lewis-acid activators such as methylalumoxane, aluminum alkyls, alkylaluminum alkoxides or alkylaluminum halides that are capable of donating an X ligand, to the transition metal component are used, or when an ionic activator is capable of extracting X, one or more X, which may optionally be bridged to one another, may additionally be independently selected from a halogen, alkoxide, aryloxide, amide, phosphide or other anionic ligand, provided that the resulting activated catalyst contains as least one M-H or M-C connection in which an olefin can insert.

When the pre-catalysts of this invention are drawn as dimeric species, two X may be independently a monoanionic bridging ligand that is bonded to each M (e.g. —X).

In some structures, the ligand-metal connection is drawn with an arrow indicating that the electrons originally came from the ligand. This connection may also be shown by drawing a solid or dashed line. These depictions are interchangeable.

Alicyclic rings are aliphatic radicals that have a ring or cyclic structure in which the ring portion may be saturated or unsaturated, but in which the ring portion may not be aromatic. "Alicyclic," as defined in this document, is a subset of "hydrocarbyl."

DETAILED DESCRIPTION OF THE INVENTION

This invention further relates to compositions or transition metal compounds represented by formula 1:

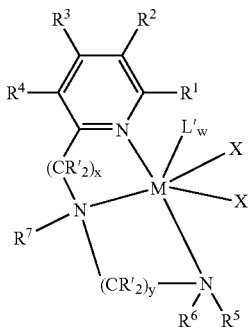

or formula 2:

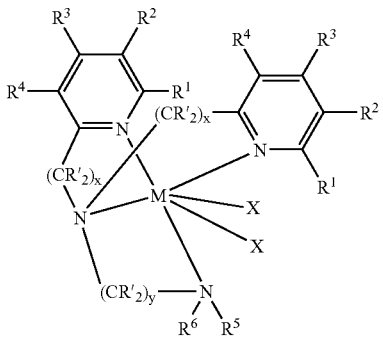

or formula 3:

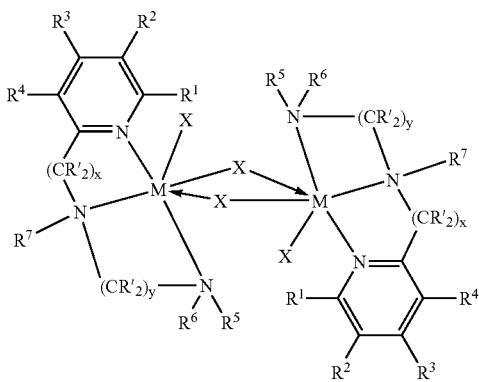

or formula 4:

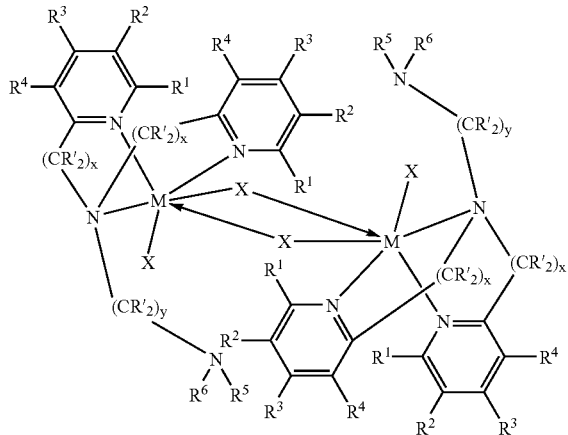

wherein
each M is, independently, a group 7, 8, 9, 10, or 11 transition metal, preferably a group 7, 8, 9 or 10 transition metal, preferably nickel, cobalt, iron or manganese;

N is nitrogen;
C is carbon;
each X is, independently, a hydride, hydrocarbyl, substituted hydrocarbyl, halocarbyl, substituted halocarbyl, or both X groups together are a hydrocarbdiyl, halocarbdiyl, substituted hydrocarbdiyl, or substituted halocarbdiyl;
additionally, X may independently be selected from halogens, alkoxide, aryloxide, amide, phosphide, or other anionic ligands when Lewis-acid activators (such as methylalumoxane, aluminum alkyls, alkylaluminum alkoxides) or alkylaluminum halides (capable of donating a hydride, hydrocarbyl, substituted hydrocarbyl, halocarbyl or substituted halocarbyl X ligand to the transition metal component) are used, or when an ionic activator is capable of extracting X, provided that the resulting activated catalyst contains as least one M—H or M—C bond into which an olefin can insert (one or more X may optionally bridge to one another, as well);
each R' is, independently, a hydrogen, or a hydrocarbyl, a substituted hydrocarbyl, a halocarbyl, or a substituted halocarbyl, preferably, a $C_1$ to $C_{30}$ hydrocarbyl, a $C_1$ to $C_{30}$ substituted hydrocarbyl, a $C_1$ to $C_{30}$ halocarbyl, or a $C_1$ to $C_{30}$ substituted halocarbyl, more preferably a $C_1$ to $C_{10}$ hydrocarbyl, a $C_1$ to $C_{10}$ substituted hydrocarbyl, a $C_1$ to $C_{10}$ halocarbyl, or a $C_1$ to $C_{10}$ substituted halocarbyl;
independently, two R' groups on the same carbon may join to form a $C_3$ to $C_{61}$ cyclic or polycyclic ring structure; when x is 2, 3, or 4, and/or when y is 2, 3, or 4, two or more R' groups on adjacent carbon atoms may join to form a $C_4$ to $C_{62}$ cyclic or polycyclic ring structure;
x is, independently, 1, 2, 3 or 4, preferably, x is 1;
y is, independently, 1, 2, 3 or 4, preferably, y is 2;
each $R^1$, $R^2$, $R^3$ and $R^4$ is, independently, a hydrogen, or a hydrocarbyl, a substituted hydrocarbyl, a halocarbyl, or a substituted halocarbyl, preferably, a $C_1$ to $C_{30}$ hydrocarbyl, a $C_1$ to $C_{30}$ substituted hydrocarbyl, a $C_1$ to $C_{30}$ halocarbyl, or a $C_1$ to $C_{30}$ substituted halocarbyl, more preferably a $C_1$ to $C_{20}$ hydrocarbyl, a $C_1$ to $C_{20}$ substituted hydrocarbyl, a $C_1$ to $C_{20}$ halocarbyl, or a $C_1$ to $C_{20}$ substituted halocarbyl, or independently, one or more adjacent $R^1$, $R^2$, $R^3$, $R^4$ may join to form a cyclic or polycyclic ring structure; $R^1$ is preferably selected from the group consisting of methyl, ethyl, and all linear and cyclic isomers of propyl, butyl, pentyl, hexyl, heptyl, octyl, nonyl, decyl, undecyl, dodecyl, phenyl, dimethylphenyl, diethylphenyl, dipropylphenyl, naphthyl, anthracenyl, and other substituents; $R^1$ is even more preferably, methyl, ethyl, isopropyl, tert-butyl, neopentyl, cyclohexyl, phenyl, 2,6-dimethylphenyl, 2,6-diisopropylphenyl, 2,5-di-tert-butylphenyl, naphthyl, anthracenyl, adamantyl, and norbornyl;
each $R^5$ is, independently, a hydrogen, or a hydrocarbyl, or a halocarbyl, preferably a $C_1$ to $C_{30}$ hydrocarbyl, or a $C_1$ to $C_{30}$ halocarbyl, more preferably a $C_1$ to $C_{10}$ hydrocarbyl, or a $C_1$ to $C_{10}$ halocarbyl;
each $R^6$ is, independently, a $C_3$ to $C_{50}$ hydrocarbyl, or a $C_3$ to $C_{50}$ halocarbyl, preferably a $C_3$ to $C_{30}$ hydrocarbyl, or a $C_3$ to $C_{30}$ halocarbyl, more preferably a $C_3$ to $C_{20}$ hydrocarbyl, or a $C_3$ to $C_{20}$ halocarbyl;
each $R^7$ is, independently, a hydrogen, or a hydrocarbyl, a substituted hydrocarbyl, a halocarbyl, or a substituted halocarbyl, preferably a $C_1$ to $C_{30}$ hydrocarbyl, a $C_1$ to $C_{30}$ substituted hydrocarbyl, a $C_1$ to $C_{30}$ halocarbyl or a $C_1$ to $C_{30}$ substituted halocarbyl, more preferably a $C_1$ to $C_{10}$ hydrocarbyl, a $C_1$ to $C_{10}$ substituted hydrocarbyl, a $C_1$ to $C_{10}$ halocarbyl or a $C_1$ to $C_{10}$ substituted halocarbyl;

optionally R⁷ may be bound to M through the heteroatom of a substituted hydrocarbyl or a substituted halocarbyl;

L' is a neutral ligand bonded to M and includes molecules such as but not limited to diethyl ether, tetrahydrofuran, dimethylaniline, trimethylamine, tributylamine, trimethylphosphine, triphenylphosphine lithium chloride, ethylene, propylene, butene, octene, styrene, and the like; and w is 0 or 1 and indicates the absence or presence of L'.

In a preferred embodiment the halocarbyls are fluorocarbyls and the substituted halocarbyls are substituted fluorocarbyls.

In another preferred embodiment, this invention further relates to compositions represented by the formula 5:

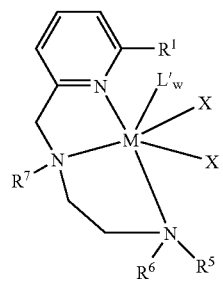

or formula 6:

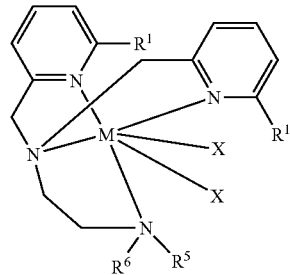

or formula 7:

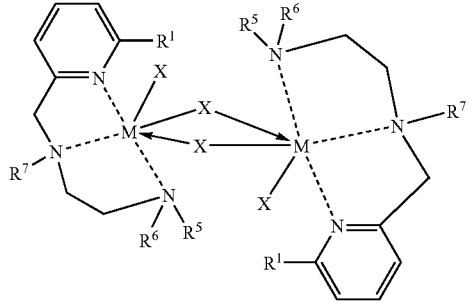

or formula 8:

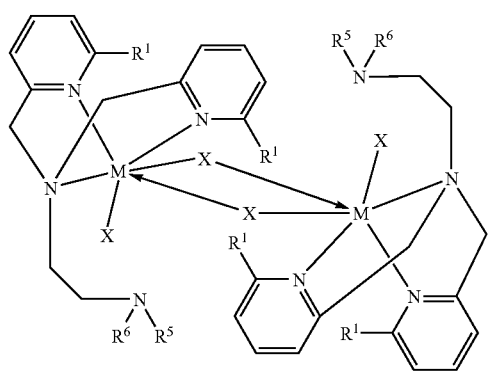

wherein
M, N, R¹, R⁵, R⁶, R⁷, X, L' and w are as previously defined.

To illustrate members of the transition metal catalyst compounds useful in this invention, select any combination of the species listed in Table 1.

| R⁶ | R', R¹, R², R³, R⁴, R⁵, R⁷ | X | M | L' |
|---|---|---|---|---|
| propyl | hydrogen | chloride | cobalt | diethyl ether |
| butyl | methyl | bromide | manganese | tetrahydrofuran |
| pentyl | ethyl | iodide | iron | furan |
| hexyl | propyl | methyl | nickel | thiofuran |
| heptyl | butyl | ethyl | copper | chromane |
| octyl | pentyl | propyl | technetium | isochromane |
| nonyl | hexyl | butyl | rhenium | thiochromane |
| decyl | heptyl | pentyl | ruthenium | thioisochromane |
| undecyl | octyl | hexyl | osmium | quinuclidine |
| dodecyl | nonyl | heptyl | rhodium | benzofuran |
| tridecyl | decyl | octyl | iridium | chromene |
| tetradecyl | undecyl | nonyl | palladium | isobenzofuran |
| octacosyl | dodecyl | decyl | platinum | isoquinoline |
| nonacosyl | tridecyl | undecyl | silver | oxazole |
| triacontyl | tetradecyl | dodecyl | gold | phenanthridine |
| cyclohexyl | octacosyl | tridecyl | | pyran |
| cyclopentyl | nonacosyl | tetradecyl | | pyridine |
| cycloheptyl | triacontyl | pentadecyl | | quinoline |
| cyclooctyl | cyclohexyl | hexadecyl | | selenophene |
| cyclodecyl | cyclopentyl | heptadecyl | | thiophene |
| cyclododecyl | cycloheptyl | octadecyl | | trimethylamine |
| naphthyl | cyclooctyl | nonadecyl | | triethylamine |
| phenyl | cyclodecyl | eicosyl | | tributylamine |
| tolyl | cyclododecyl | heneicosyl | | dimethylaniline |
| benzyl | naphthyl | docosyl | | trimethylphosphine |
| phenethyl | phenyl | tricosyl | | triphenylphosphine |

| | | -continued | |
|---|---|---|---|
| dimethylphenyl | tolyl | tetracosyl | ethylene |
| trimethylphenyl | benzyl | pentacosyl | propylene |
| methylphenyl | phenethyl | hexacosyl | butene |
| ethylphenyl | dimethylphenyl | heptacosyl | hexene |
| diethylphenyl | diethylphenyl | octacosyl | octene |
| triethylphenyl | anthracenyl | nonacosyl | cyclohexene |
| propylphenyl | adamantyl | triacontyl | vinylcyclohexene |
| dipropylphenyl | norbornyl | hydride | benzene |
| tripropylphenyl | | phenyl | styrene |
| methylethylphenyl | | benzyl | methylstyrene |
| dibutylphenyl | | phenethyl | lithium chloride |
| butylphenyl | | tolyl | ammonium chloride |
| | | methoxy | |
| | | ethoxy | |
| | | propoxy | |
| | | butoxy | |
| | | dimethylamido | |
| | | diethylamido | |
| | | methylethylamido | |
| | | phenoxy | |
| | | benzoxy | |
| | | allyl | |

| Both X joined |
|---|
| methylidene |
| ethylidene |
| propylidene |
| tetramethylene |
| pentamethylene |
| hexamethylene |
| butadiene |
| methylbutadiene |
| dimethylbutadiene |
| pentadiene |
| methylpentadiene |
| dimethylpentadiene |
| hexadiene |
| methylhexadiene |
| dimethylhexadiene |

Preferred transition metal catalyst compounds include:
[N-2,6-dimethylphenyl-2-aminoethyl)(2-picolyl)amine]cobalt dichloride,
[N-2,6-dimethylphenyl-2-aminoethyl)(2-picolyl)amine]iron dichloride,
[N-2,6-dimethylphenyl-2-aminoethyl)(2-picolyl)amine] nickel dichloride,
[N-2,6-dimethylphenyl-2-aminoethyl)(2-picolyl)amine] copper dichloride,
[N-2,4-dimethylphenyl-2-aminoethyl)(2-picolyl)amine]cobalt dichloride,
[N-2,4-dimethylphenyl-2-aminoethyl)(2-picolyl)amine]iron dichloride,
[N-2,4-dimethylphenyl-2-aminoethyl)(2-picolyl)amine] nickel dichloride,
[N-2,4-dimethylphenyl-2-aminoethyl)(2-picolyl)amine] copper dichloride,
[N-2,4,6-trimethylphenyl-2-aminoethyl)(2-picolyl)amine] cobalt dichloride,
[N-2,4,6-trimethylphenyl-2-aminoethyl)(2-picolyl)amine] iron dichloride,
[N-2,4,6-trimethylphenyl-2-aminoethyl)(2-picolyl)amine] nickel dichloride,
[N-2,4,6-trimethylphenyl-2-aminoethyl)(2-picolyl)amine] copper dichloride,
[N-2,6-diisopropylphenyl-2-aminoethyl)(2-picolyl)amine] cobalt dichloride,
[N-2,6-diisopropylphenyl-2-aminoethyl)(2-picolyl)amine] iron dichloride,
[N-2,6-diisopropylphenyl-2-aminoethyl)(2-picolyl)amine] nickel dichloride,
[N-2,6-diisopropylphenyl-2-aminoethyl)(2-picolyl)amine] copper dichloride,
[N-2,4,6-triisopropylphenyl-2-aminoethyl)(2-picolyl) amine]cobalt dichloride,
[N-2,4,6-triisopropylphenyl-2-aminoethyl)(2-picolyl) amine]iron dichloride,
[N-2,4,6-triisopropylphenyl-2-aminoethyl)(2-picolyl) amine]nickel dichloride,
[N-2,4,6-triisopropylphenyl-2-aminoethyl)(2-picolyl) amine]copper dichloride,
[N-2,6-dimethylphenyl-2-aminopropyl)(2-picolyl)amine] cobalt dichloride,
[N-2,6-dimethylphenyl-2-aminopropyl)(2-picolyl)amine] iron dichloride,
[N-2,6-dimethylphenyl-2-aminopropyl)(2-picolyl)amine] nickel dichloride,
[N-2,6-dimethylphenyl-2-aminopropyl)(2-picolyl)amine] copper dichloride,
[N-2,4-dimethylphenyl-2-aminopropyl)(2-picolyl)amine] cobalt dichloride,
[N-2,4-dimethylphenyl-2-aminopropyl)(2-picolyl)amine] iron dichloride,
[N-2,4-dimethylphenyl-2-aminopropyl)(2-picolyl)amine] nickel dichloride,
[N-2,4-dimethylphenyl-2-aminopropyl)(2-picolyl)amine] copper dichloride,

[N-2,4,6-trimethylphenyl-2-aminopropyl)(2-picolyl)amine] cobalt dichloride,
[N-2,4,6-trimethylphenyl-2-aminopropyl)(2-picolyl)amine] iron dichloride,
[N-2,4,6-trimethylphenyl-2-aminopropyl)(2-picolyl)amine] nickel dichloride,
[N-2,4,6-trimethylphenyl-2-aminopropyl)(2-picolyl)amine] copper dichloride,
[N-2,6-diisopropylphenyl-2-aminopropyl)(2-picolyl)amine] cobalt dichloride,
[N-2,6-diisopropylphenyl-2-aminopropyl)(2-picolyl)amine] iron dichloride,
[N-2,6-diisopropylphenyl-2-aminopropyl)(2-picolyl)amine] nickel dichloride,
[N-2,6-diisopropylphenyl-2-aminopropyl)(2-picolyl)amine] copper dichloride,
[N-2,4,6-triisopropylphenyl-2-aminopropyl)(2-picolyl)amine]cobalt dichloride,
[N-2,4,6-triisopropylphenyl-2-aminopropyl)(2-picolyl)amine]iron dichloride,
[N-2,4,6-triisopropylphenyl-2-aminopropyl)(2-picolyl)amine]nickel dichloride,
[N-2,4,6-triisopropylphenyl-2-aminopropyl)(2-picolyl)amine]copper dichloride,
[N-2-methylphenyl-2-aminoethyl)(2-picolyl)amine]cobalt dichloride,
[N-2-methylphenyl-2-aminoethyl)(2-picolyl)amine]iron dichloride,
[N-2-methylphenyl-2-aminoethyl)(2-picolyl)amine]nickel dichloride,
[N-2-methylphenyl-2-aminoethyl)(2-picolyl)amine]copper dichloride,
[N-2-isopropylphenyl-2-aminoethyl)(2-picolyl)amine]cobalt dichloride,
[N-2-isopropylphenyl-2-aminoethyl)(2-picolyl)amine]iron dichloride,
[N-2-isopropylphenyl-2-aminoethyl)(2-picolyl)amine] nickel dichloride,
[N-2-isopropylphenyl-2-aminoethyl)(2-picolyl)amine]copper dichloride,
[N-2,6-dimethylphenyl-N-(6-methylpyrindi-2-ylmethyl)ethane-1,2-diamine]cobalt dichloride,
[N-2,6-dimethylphenyl-N-(6-methylpyrindi-2-ylmethyl)ethane-1,2-diamine]iron dichloride,
[N-2,6-dimethylphenyl-N-(6-methylpyrindi-2-ylmethyl)ethane-1,2-diamine]nickel dichloride,
[N-2,6-dimethylphenyl-N-(6-methylpyrindi-2-ylmethyl)ethane-1,2-diamine]copper dichloride,
[N-2,4-dimethylphenyl-N-(6-methylpyrindi-2-ylmethyl)ethane-1,2-diamine]cobalt dichloride,
[N-2,4-dimethylphenyl-N-(6-methylpyrindi-2-ylmethyl)ethane-1,2-diamine]iron dichloride,
[N-2,4-dimethylphenyl-N-(6-methylpyrindi-2-ylmethyl)ethane-1,2-diamine]nickel dichloride,
[N-2,4-dimethylphenyl-N-(6-methylpyrindi-2-ylmethyl)ethane-1,2-diamine]copper dichloride,
[N-2,4,6-trimethylphenyl-N-(6-methylpyrindi-2-ylmethyl)ethane-1,2-diamine]cobalt dichloride,
[N-2,4,6-trimethylphenyl-N-(6-methylpyrindi-2-ylmethyl)ethane-1,2-diamine]iron dichloride,
[N-2,4,6-trimethylphenyl-N-(6-methylpyrindi-2-ylmethyl)ethane-1,2-diamine]nickel dichloride,
[N-2,4,6-trimethylphenyl-N-(6-methylpyrindi-2-ylmethyl)ethane-1,2-diamine]copper dichloride,
[N-2,6-diisopropylphenyl-N-(6-methylpyrindi-2-ylmethyl)ethane-1,2-diamine]cobalt dichloride,
[N-2,6-diisopropylphenyl-N-(6-methylpyrindi-2-ylmethyl)ethane-1,2-diamine]iron dichloride,
[N-2,6-diisopropylphenyl-N-(6-methylpyrindi-2-ylmethyl)ethane-1,2-diamine]nickel dichloride,
[N-2,6-diisopropylphenyl-N-(6-methylpyrindi-2-ylmethyl)ethane-1,2-diamine]copper dichloride,
[N-2,4,6-triisopropylphenyl-N-(6-methylpyrindi-2-ylmethyl)ethane-1,2-diamine]cobalt dichloride,
[N-2,4,6-triisopropylphenyl-N-(6-methylpyrindi-2-ylmethyl)ethane-1,2-diamine]iron dichloride,
[N-2,4,6-triisopropylphenyl-N-(6-methylpyrindi-2-ylmethyl)ethane-1,2-diamine]nickel dichloride,
[N-2,4,6-triisopropylphenyl-N-(6-methylpyrindi-2-ylmethyl)ethane-1,2-diamine]copper dichloride,
[N-2,6-dimethylphenyl-N-(6-isopropylpyrindi-2-ylmethyl)ethane-1,2-diamine]cobalt dichloride,
[N-2,6-dimethylphenyl-N-(6-isopropylpyrindi-2-ylmethyl)ethane-1,2-diamine]iron dichloride,
[N-2,6-dimethylphenyl-N-(6-isopropylpyrindi-2-ylmethyl)ethane-1,2-diamine]nickel dichloride,
[N-2,6-dimethylphenyl-N-(6-isopropylpyrindi-2-ylmethyl)ethane-1,2-diamine]copper dichloride,
[N-2,4-dimethylphenyl-N-(6-isopropylpyrindi-2-ylmethyl)ethane-1,2-diamine]cobalt dichloride,
[N-2,4-dimethylphenyl-N-(6-isopropylpyrindi-2-ylmethyl)ethane-1,2-diamine]iron dichloride,
[N-2,4-dimethylphenyl-N-(6-isopropylpyrindi-2-ylmethyl)ethane-1,2-diamine]nickel dichloride,
[N-2,4-dimethylphenyl-N-(6-isopropylpyrindi-2-ylmethyl)ethane-1,2-diamine]copper dichloride,
[N-2,4,6-trimethylphenyl-N-(6-isopropylpyrindi-2-ylmethyl)ethane-1,2-diamine]cobalt dichloride,
[N-2,4,6-trimethylphenyl-N-(6-isopropylpyrindi-2-ylmethyl)ethane-1,2-diamine]iron dichloride,
[N-2,4,6-trimethylphenyl-N-(6-isopropylpyrindi-2-ylmethyl)ethane-1,2-diamine]nickel dichloride,
[N-2,4,6-trimethylphenyl-N-(6-isopropylpyrindi-2-ylmethyl)ethane-1,2-diamine]copper dichloride,
[N-2,6-diisopropylphenyl-N-(6-isopropylpyrindi-2-ylmethyl)ethane-1,2-diamine]cobalt dichloride,
[N-2,6-diisopropylphenyl-N-(6-isopropylpyrindi-2-ylmethyl)ethane-1,2-diamine]iron dichloride,
[N-2,6-diisopropylphenyl-N-(6-isopropylpyrindi-2-ylmethyl)ethane-1,2-diamine]nickel dichloride,
[N-2,6-diisopropylphenyl-N-(6-isopropylpyrindi-2-ylmethyl)ethane-1,2-diamine]copper dichloride,
[N-2,4,6-triisopropylphenyl-N-(6-isopropylpyrindi-2-ylmethyl)ethane-1,2-diamine]cobalt dichloride,
[N-2,4,6-triisopropylphenyl-N-(6-isopropylpyrindi-2-ylmethyl)ethane-1,2-diamine]iron dichloride,
[N-2,4,6-triisopropylphenyl-N-(6-isopropylpyrindi-2-ylmethyl)ethane-1,2-diamine]nickel dichloride,
[N-2,4,6-triisopropylphenyl-N-(6-isopropylpyrindi-2-ylmethyl)ethane-1,2-diamine]copper dichloride,
[N-2,6-dimethylphenyl-N-methyl-N-(6-methylpyrindi-2-ylmethyl)ethane-1,2-diamine]cobalt dichloride,
[N-2,6-dimethylphenyl-N-methyl-N-(6-methylpyrindi-2-ylmethyl)ethane-1,2-diamine]iron dichloride,
[N-2,6-dimethylphenyl-N-methyl-N-(6-methylpyrindi-2-ylmethyl)ethane-1,2-diamine]nickel dichloride,
[N-2,6-dimethylphenyl-N-methyl-N-(6-methylpyrindi-2-ylmethyl)ethane-1,2-diamine]copper dichloride,
[N-2,4-dimethylphenyl-N-methyl-N-(6-methylpyrindi-2-ylmethyl)ethane-1,2-diamine]cobalt dichloride,
[N-2,4-dimethylphenyl-N-methyl-N-(6-methylpyrindi-2-ylmethyl)ethane-1,2-diamine]iron dichloride,

[N-2,4-dimethylphenyl-N-methyl-N-(6-methylpyrindi-2-yl-methyl)ethane-1,2-diamine]nickel dichloride,
[N-2,4-dimethylphenyl-N-methyl-N-(6-methylpyrindi-2-yl-methyl)ethane-1,2-diamine]copper dichloride,
[N-2,4,6-trimethylphenyl-N-methyl-N-(6-methylpyrindi-2-ylmethyl)ethane-1,2-diamine]cobalt dichloride,
[N-2,4,6-trimethylphenyl-N-methyl-N-(6-methylpyrindi-2-ylmethyl)ethane-1,2-diamine]iron dichloride,
[N-2,4,6-trimethylphenyl-N-methyl-N-(6-methylpyrindi-2-ylmethyl)ethane-1,2-diamine]nickel dichloride,
[N-2,4,6-trimethylphenyl-N-methyl-N-(6-methylpyrindi-2-ylmethyl)ethane-1,2-diamine]copper dichloride,
[N-2,6-diisopropylphenyl-N-methyl-N-(6-methylpyrindi-2-ylmethyl)ethane-1,2-diamine]cobalt dichloride,
[N-2,6-diisopropylphenyl-N-methyl-N-(6-methylpyrindi-2-ylmethyl)ethane-1,2-diamine]iron dichloride,
[N-2,6-diisopropylphenyl-N-methyl-N-(6-methylpyrindi-2-ylmethyl)ethane-1,2-diamine]nickel dichloride,
[N-2,6-diisopropylphenyl-N-methyl-N-(6-methylpyrindi-2-ylmethyl)ethane-1,2-diamine]copper dichloride,
[N-2,4,6-triisopropylphenyl-N-methyl-N-(6-methylpyrindi-2-ylmethyl)ethane-1,2-diamine]cobalt dichloride,
[N-2,4,6-triisopropylphenyl-N-methyl-N-(6-methylpyrindi-2-ylmethyl)ethane-1,2-diamine]iron dichloride,
[N-2,4,6-triisopropylphenyl-N-methyl-N-(6-methylpyrindi-2-ylmethyl)ethane-1,2-diamine]nickel dichloride,
[N-2,4,6-triisopropylphenyl-N-methyl-N-(6-methylpyrindi-2-ylmethyl)ethane-1,2-diamine]copper dichloride,
[N-2,6-dimethylphenyl-N-phenyl-N-(6-methylpyrindi-2-yl-methyl)ethane-1,2-diamine]cobalt dichloride,
[N-2,6-dimethylphenyl-N-phenyl-N-(6-methylpyrindi-2-yl-methyl)ethane-1,2-diamine]iron dichloride,
[N-2,6-dimethylphenyl-N-phenyl-N-(6-methylpyrindi-2-yl-methyl)ethane-1,2-diamine]nickel dichloride,
[N-2,6-dimethylphenyl-N-phenyl-N-(6-methylpyrindi-2-yl-methyl)ethane-1,2-diamine]copper dichloride,
[N-2,4-dimethylphenyl-N-phenyl-N-(6-methylpyrindi-2-yl-methyl)ethane-1,2-diamine]cobalt dichloride,
[N-2,4-dimethylphenyl-N-phenyl-N-(6-methylpyrindi-2-yl-methyl)ethane-1,2-diamine]iron dichloride,
[N-2,4-dimethylphenyl-N-phenyl-N-(6-methylpyrindi-2-yl-methyl)ethane-1,2-diamine]nickel dichloride,
[N-2,4-dimethylphenyl-N-phenyl-N-(6-methylpyrindi-2-yl-methyl)ethane-1,2-diamine]copper dichloride,
[N-2,4,6-trimethylphenyl-N-phenyl-N-(6-methylpyrindi-2-ylmethyl)ethane-1,2-diamine]cobalt dichloride,
[N-2,4,6-trimethylphenyl-N-phenyl-N-(6-methylpyrindi-2-ylmethyl)ethane-1,2-diamine]iron dichloride,
[N-2,4,6-trimethylphenyl-N-phenyl-N-(6-methylpyrindi-2-ylmethyl)ethane-1,2-diamine]nickel dichloride,
[N-2,4,6-trimethylphenyl-N-phenyl-N-(6-methylpyrindi-2-ylmethyl)ethane-1,2-diamine]copper dichloride,
[N-2,6-diisopropylphenyl-N-phenyl-N-(6-methylpyrindi-2-ylmethyl)ethane-1,2-diamine]cobalt dichloride,
[N-2,6-diisopropylphenyl-N-phenyl-N-(6-methylpyrindi-2-ylmethyl)ethane-1,2-diamine]iron dichloride,
[N-2,6-diisopropylphenyl-N-phenyl-N-(6-methylpyrindi-2-ylmethyl)ethane-1,2-diamine]nickel dichloride,
[N-2,6-diisopropylphenyl-N-phenyl-N-(6-methylpyrindi-2-ylmethyl)ethane-1,2-diamine]copper dichloride,
[N-2,4,6-triisopropylphenyl-N-phenyl-N-(6-methylpyrindi-2-ylmethyl)ethane-1,2-diamine]cobalt dichloride,
[N-2,4,6-triisopropylphenyl-N-phenyl-N-(6-methylpyrindi-2-ylmethyl)ethane-1,2-diamine]iron dichloride,
[N-2,4,6-triisopropylphenyl-N-phenyl-N-(6-methylpyrindi-2-ylmethyl)ethane-1,2-diamine]nickel dichloride,
[N-2,4,6-triisopropylphenyl-N-phenyl-N-(6-methylpyrindi-2-ylmethyl)ethane-1,2-diamine]copper dichloride,
[N-phenyl-2-aminoethyl)(2-picolyl)amine]cobalt dichloride,
[N-phenyl-2-aminoethyl)(2-picolyl)amine]iron dichloride,
[N-phenyl-2-aminoethyl)(2-picolyl)amine]nickel dichloride,
[N-phenyl-2-aminoethyl)(2-picolyl)amine]copper dichloride,
[N-2,6-diisopropyl-4-methylphenyl-2-aminoethyl)(2-picolyl)amine]cobalt dichloride,
[N-2,6-diisopropyl-4-methylphenyl-2-aminoethyl)(2-picolyl)amine]iron dichloride,
[N-2,6-diisopropyl-4-methylphenyl-2-aminoethyl)(2-picolyl)amine]nickel dichloride,
[N-2,6-diisopropyl-4-methylphenyl-2-aminoethyl)(2-picolyl)amine]copper dichloride,
[bis(2-picolyl)(N-2,6-dimethylphenyl-2-aminoethyl)amine]cobalt dichloride,
[bis(2-picolyl)(N-2,6-dimethylphenyl-2-aminoethyl)amine]iron dichloride,
[bis(2-picolyl)(N-2,4-dimethylphenyl-2-aminoethyl)amine]cobalt dichloride,
[bis(2-picolyl)(N-2,4-dimethylphenyl-2-aminoethyl)amine]iron dichloride,
[bis(2-picolyl)(N-2,4,6-trimethylphenyl-2-aminoethyl)amine]cobalt dichloride,
[bis(2-picolyl)(N-2,4,6-trimethylphenyl-2-aminoethyl)amine]iron dichloride,
[N-(2,6-dimethylphenyl)-N,N-bis(6-methylpyridin-2-ylmethyl)ethane-1,2-diamine]iron dichloride,
[N-(2,6-dimethylphenyl)-N,N-bis(6-methylpyridin-2-ylmethyl)ethane-1,2-diamine]cobalt dichloride,
[N-(2,4,6-trimethylphenyl)-N,N-bis(6-methylpyridin-2-ylmethyl)ethane-1,2-diamine]iron dichloride,
[N-(2,4,6-trimethylphenyl)-N,N-bis(6-methylpyridin-2-ylmethyl)ethane-1,2-diamine]cobalt dichloride,
[bis(2-picolyl)(N-2,6-dimethylphenyl-2-aminoethyl)amine]cobalt dichloride dimer,
[bis(2-picolyl)(N-2,4,6-trimethylphenyl-2-aminoethyl)amine]cobalt dichloride dimer,
[bis(2-picolyl)(N-2,4,6-trimethylphenyl-2-aminoethyl)amine]iron dichloride dimer,
[bis(2-picolyl)(N-2,4,6-trimethylphenyl-2-aminoethyl)amine]manganese dichloride dimer,
[N-2,6-dimethylphenyl-2-aminoethyl)(2-picolyl)amine]cobalt dibromide,
[N-2,6-dimethylphenyl-2-aminoethyl)(2-picolyl)amine]iron dibromide,
[N-2,6-dimethylphenyl-2-aminoethyl)(2-picolyl)amine]nickel dibromide,
[N-2,6-dimethylphenyl-2-aminoethyl)(2-picolyl)amine]copper dibromide,
[N-2,4-dimethylphenyl-2-aminoethyl)(2-picolyl)amine]cobalt dibromide,
[N-2,4-dimethylphenyl-2-aminoethyl)(2-picolyl)amine]iron dibromide,
[N-2,4-dimethylphenyl-2-aminoethyl)(2-picolyl)amine]nickel dibromide,
[N-2,4-dimethylphenyl-2-aminoethyl)(2-picolyl)amine]copper dibromide,
[N-2,4,6-trimethylphenyl-2-aminoethyl)(2-picolyl)amine]cobalt dibromide,
[N-2,4,6-trimethylphenyl-2-aminoethyl)(2-picolyl)amine]iron dibromide,
[N-2,4,6-trimethylphenyl-2-aminoethyl)(2-picolyl)amine]nickel dibromide,

[N-2,4,6-trimethylphenyl-2-aminoethyl)(2-picolyl)amine] copper dibromide,
[N-2,6-diisopropylphenyl-2-aminoethyl)(2-picolyl)amine] cobalt dibromide,
[N-2,6-diisopropylphenyl-2-aminoethyl)(2-picolyl)amine] iron dibromide,
[N-2,6-diisopropylphenyl-2-aminoethyl)(2-picolyl)amine] nickel dibromide,
[N-2,6-diisopropylphenyl-2-aminoethyl)(2-picolyl)amine] copper dibromide,
[N-2,4,6-triisopropylphenyl-2-aminoethyl)(2-picolyl) amine]cobalt dibromide,
[N-2,4,6-triisopropylphenyl-2-aminoethyl)(2-picolyl) amine]iron dibromide,
[N-2,4,6-triisopropylphenyl-2-aminoethyl)(2-picolyl) amine]nickel dibromide,
[N-2,4,6-triisopropylphenyl-2-aminoethyl)(2-picolyl) amine]copper dibromide,
[N-2,6-dimethylphenyl-2-aminopropyl)(2-picolyl)amine] cobalt dibromide,
[N-2,6-dimethylphenyl-2-aminopropyl)(2-picolyl)amine] iron dibromide,
[N-2,6-dimethylphenyl-2-aminopropyl)(2-picolyl)amine] nickel dibromide,
[N-2,6-dimethylphenyl-2-aminopropyl)(2-picolyl)amine] copper dibromide,
[N-2,4-dimethylphenyl-2-aminopropyl)(2-picolyl)amine] cobalt dibromide,
[N-2,4-dimethylphenyl-2-aminopropyl)(2-picolyl)amine] iron dibromide,
[N-2,4-dimethylphenyl-2-aminopropyl)(2-picolyl)amine] nickel dibromide,
[N-2,4-dimethylphenyl-2-aminopropyl)(2-picolyl)amine] copper dibromide,
[N-2,4,6-trimethylphenyl-2-aminopropyl)(2-picolyl)amine] cobalt dibromide,
[N-2,4,6-trimethylphenyl-2-aminopropyl)(2-picolyl)amine] iron dibromide,
[N-2,4,6-trimethylphenyl-2-aminopropyl)(2-picolyl)amine] nickel dibromide,
[N-2,4,6-trimethylphenyl-2-aminopropyl)(2-picolyl)amine] copper dibromide,
[N-2,6-diisopropylphenyl-2-aminopropyl)(2-picolyl)amine] cobalt dibromide,
[N-2,6-diisopropylphenyl-2-aminopropyl)(2-picolyl)amine] iron dibromide,
[N-2,6-diisopropylphenyl-2-aminopropyl)(2-picolyl)amine] nickel dibromide,
[N-2,6-diisopropylphenyl-2-aminopropyl)(2-picolyl)amine] copper dibromide,
[N-2,4,6-triisopropylphenyl-2-aminopropyl)(2-picolyl) amine]cobalt dibromide,
[N-2,4,6-triisopropylphenyl-2-aminopropyl)(2-picolyl) amine]iron dibromide,
[N-2,4,6-triisopropylphenyl-2-aminopropyl)(2-picolyl) amine]nickel dibromide,
[N-2,4,6-triisopropylphenyl-2-aminopropyl)(2-picolyl) amine]copper dibromide,
[N-2-methylphenyl-2-aminoethyl)(2-picolyl)amine]cobalt dibromide,
[N-2-methylphenyl-2-aminoethyl)(2-picolyl)amine]iron dibromide,
[N-2-methylphenyl-2-aminoethyl)(2-picolyl)amine]nickel dibromide,
[N-2-methylphenyl-2-aminoethyl)(2-picolyl)amine]copper dibromide,
[N-2-isopropylphenyl-2-aminoethyl)(2-picolyl)amine]cobalt dibromide,
[N-2-isopropylphenyl-2-aminoethyl)(2-picolyl)amine]iron dibromide,
[N-2-isopropylphenyl-2-aminoethyl)(2-picolyl)amine] nickel dibromide,
[N-2-isopropylphenyl-2-aminoethyl)(2-picolyl)amine]copper dibromide,
[N-2,6-dimethylphenyl-N-(6-methylpyrindi-2-ylmethyl) ethane-1,2-diamine]cobalt dibromide,
[N-2,6-dimethylphenyl-N-(6-methylpyrindi-2-ylmethyl) ethane-1,2-diamine]iron dibromide,
[N-2,6-dimethylphenyl-N-(6-methylpyrindi-2-ylmethyl) ethane-1,2-diamine]nickel dibromide,
[N-2,6-dimethylphenyl-N-(6-methylpyrindi-2-ylmethyl) ethane-1,2-diamine]copper dibromide,
[N-2,4-dimethylphenyl-N-(6-methylpyrindi-2-ylmethyl) ethane-1,2-diamine]cobalt dibromide,
[N-2,4-dimethylphenyl-N-(6-methylpyrindi-2-ylmethyl) ethane-1,2-diamine]iron dibromide,
[N-2,4-dimethylphenyl-N-(6-methylpyrindi-2-ylmethyl) ethane-1,2-diamine]nickel dibromide,
[N-2,4-dimethylphenyl-N-(6-methylpyrindi-2-ylmethyl) ethane-1,2-diamine]copper dibromide,
[N-2,4,6-trimethylphenyl-N-(6-methylpyrindi-2-ylmethyl) ethane-1,2-diamine]cobalt dibromide,
[N-2,4,6-trimethylphenyl-N-(6-methylpyrindi-2-ylmethyl) ethane-1,2-diamine]iron dibromide,
[N-2,4,6-trimethylphenyl-N-(6-methylpyrindi-2-ylmethyl) ethane-1,2-diamine]nickel dibromide,
[N-2,4,6-trimethylphenyl-N-(6-methylpyrindi-2-ylmethyl) ethane-1,2-diamine]dibromide dichloride,
[N-2,6-diisopropylphenyl-N-(6-methylpyrindi-2-ylmethyl) ethane-1,2-diamine]cobalt dibromide,
[N-2,6-diisopropylphenyl-N-(6-methylpyrindi-2-ylmethyl) ethane-1,2-diamine]iron dibromide,
[N-2,6-diisopropylphenyl-N-(6-methylpyrindi-2-ylmethyl) ethane-1,2-diamine]nickel dibromide,
[N-2,6-diisopropylphenyl-N-(6-methylpyrindi-2-ylmethyl) ethane-1,2-diamine]copper dibromide,
[N-2,4,6-triisopropylphenyl-N-(6-methylpyrindi-2-ylmethyl)ethane-1,2-diamine]cobalt dibromide,
[N-2,4,6-triisopropylphenyl-N-(6-methylpyrindi-2-ylmethyl)ethane-1,2-diamine]iron dibromide,
[N-2,4,6-triisopropylphenyl-N-(6-methylpyrindi-2-ylmethyl)ethane-1,2-diamine]nickel dibromide,
[N-2,4,6-triisopropylphenyl-N-(6-methylpyrindi-2-ylmethyl)ethane-1,2-diamine]copper dibromide,
[N-2,6-dimethylphenyl-N-(6-isopropylpyrindi-2-ylmethyl) ethane-1,2-diamine]cobalt dibromide,
[N-2,6-dimethylphenyl-N-(6-isopropylpyrindi-2-ylmethyl) ethane-1,2-diamine]iron dibromide,
[N-2,6-dimethylphenyl-N-(6-isopropylpyrindi-2-ylmethyl) ethane-1,2-diamine]nickel dibromide,
[N-2,6-dimethylphenyl-N-(6-isopropylpyrindi-2-ylmethyl) ethane-1,2-diamine]copper dibromide,
[N-2,4-dimethylphenyl-N-(6-isopropylpyrindi-2-ylmethyl) ethane-1,2-diamine]cobalt dibromide,
[N-2,4-dimethylphenyl-N-(6-isopropylpyrindi-2-ylmethyl) ethane-1,2-diamine]iron dibromide,
[N-2,4-dimethylphenyl-N-(6-isopropylpyrindi-2-ylmethyl) ethane-1,2-diamine]nickel dibromide,
[N-2,4-dimethylphenyl-N-(6-isopropylpyrindi-2-ylmethyl) ethane-1,2-diamine]copper dibromide,
[N-2,4,6-trimethylphenyl-N-(6-isopropylpyrindi-2-ylmethyl)ethane-1,2-diamine]cobalt dibromide,

[N-2,4,6-trimethylphenyl-N-(6-isopropylpyrindi-2-ylmethyl)ethane-1,2-diamine]iron dibromide,
[N-2,4,6-trimethylphenyl-N-(6-isopropylpyrindi-2-ylmethyl)ethane-1,2-diamine]nickel dibromide,
[N-2,4,6-trimethylphenyl-N-(6-isopropylpyrindi-2-ylmethyl)ethane-1,2-diamine]copper dibromide,
[N-2,6-diisopropylphenyl-N-(6-isopropylpyrindi-2-ylmethyl)ethane-1,2-diamine]cobalt dibromide,
[N-2,6-diisopropylphenyl-N-(6-isopropylpyrindi-2-ylmethyl)ethane-1,2-diamine]iron dibromide,
[N-2,6-diisopropylphenyl-N-(6-isopropylpyrindi-2-ylmethyl)ethane-1,2-diamine]nickel dibromide,
[N-2,6-diisopropylphenyl-N-(6-isopropylpyrindi-2-ylmethyl)ethane-1,2-diamine]copper dibromide,
[N-2,4,6-triisopropylphenyl-N-(6-isopropylpyrindi-2-ylmethyl)ethane-1,2-diamine]cobalt dibromide,
[N-2,4,6-triisopropylphenyl-N-(6-isopropylpyrindi-2-ylmethyl)ethane-1,2-diamine]iron dibromide,
[N-2,4,6-triisopropylphenyl-N-(6-isopropylpyrindi-2-ylmethyl)ethane-1,2-diamine]nickel dibromide,
[N-2,4,6-triisopropylphenyl-N-(6-isopropylpyrindi-2-ylmethyl)ethane-1,2-diamine]copper dibromide,
[N-2,6-dimethylphenyl-N-methyl-N-(6-methylpyrindi-2-ylmethyl)ethane-1,2-diamine]cobalt dibromide,
[N-2,6-dimethylphenyl-N-methyl-N-(6-methylpyrindi-2-ylmethyl)ethane-1,2-diamine]iron dibromide,
[N-2,6-dimethylphenyl-N-methyl-N-(6-methylpyrindi-2-ylmethyl)ethane-1,2-diamine]nickel dibromide,
[N-2,6-dimethylphenyl-N-methyl-N-(6-methylpyrindi-2-ylmethyl)ethane-1,2-diamine]copper dibromide,
[N-2,4-dimethylphenyl-N-methyl-N-(6-methylpyrindi-2-ylmethyl)ethane-1,2-diamine]cobalt dibromide,
[N-2,4-dimethylphenyl-N-methyl-N-(6-methylpyrindi-2-ylmethyl)ethane-1,2-diamine]iron dibromide,
[N-2,4-dimethylphenyl-N-methyl-N-(6-methylpyrindi-2-ylmethyl)ethane-1,2-diamine]nickel dibromide,
[N-2,4-dimethylphenyl-N-methyl-N-(6-methylpyrindi-2-ylmethyl)ethane-1,2-diamine]copper dibromide,
[N-2,4,6-trimethylphenyl-N-methyl-N-(6-methylpyrindi-2-ylmethyl)ethane-1,2-diamine]cobalt dibromide,
[N-2,4,6-trimethylphenyl-N-methyl-N-(6-methylpyrindi-2-ylmethyl)ethane-1,2-diamine]iron dibromide,
[N-2,4,6-trimethylphenyl-N-methyl-N-(6-methylpyrindi-2-ylmethyl)ethane-1,2-diamine]nickel dibromide,
[N-2,4,6-trimethylphenyl-N-methyl-N-(6-methylpyrindi-2-ylmethyl)ethane-1,2-diamine]copper dibromide,
[N-2,6-diisopropylphenyl-N-methyl-N-(6-methylpyrindi-2-ylmethyl)ethane-1,2-diamine]cobalt dibromide,
[N-2,6-diisopropylphenyl-N-methyl-N-(6-methylpyrindi-2-ylmethyl)ethane-1,2-diamine]iron dibromide,
[N-2,6-diisopropylphenyl-N-methyl-N-(6-methylpyrindi-2-ylmethyl)ethane-1,2-diamine]nickel dibromide,
[N-2,6-diisopropylphenyl-N-methyl-N-(6-methylpyrindi-2-ylmethyl)ethane-1,2-diamine]copper dibromide,
[N-2,4,6-triisopropylphenyl-N-methyl-N-(6-methylpyrindi-2-ylmethyl)ethane-1,2-diamine]cobalt dibromide,
[N-2,4,6-triisopropylphenyl-N-methyl-N-(6-methylpyrindi-2-ylmethyl)ethane-1,2-diamine]iron dibromide,
[N-2,4,6-triisopropylphenyl-N-methyl-N-(6-methylpyrindi-2-ylmethyl)ethane-1,2-diamine]nickel dibromide,
[N-2,4,6-triisopropylphenyl-N-methyl-N-(6-methylpyrindi-2-ylmethyl)ethane-1,2-diamine]copper dibromide,
[N-2,6-dimethylphenyl-N-phenyl-N-(6-methylpyrindi-2-ylmethyl)ethane-1,2-diamine]cobalt dibromide,
[N-2,6-dimethylphenyl-N-phenyl-N-(6-methylpyrindi-2-ylmethyl)ethane-1,2-diamine]iron dibromide,
[N-2,6-dimethylphenyl-N-phenyl-N-(6-methylpyrindi-2-ylmethyl)ethane-1,2-diamine]nickel dibromide,
[N-2,6-dimethylphenyl-N-phenyl-N-(6-methylpyrindi-2-ylmethyl)ethane-1,2-diamine]copper dibromide,
[N-2,4-dimethylphenyl-N-phenyl-N-(6-methylpyrindi-2-ylmethyl)ethane-1,2-diamine]cobalt dibromide,
[N-2,4-dimethylphenyl-N-phenyl-N-(6-methylpyrindi-2-ylmethyl)ethane-1,2-diamine]iron dibromide,
[N-2,4-dimethylphenyl-N-phenyl-N-(6-methylpyrindi-2-ylmethyl)ethane-1,2-diamine]nickel dibromide,
[N-2,4-dimethylphenyl-N-phenyl-N-(6-methylpyrindi-2-ylmethyl)ethane-1,2-diamine]copper dibromide,
[N-2,4,6-trimethylphenyl-N-phenyl-N-(6-methylpyrindi-2-ylmethyl)ethane-1,2-diamine]cobalt dibromide,
[N-2,4,6-trimethylphenyl-N-phenyl-N-(6-methylpyrindi-2-ylmethyl)ethane-1,2-diamine]iron dibromide,
[N-2,4,6-trimethylphenyl-N-phenyl-N-(6-methylpyrindi-2-ylmethyl)ethane-1,2-diamine]nickel dibromide,
[N-2,4,6-trimethylphenyl-N-phenyl-N-(6-methylpyrindi-2-ylmethyl)ethane-1,2-diamine]copper dibromide,
[N-2,6-diisopropylphenyl-N-phenyl-N-(6-methylpyrindi-2-ylmethyl)ethane-1,2-diamine]cobalt dibromide,
[N-2,6-diisopropylphenyl-N-phenyl-N-(6-methylpyrindi-2-ylmethyl)ethane-1,2-diamine]iron dibromide,
[N-2,6-diisopropylphenyl-N-phenyl-N-(6-methylpyrindi-2-ylmethyl)ethane-1,2-diamine]nickel dibromide,
[N-2,6-diisopropylphenyl-N-phenyl-N-(6-methylpyrindi-2-ylmethyl)ethane-1,2-diamine]copper dibromide,
[N-2,4,6-triisopropylphenyl-N-phenyl-N-(6-methylpyrindi-2-ylmethyl)ethane-1,2-diamine]cobalt dibromide,
[N-2,4,6-triisopropylphenyl-N-phenyl-N-(6-methylpyrindi-2-ylmethyl)ethane-1,2-diamine]iron dibromide,
[N-2,4,6-triisopropylphenyl-N-phenyl-N-(6-methylpyrindi-2-ylmethyl)ethane-1,2-diamine]nickel dibromide,
[N-2,4,6-triisopropylphenyl-N-phenyl-N-(6-methylpyrindi-2-ylmethyl)ethane-1,2-diamine]copper dibromide,
[N-phenyl-2-aminoethyl)(2-picolyl)amine]cobalt dibromide,
[N-phenyl-2-aminoethyl)(2-picolyl)amine]iron dibromide,
[N-phenyl-2-aminoethyl)(2-picolyl)amine]nickel dibromide,
[N-phenyl-2-aminoethyl)(2-picolyl)amine]copper dibromide,
[N-2,6-diisopropyl-4-methylphenyl-2-aminoethyl)(2-picolyl)amine]cobalt dibromide,
[N-2,6-diisopropyl-4-methylphenyl-2-aminoethyl)(2-picolyl)amine]iron dibromide,
[N-2,6-diisopropyl-4-methylphenyl-2-aminoethyl)(2-picolyl)amine]nickel dibromide,
[N-2,6-diisopropyl-4-methylphenyl-2-aminoethyl)(2-picolyl)amine]copper dibromide,
[bis(2-picolyl)(N-2,6-dimethylphenyl-2-aminoethyl)amine]cobalt dibromide,
[bis(2-picolyl)(N-2,6-dimethylphenyl-2-aminoethyl)amine]iron dibromide,
[bis(2-picolyl)(N-2,4-dimethylphenyl-2-aminoethyl)amine]cobalt dibromide,
[bis(2-picolyl)(N-2,4-dimethylphenyl-2-aminoethyl)amine]iron dibromide,
[bis(2-picolyl)(N-2,4,6-trimethylphenyl-2-aminoethyl)amine]cobalt dibromide,
[bis(2-picolyl)(N-2,4,6-trimethylphenyl-2-aminoethyl)amine]iron dibromide,
[N-(2,6-dimethylphenyl)-N,N-bis(6-methylpyridin-2-ylmethyl)ethane-1,2-diamine]iron dibromide,
[N-(2,6-dimethylphenyl)-N,N-bis(6-methylpyridin-2-ylmethyl)ethane-1,2-diamine]cobalt dibromide,

[N-(2,4,6-trimethylphenyl)-N,N-bis(6-methylpyridin-2-yl-methyl)ethane-1,2-diamine]iron dibromide,
[N-(2,4,6-trimethylphenyl)-N,N-bis(6-methylpyridin-2-yl-methyl)ethane-1,2-diamine]cobalt dibromide,
[bis(2-picolyl)(N-2,6-dimethylphenyl-2-aminoethyl)amine] cobalt dibromide dimer,
[bis(2-picolyl)(N-2,4,6-trimethylphenyl-2-aminoethyl) amine]cobalt dibromide dimer,
[bis(2-picolyl)(N-2,4,6-trimethylphenyl-2-aminoethyl) amine]iron dibromide dimer,
[bis(2-picolyl)(N-2,4,6-trimethylphenyl-2-aminoethyl) amine]manganese dibromide dimer,
[N-2,6-dimethylphenyl-2-aminoethyl)(2-picolyl)amine] rhodium dichloride,
[N-2,6-dimethylphenyl-2-aminoethyl)(2-picolyl)amine]ruthenium dichloride,
[N-2,6-dimethylphenyl-2-aminoethyl)(2-picolyl)amine]palladium dichloride,
[N-2,6-dimethylphenyl-2-aminoethyl)(2-picolyl)amine]silver dichloride,
[N-2,4-dimethylphenyl-2-aminoethyl)(2-picolyl)amine] rhodium dichloride,
[N-2,4-dimethylphenyl-2-aminoethyl)(2-picolyl)amine]ruthenium dichloride,
[N-2,4-dimethylphenyl-2-aminoethyl)(2-picolyl)amine]palladium dichloride,
[N-2,4-dimethylphenyl-2-aminoethyl)(2-picolyl)amine]silver dichloride,
[N-2,4,6-trimethylphenyl-2-aminoethyl)(2-picolyl)amine] rhodium dichloride,
[N-2,4,6-trimethylphenyl-2-aminoethyl)(2-picolyl)amine] ruthenium dichloride,
[N-2,4,6-trimethylphenyl-2-aminoethyl)(2-picolyl)amine] palladium dichloride,
[N-2,4,6-trimethylphenyl-2-aminoethyl)(2-picolyl)amine] silver dichloride,
[N-2,6-diisopropylphenyl-2-aminoethyl)(2-picolyl)amine] rhodium dichloride,
[N-2,6-diisopropylphenyl-2-aminoethyl)(2-picolyl)amine] ruthenium dichloride,
[N-2,6-diisopropylphenyl-2-aminoethyl)(2-picolyl)amine] palladium dichloride,
[N-2,6-diisopropylphenyl-2-aminoethyl)(2-picolyl)amine] silver dichloride,
[N-2,4,6-triisopropylphenyl-2-aminoethyl)(2-picolyl) amine]rhodium dichloride,
[N-2,4,6-triisopropylphenyl-2-aminoethyl)(2-picolyl) amine]ruthenium dichloride,
[N-2,4,6-triisopropylphenyl-2-aminoethyl)(2-picolyl) amine]palladium dichloride,
[N-2,4,6-triisopropylphenyl-2-aminoethyl)(2-picolyl) amine]silver dichloride,
[N-2,6-dimethylphenyl-2-aminopropyl)(2-picolyl)amine] rhodium dichloride,
[N-2,6-dimethylphenyl-2-aminopropyl)(2-picolyl)amine] ruthenium dichloride,
[N-2,6-dimethylphenyl-2-aminopropyl)(2-picolyl)amine] palladium dichloride,
[N-2,6-dimethylphenyl-2-aminopropyl)(2-picolyl)amine] silver dichloride,
[N-2,6-diisopropylphenyl-2-aminopropyl)(2-picolyl)amine] rhodium dichloride,
[N-2,6-diisopropylphenyl-2-aminopropyl)(2-picolyl)amine] ruthenium dichloride,
[N-2,6-diisopropylphenyl-2-aminopropyl)(2-picolyl)amine] palladium dichloride,
[N-2,6-diisopropylphenyl-2-aminopropyl)(2-picolyl)amine] silver dichloride,
[N-2-methylphenyl-2-aminoethyl)(2-picolyl)amine] rhodium dichloride,
[N-2-methylphenyl-2-aminoethyl)(2-picolyl)amine]ruthenium dichloride,
[N-2-methylphenyl-2-aminoethyl)(2-picolyl)amine]palladium dichloride,
[N-2-methylphenyl-2-aminoethyl)(2-picolyl)amine]silver dichloride,
[N-2-isopropylphenyl-2-aminoethyl)(2-picolyl)amine] rhodium dichloride,
[N-2-isopropylphenyl-2-aminoethyl)(2-picolyl)amine]ruthenium dichloride,
[N-2-isopropylphenyl-2-aminoethyl)(2-picolyl)amine]palladium dichloride,
[N-2-isopropylphenyl-2-aminoethyl)(2-picolyl)amine]silver dichloride,
[N-2,6-dimethylphenyl-N-(6-methylpyrindi-2-ylmethyl) ethane-1,2-diamine]rhodium dichloride,
[N-2,6-dimethylphenyl-N-(6-methylpyrindi-2-ylmethyl) ethane-1,2-diamine]ruthenium dichloride,
[N-2,6-dimethylphenyl-N-(6-methylpyrindi-2-ylmethyl) ethane-1,2-diamine]palladium dichloride,
[N-2,6-dimethylphenyl-N-(6-methylpyrindi-2-ylmethyl) ethane-1,2-diamine]silver dichloride,
[N-2,4-dimethylphenyl-N-(6-methylpyrindi-2-ylmethyl) ethane-1,2-diamine]rhodium dichloride,
[N-2,4-dimethylphenyl-N-(6-methylpyrindi-2-ylmethyl) ethane-1,2-diamine]ruthenium dichloride,
[N-2,4-dimethylphenyl-N-(6-methylpyrindi-2-ylmethyl) ethane-1,2-diamine]palladium dichloride,
[N-2,4-dimethylphenyl-N-(6-methylpyrindi-2-ylmethyl) ethane-1,2-diamine]silver dichloride,
[N-2,4,6-trimethylphenyl-N-(6-methylpyrindi-2-ylmethyl) ethane-1,2-diamine]rhodium dichloride,
[N-2,4,6-trimethylphenyl-N-(6-methylpyrindi-2-ylmethyl) ethane-1,2-diamine]ruthenium dichloride,
[N-2,4,6-trimethylphenyl-N-(6-methylpyrindi-2-ylmethyl) ethane-1,2-diamine]palladium dichloride,
[N-2,4,6-trimethylphenyl-N-(6-methylpyrindi-2-ylmethyl) ethane-1,2-diamine]silver dichloride,
[N-2,6-diisopropylphenyl-N-(6-methylpyrindi-2-ylmethyl) ethane-1,2-diamine]rhodium dichloride,
[N-2,6-diisopropylphenyl-N-(6-methylpyrindi-2-ylmethyl) ethane-1,2-diamine]ruthenium dichloride,
[N-2,6-diisopropylphenyl-N-(6-methylpyrindi-2-ylmethyl) ethane-1,2-diamine]palladium dichloride,
[N-2,6-diisopropylphenyl-N-(6-methylpyrindi-2-ylmethyl) ethane-1,2-diamine]silver dichloride,
[N-2,6-dimethylphenyl-N-(6-isopropylpyrindi-2-ylmethyl) ethane-1,2-diamine]rhodium dichloride,
[N-2,6-dimethylphenyl-N-(6-isopropylpyrindi-2-ylmethyl) ethane-1,2-diamine]ruthenium dichloride,
[N-2,6-dimethylphenyl-N-(6-isopropylpyrindi-2-ylmethyl) ethane-1,2-diamine]palladium dichloride,
[N-2,6-dimethylphenyl-N-(6-isopropylpyrindi-2-ylmethyl) ethane-1,2-diamine]silver dichloride,
[N-2,6-diisopropylphenyl-N-(6-isopropylpyrindi-2-ylm-ethyl)ethane-1,2-diamine]rhodium dichloride,
[N-2,6-diisopropylphenyl-N-(6-isopropylpyrindi-2-ylm-ethyl)ethane-1,2-diamine]ruthenium dichloride,
[N-2,6-diisopropylphenyl-N-(6-isopropylpyrindi-2-ylm-ethyl)ethane-1,2-diamine]palladium dichloride,
[N-2,6-diisopropylphenyl-N-(6-isopropylpyrindi-2-ylm-ethyl)ethane-1,2-diamine]silver dichloride,

[N-2,6-dimethylphenyl-N-methyl-N-(6-methylpyrindi-2-yl-methyl)ethane-1,2-diamine]rhodium dichloride,
[N-2,6-dimethylphenyl-N-methyl-N-(6-methylpyrindi-2-yl-methyl)ethane-1,2-diamine]ruthenium dichloride,
[N-2,6-dimethylphenyl-N-methyl-N-(6-methylpyrindi-2-yl-methyl)ethane-1,2-diamine]palladium dichloride,
[N-2,6-dimethylphenyl-N-methyl-N-(6-methylpyrindi-2-yl-methyl)ethane-1,2-diamine]silver dichloride,
[N-2,6-diisopropylphenyl-N-methyl-N-(6-methylpyrindi-2-ylmethyl)ethane-1,2-diamine]rhodium dichloride,
[N-2,6-diisopropylphenyl-N-methyl-N-(6-methylpyrindi-2-ylmethyl)ethane-1,2-diamine]ruthenium dichloride,
[N-2,6-diisopropylphenyl-N-methyl-N-(6-methylpyrindi-2-ylmethyl)ethane-1,2-diamine]palladium dichloride,
[N-2,6-diisopropylphenyl-N-methyl-N-(6-methylpyrindi-2-ylmethyl)ethane-1,2-diamine]silver dichloride,
[N-2,6-dimethylphenyl-N-phenyl-N-(6-methylpyrindi-2-yl-methyl)ethane-1,2-diamine]rhodium dichloride,
[N-2,6-dimethylphenyl-N-phenyl-N-(6-methylpyrindi-2-yl-methyl)ethane-1,2-diamine]ruthenium dichloride,
[N-2,6-dimethylphenyl-N-phenyl-N-(6-methylpyrindi-2-yl-methyl)ethane-1,2-diamine]palladium dichloride,
[N-2,6-dimethylphenyl-N-phenyl-N-(6-methylpyrindi-2-yl-methyl)ethane-1,2-diamine]silver dichloride,
[N-2,6-diisopropylphenyl-N-phenyl-N-(6-methylpyrindi-2-ylmethyl)ethane-1,2-diamine]rhodium dichloride,
[N-2,6-diisopropylphenyl-N-phenyl-N-(6-methylpyrindi-2-ylmethyl)ethane-1,2-diamine]ruthenium dichloride,
[N-2,6-diisopropylphenyl-N-phenyl-N-(6-methylpyrindi-2-ylmethyl)ethane-1,2-diamine]palladium dichloride,
[N-2,6-diisopropylphenyl-N-phenyl-N-(6-methylpyrindi-2-ylmethyl)ethane-1,2-diamine]silver dichloride,
[N-phenyl-2-aminoethyl)(2-picolyl)amine]rhodium dichloride,
[N-phenyl-2-aminoethyl)(2-picolyl)amine]ruthenium dichloride,
[N-phenyl-2-aminoethyl)(2-picolyl)amine]palladium dichloride,
[N-phenyl-2-aminoethyl)(2-picolyl)amine]silver dichloride,
[N-2,6-diisopropyl-4-methylphenyl-2-aminoethyl)(2-picolyl)amine]rhodium dichloride,
[N-2,6-diisopropyl-4-methylphenyl-2-aminoethyl)(2-picolyl)amine]ruthenium dichloride,
[N-2,6-diisopropyl-4-methylphenyl-2-aminoethyl)(2-picolyl)amine]palladium dichloride,
[N-2,6-diisopropyl-4-methylphenyl-2-aminoethyl)(2-picolyl)amine]silver dichloride,
[bis(2-picolyl)(N-2,6-dimethylphenyl-2-aminoethyl)amine]rhodium dichloride,
[bis(2-picolyl)(N-2,6-dimethylphenyl-2-aminoethyl)amine]ruthenium dichloride,
[bis(2-picolyl)(N-2,4-dimethylphenyl-2-aminoethyl)amine]rhodium dichloride,
[bis(2-picolyl)(N-2,4-dimethylphenyl-2-aminoethyl)amine]ruthenium dichloride,
[bis(2-picolyl)(N-2,4,6-trimethylphenyl-2-aminoethyl)amine]rhodium dichloride,
[bis(2-picolyl)(N-2,4,6-trimethylphenyl-2-aminoethyl)amine]ruthenium dichloride,
[N-(2,6-dimethylphenyl)-N,N-bis(6-methylpyridin-2-ylmethyl)ethane-1,2-diamine]ruthenium dibromide,
[N-(2,6-dimethylphenyl)-N,N-bis(6-methylpyridin-2-ylmethyl)ethane-1,2-diamine]rhodium dibromide,
[N-(2,4,6-trimethylphenyl)-N,N-bis(6-methylpyridin-2-yl-methyl)ethane-1,2-diamine]ruthenium dibromide,
[N-(2,4,6-trimethylphenyl)-N,N-bis(6-methylpyridin-2-yl-methyl)ethane-1,2-diamine]rhodium dibromide,
[bis(2-picolyl)(N-2,6-dimethylphenyl-2-aminoethyl)amine]rhodium dichloride dimer,
[bis(2-picolyl)(N-2,4,6-trimethylphenyl-2-aminoethyl)amine]rhodium dichloride dimer,
[bis(2-picolyl)(N-2,4,6-trimethylphenyl-2-aminoethyl)amine]ruthenium dichloride dimer, and
[bis(2-picolyl)(N-2,4,6-trimethylphenyl-2-aminoethyl)amine]rhenium dichloride dimer.

Most preferred transition metal complexes include:
[N-2,6-dimethylphenyl-2-aminoethyl)(2-picolyl)amine]cobalt dichloride,
[N-2,6-dimethylphenyl-2-aminoethyl)(2-picolyl)amine]iron dichloride,
[N-2,6-dimethylphenyl-2-aminoethyl)(2-picolyl)amine]nickel dichloride,
[N-2,6-dimethylphenyl-2-aminoethyl)(2-picolyl)amine]copper dichloride,
[N-2,4-dimethylphenyl-2-aminoethyl)(2-picolyl)amine]cobalt dichloride,
[N-2,4-dimethylphenyl-2-aminoethyl)(2-picolyl)amine]iron dichloride,
[N-2,4-dimethylphenyl-2-aminoethyl)(2-picolyl)amine]nickel dichloride,
[N-2,4-dimethylphenyl-2-aminoethyl)(2-picolyl)amine]copper dichloride,
[N-2,4,6-trimethylphenyl-2-aminoethyl)(2-picolyl)amine]cobalt dichloride,
[N-2,4,6-trimethylphenyl-2-aminoethyl)(2-picolyl)amine]iron dichloride,
[N-2,4,6-trimethylphenyl-2-aminoethyl)(2-picolyl)amine]nickel dichloride,
[N-2,4,6-trimethylphenyl-2-aminoethyl)(2-picolyl)amine]copper dichloride,
[N-2,6-diisopropylphenyl-2-aminoethyl)(2-picolyl)amine]cobalt dichloride,
[N-2,6-diisopropylphenyl-2-aminoethyl)(2-picolyl)amine]iron dichloride,
[N-2,6-diisopropylphenyl-2-aminoethyl)(2-picolyl)amine]nickel dichloride,
[N-2,6-diisopropylphenyl-2-aminoethyl)(2-picolyl)amine]copper dichloride,
[N-2,4,6-triisopropylphenyl-2-aminoethyl)(2-picolyl)amine]cobalt dichloride,
[N-2,4,6-triisopropylphenyl-2-aminoethyl)(2-picolyl)amine]iron dichloride,
[N-2,4,6-triisopropylphenyl-2-aminoethyl)(2-picolyl)amine]nickel dichloride,
[N-2,4,6-triisopropylphenyl-2-aminoethyl)(2-picolyl)amine]copper dichloride,
[N-2,6-dimethylphenyl-N-(6-methylpyrindi-2-ylmethyl)ethane-1,2-diamine]cobalt dichloride,
[N-2,6-dimethylphenyl-N-(6-methylpyrindi-2-ylmethyl)ethane-1,2-diamine]iron dichloride,
[N-2,6-dimethylphenyl-N-(6-methylpyrindi-2-ylmethyl)ethane-1,2-diamine]nickel dichloride,
[N-2,6-dimethylphenyl-N-(6-methylpyrindi-2-ylmethyl)ethane-1,2-diamine]copper dichloride,
[N-2,4-dimethylphenyl-N-(6-methylpyrindi-2-ylmethyl)ethane-1,2-diamine]cobalt dichloride,
[N-2,4-dimethylphenyl-N-(6-methylpyrindi-2-ylmethyl)ethane-1,2-diamine]iron dichloride,
[N-2,4-dimethylphenyl-N-(6-methylpyrindi-2-ylmethyl)ethane-1,2-diamine]nickel dichloride,
[N-2,4-dimethylphenyl-N-(6-methylpyrindi-2-ylmethyl)ethane-1,2-diamine]copper dichloride,
[N-2,4,6-trimethylphenyl-N-(6-methylpyrindi-2-ylmethyl)ethane-1,2-diamine]cobalt dichloride,

[N-2,4,6-trimethylphenyl-N-(6-methylpyrindi-2-ylmethyl) ethane-1,2-diamine]iron dichloride,
[N-2,4,6-trimethylphenyl-N-(6-methylpyrindi-2-ylmethyl) ethane-1,2-diamine]nickel dichloride,
[N-2,4,6-trimethylphenyl-N-(6-methylpyrindi-2-ylmethyl) ethane-1,2-diamine]copper dichloride,
[N-2,6-diisopropylphenyl-N-(6-methylpyrindi-2-ylmethyl) ethane-1,2-diamine]cobalt dichloride,
[N-2,6-diisopropylphenyl-N-(6-methylpyrindi-2-ylmethyl) ethane-1,2-diamine]iron dichloride,
[N-2,6-diisopropylphenyl-N-(6-methylpyrindi-2-ylmethyl) ethane-1,2-diamine]nickel dichloride,
[N-2,6-diisopropylphenyl-N-(6-methylpyrindi-2-ylmethyl) ethane-1,2-diamine]copper dichloride,
[N-2,4,6-triisopropylphenyl-N-(6-methylpyrindi-2-ylmethyl)ethane-1,2-diamine]cobalt dichloride,
[N-2,4,6-triisopropylphenyl-N-(6-methylpyrindi-2-ylmethyl)ethane-1,2-diamine]iron dichloride,
[N-2,4,6-triisopropylphenyl-N-(6-methylpyrindi-2-ylmethyl)ethane-1,2-diamine]nickel dichloride,
[N-2,4,6-triisopropylphenyl-N-(6-methylpyrindi-2-ylmethyl)ethane-1,2-diamine]copper dichloride,
[bis(2-picolyl)(N-2,6-dimethylphenyl-2-aminoethyl)amine] cobalt dichloride,
[bis(2-picolyl)(N-2,6-dimethylphenyl-2-aminoethyl)amine] iron dichloride,
[bis(2-picolyl)(N-2,4-dimethylphenyl-2-aminoethyl)amine] cobalt dichloride,
[bis(2-picolyl)(N-2,4-dimethylphenyl-2-aminoethyl)amine] iron dichloride,
[bis(2-picolyl)(N-2,4,6-trimethylphenyl-2-aminoethyl) amine]cobalt dichloride,
[bis(2-picolyl)(N-2,4,6-trimethylphenyl-2-aminoethyl) amine]iron dichloride,
[N-(2,6-dimethylphenyl)-N,N-bis(6-methylpyridin-2-ylmethyl)ethane-1,2-diamine]iron dichloride,
[N-(2,6-dimethylphenyl)-N,N-bis(6-methylpyridin-2-ylmethyl)ethane-1,2-diamine]cobalt dichloride,
[N-(2,4,6-trimethylphenyl)-N,N-bis(6-methylpyridin-2-ylmethyl)ethane-1,2-diamine]iron dichloride,
[N-(2,4,6-trimethylphenyl)-N,N-bis(6-methylpyridin-2-ylmethyl)ethane-1,2-diamine]cobalt dichloride,
[bis(2-picolyl)(N-2,6-dimethylphenyl-2-aminoethyl)amine] cobalt dichloride dimer,
[bis(2-picolyl)(N-2,4,6-trimethylphenyl-2-aminoethyl) amine]cobalt dichloride dimer,
[bis(2-picolyl)(N-2,4,6-trimethylphenyl-2-aminoethyl) amine]iron dichloride dimer, and
[bis(2-picolyl)(N-2,4,6-trimethylphenyl-2-aminoethyl) amine]manganese dichloride dimer.

Transition metal complexes of this invention are typically prepared by reacting the tridentate or tetradentate ligand, L, with the desired metal halide, preferably a metal dihalide, in an appropriate solvent, preferably n-butanol, and heating the reaction mixture.

Invention catalyst systems can additionally be prepared by combining, in any order, the ligand, with a Group 7, 8, 9, 10 or 11 metal halide salt, which may optionally be coordinated by solvent, in an activator solution (for example, methylalumoxane dissolved in toluene). All reactants may be added in any order, or even essentially simultaneously.

Common activators that are useful with this invention include:
1. Alumoxanes including alkyl alumoxanes and modified alkylalumoxanes, such as methylalumoxane, modified methylalumoxane, ethylalumoxane and the like;
2. Aluminum alkyls such as trimethyl aluminum, triethyl aluminum, triisopropyl aluminum and the like, and alkyl aluminum halides such as diethyl aluminum chloride, and including alkylaluminum alkoxides; and
3. Ionizing or stoichiometric activators.

Alumoxane components useful as an activators typically are an oligomeric aluminum compound represented by the general formula (R"—Al—O)n, which is a cyclic compound, or R"(R"—Al—O)nAlR"2, which is a linear compound. In this general alumoxane formula, each R" is independently a C1–C20 alkyl radical, for example, methyl, ethyl, propyl, butyl, pentyl, isomers thereof, and the like, and "n" is an integer from 1–50. Most preferably, R" is methyl and "n" is at least 4. Methylalumoxane and/or modified methylalumoxanes are most preferred. Another preferred alumoxane is a modified methyl alumoxane (MMAO) cocatalyst type 3A (commercially available from Akzo Chemicals, Inc. under the trade name Modified Methylalumoxane type 3A, U.S. Pat. No. 5,041,584). For further descriptions see, EP 279586, EP 561476, WO94/10180 and U.S. Pat. Nos. 4,665,208, 4,908,463, 4,924,018, 4,952,540, 4,968,827, 5,041,584, 5,103,031, 5,157,137, 5,235,081, 5,248,801, 5,329,032, 5,391,793, and 5,416,229.

Aluminum alkyl components useful as activators are represented by the general formula: Rm'''AlZp where each R''' is, independently, a $C_1$–$C_{20}$ alkyl radical, for example, methyl, ethyl, propyl, butyl, pentyl, hexyl, heptyl, octyl, nonyl, decyl, undecyl, dodecyl, and isomers thereof, preferably methyl, ethyl, propyl, butyl, isobutyl, hexyl, octyl, more preferably methyl, ethyl, isobutyl, n-hexyl or n-octyl;

m is 1, 2 or 3;

each Z is, independently, a $C_1$–$C_{20}$ alkyl radical, for example, methyl, ethyl, propyl, butyl, pentyl, hexyl, heptyl, octyl, nonyl, decyl, undecyl, dodecyl, and isomers thereof, preferably methyl, ethyl, propyl, butyl, isobutyl, hexyl, octyl, or n-octyl, each Z may also be a different univalent anionic ligand such as a halogen (preferably Cl, Br, I), or an alkoxide (OR*), where R* is a $C_1$–$C_{20}$ alkyl radical, for example, methyl, ethyl, propyl, butyl, pentyl, hexyl, heptyl, octyl, nonyl, decyl, undecyl, dodecyl, and isomers thereof, preferably methyl, ethyl, propyl, butyl, isobutyl, hexyl, octyl, or n-octyl, preferably R* is preferably methyl, ethyl, propyl, butyl, isobutyl, hexyl, octyl, n-octyl, chloro, methoxide, ethoxide, propoxide, isopropoxide, butoxide, or t-butoxide; and p is 0, 1 or 2. Preferred aluminum alkyl compounds which may be utilized as activators (or scavengers) include triethylaluminum, diethylaluminum chloride, triisobutylaluminum, tri-n-octylaluminum, trimethylaluminum, and tri-n-hexylaluminum.

When alumoxane, or aluminum alkyl activators are used, the catalyst-precursor-to-activator molar ratio is preferably from about 1:2000 to 10:1; alternatively, 1:1200 to 1:1; alternatively, 1:1000 to 1:1; alternatively 1:500 to 1:1; alternatively 1:400 to 1:10, or alternatively 1:300 to 1:10.

Ionizing activators may be used in the practice of this invention. Preferably, discrete ionizing activators (sometimes also referred to as ionic activators) such as [Me$_2$PhNH][B(C$_6$F$_5$)$_4$], [Bu$_3$NH][BF$_4$], [NH$_4$][PF$_6$], [NH$_4$][SbF$_6$], [NH4][AsF6], [NH4][B(C6H5)4] or Lewis acidic activators such as B(C6F5)$_3$ or B(C$_6$H$_5$)$_3$ can be used if they are used in conjunction with a compound capable of alkylating the metal such as an alumoxane or aluminum alkyl, or if in the pre-catalyst, X is a hydride, hydrocarbyl, substituted hydrocarbyl, halocarbyl, substituted halocarbyl. For purposes of this invention and the claims thereto, Ph is phenyl, Bu is butyl, $C_6H_5$ is phenyl; $C_6F_5$ is perfluorophenyl or pentafluorophenyl.

An ionizing or stoichiometric activator may be used, neutral or ionic, such as tri(n-butyl)ammonium tetrakis (pentafluorophenyl)boron, a tris(perfluorophenyl)boron metalloid precursor or a tris(perfluoronaphthyl)boron metalloid precursor, polyhalogenated heteroborane anions (see WO 98/43983), boric acid (see U.S. Pat. No. 5,942,459) or combination thereof. Neutral or ionizing activators may also be used alone or in combination with alumoxane or modified alumoxane activators.

Examples of neutral stoichiometric activators include: tri-substituted boron, tellurium, aluminum, gallium and indium or mixtures thereof. The three substituent groups are each independently selected from alkyls, alkenyls, halogen, substituted alkyls, aryls, arylhalides, alkoxy and halides. Preferably, the three groups are independently selected from halogen, mono or multicyclic (including halosubstituted) aryls, alkyls, and alkenyl compounds, and mixtures thereof. Preferred are alkenyl groups having 1 to 20 carbon atoms, alkyl groups having 1 to 20 carbon atoms, alkoxy groups having 1 to 20 carbon atoms, and aryl groups having 3 to 20 carbon atoms (including substituted aryls). More preferably, the three groups are alkyls having 1 to 4 carbon groups, phenyl, naphthyl or mixtures thereof. Even more preferably, the three groups are halogenated aryl groups, preferably fluorinated aryl groups. Most preferably, the neutral stoichiometric activator is tris(perfluorophenyl)boron or tris (perfluoronaphthyl)boron.

Ionizing stoichiometric activator compounds may contain an active proton, or some other cation associated with, but not coordinated to, or only loosely coordinated to, the remaining ion of the ionizing compound. Such compounds and the like are described in European publications EP-A-0 570 982, EP-A-0 520 732, EP-A-0 495 375, EP-B1-0 500 944, EP-A-0 277 003 and EP-A-0 277 004, and U.S. Pat. Nos. 5,153,157, 5,198,401, 5,066,741, 5,206,197, 5,241, 025, 5,384,299 and 5,502,124 and U.S. patent application Ser. No. 08/285,380, filed Aug. 3, 1994, all of which are herein fully incorporated by reference.

Ionic catalysts can be prepared by reacting a transition metal compound with one or more neutral Lewis acids, such as $B(C_6F_6)_3$, which upon reaction with the hydrolyzable ligand (X) of the transition metal compound forms an anion, such as ([$B(C_6F_5)3(X)$]—), which stabilizes the cationic transition metal species generated by the reaction. The catalysts can be, and preferably are, prepared with activator components which are ionic compounds or compositions. However preparation of activators utilizing neutral compounds is possible.

Compounds useful as an activator component in the preparation of the ionic catalyst systems may also comprise a cation, which is preferably a Bronsted acid capable of donating a proton, and a compatible non-coordinating anion which anion is relatively large (sterically bulky), capable of stabilizing the active catalyst species which is formed when the two compounds are combined, and said anion will be sufficiently labile to be displaced by olefinicm, diolefinic and acetylenically unsaturated substrates or other neutral Lewis bases such as ethers, nitriles and the like. Two classes of compatible non-coordinating anions are (as disclosed in EPA 277,003 and EPA 277,004 published 1988:1. anionic coordination complexes comprising a plurality of lipophilic radicals covalently coordinated to and shielding a central charge-bearing metal or metalloid core, and 2. anions comprising a plurality of boron atoms such as carboranes, metallacarboranes and boranes.

In a preferred embodiment, the stoichiometric activators include a cation and an anion component, and may be represented by the following formula:

(14)

wherein L* is an neutral Lewis base;
H is hydrogen;
(L*-H)$^+$ is a Bronsted acid
A$^{d-}$ is a non-coordinating anion having the charge d–
d is an integer from 1 to 3.

The cation component, (L*-H)d+ may include Bronsted acids such as protons or protonated Lewis bases or reducible Lewis acids capable of protonating or abstracting a moiety, such as an alkyl or aryl, from the transition metal catalyst compound, resulting in a cationic transition metal species.

The activating cation (L*-H)d+ may be a Bronsted acid, capable of donating a proton to the transition metal catalytic precursor resulting in a transition metal cation, including ammoniums, oxoniums, phosphoniums, silyliums, and mixtures thereof, preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, and phosphoniums from triethylphosphine, triphenylphosphine, and diphenylphosphine, oxomiuns from ethers such as dimethyl ether diethyl ether, tetrahydrofuran and dioxane, sulfoniums from thioethers, such as diethyl thioethers and tetrahydrothiophene, and mixtures thereof. The activating cation (L-H)d+ may also be a moiety such as silver, tropylium, carbeniums, ferroceniums and mixtures thereof, preferably carboniums and ferroceniums. Most preferably (L*-H)d+ is triphenyl carbonium.

The anion component Ad– includes those having the formula [Mk+Qn]d– wherein k is an integer from 1 to 3; n is an integer from 2–6; n–k=d; M is an element selected from Group 13 of the Periodic Table of the Elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, or halosubstituted-hydrocarbyl radical, said Q having up to 20 carbon atoms with the proviso that not more than one Q group is a halide. Preferably, each Q is a fluorinated hydrocarbyl group having 1 to 20 carbon atoms, more preferably each Q is a fluorinated aryl group, and most preferably each Q is a pentafluoryl aryl group. Examples of suitable Ad– also include diboron compounds as disclosed in U.S. Pat. No. 5,447,895, which is fully incorporated herein by reference.

Illustrative, but not limiting examples of boron compounds which may be used as an activating cocatalyst (activator) include:
trimethylammonium tetraphenylborate, triethylammonium tetraphenylborate, tripropylammonium tetraphenylborate, tri(n-butyl)ammonium tetraphenylborate, tri(t-butyl)ammonium tetraphenylborate, N,N-dimethylanilinium tetraphenylborate, N,N-diethylanilinium tetraphenylborate, N,N-dimethyl-(2,4,6-trimethylanilinium) tetraphenylborate, tropillium tetraphenylborate, triphenylcarbenium tetraphenylborate, triphenylphosphonium tetraphenylborate triethylsilylium tetraphenylborate, benzene(diazonium) tetraphenylborate, di(isopropyl)ammonium tetraphenylborate, dicyclohexylammonium tetraphenylborate; tri (o-tolyl)phosphonium tetraphenylborate, tri(2,6-dimethylphenyl)phosphonium tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium) tetrakis(pentafluorophenyl)borate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene(diazonium) tetrakis(pentafluorophenyl)borate, di(isopropyl)ammonium tetrakis(pentafluorophenyl)borate, dicyclohexylammonium tetrakis(pentafluorophenyl)borate; tri(o-tolyl)phosphonium tetrakis(pentafluorophenyl)borate, tri(2,6-dimethylphenyl)phosphonium tetrakis(pentafluorophenyl)borate, trimethylammonium tetrakis-(2,3,4,6-tetrafluorophenyl)borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluorophenyl)borate, dimethyl(t-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium) tetrakis-(2,3,4,6-tetrafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium) tetrakis-(2,3,4,6-tetrafluorophenyl)borate, di(isopropyl)ammonium tetrakis(2,3,4,6-tetrafluorophenyl)borate, dicyclohexylammonium tetrakis(2,3,4,6-tetrafluorophenyl)borate; tri(o-tolyl)phosphonium tetrakis(2,3,4,6-tetrafluorophenyl)borate, tri(2,6-dimethylphenyl)phosphonium tetrakis(2,3,4,6-tetrafluorophenyl)borate, trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(t-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium) tetrakis(perfluoronaphthyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium) tetrakis(perfluoronaphthyl)borate, di(isopropyl)ammonium tetrakis(pentafluoronaphthyl)borate, dicyclohexylammonium tetrakis(pentafluoronaphthyl)borate; tri(o-tolyl)phosphonium tetrakis(pentafluoronaphthyl)borate, tri(2,6-dimethylphenyl)phosphonium tetrakis(pentafluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(t-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium) tetrakis(perfluorobiphenyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium) tetrakis(perfluorobiphenyl)borate, di(isopropyl)ammonium tetrakis(pentafluorobiphenyl)borate, dicyclohexylammonium tetrakis(pentafluorobiphenyl)borate; tri(o-tolyl)phosphonium tetrakis(pentafluorobiphenyl)borate, tri(2,6-dimethylphenyl)phosphonium tetrakis(pentafluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri(n-butyl)ammonium tetrakis(3,5-bis(trifluoromethyl)phenyl)borate, tri(t-butyl)ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium) tetrakis(3,5-bis(trifluoromethyl)phenyl)borate, tropillium tetrakis(3,5-bis(trifluoromethyl)phenyl)borate, triphenylcarbenium tetrakis(3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl)phenyl)borate, benzene(diazonium) tetrakis(3,5-bis(trifluoromethyl)phenyl)borate, di(isopropyl)ammonium tetrakis(3,5-bis(trifluoromethyl)phenyl)borate, dicyclohexylammonium tetrakis(3,5-bis(trifluoromethyl)phenyl)borate; tri(o-tolyl)phosphonium tetrakis(3,5-bis(trifluoromethyl)phenyl)borate, and tri(2,6-dimethylphenyl)phosphonium tetrakis(3,5-bis(trifluoromethyl)phenyl)borate.

Most preferably, the ionic stoichiometric activator (L*-H)d+ (Ad−) comprises one or more of:

N,N-dimethylanilinium tetra(perfluorophenyl)borate, N,N-dimethylanilinium tetrakis(perfluoronaphthyl)borate, N,N-dimethylanilinium tetrakis(perfluorobiphenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, or triphenylcarbenium tetra(perfluorophenyl)borate.

One embodiment includes an activation method using ionizing ionic compounds not containing an active proton, but capable of producing a ligand metallocene catalyst cation, and their non-coordinating anion. These are described in EP-A-0 426 637, EP-A-0 573 403 and U.S. Pat. No. 5,387,568, which are all herein incorporated by reference.

Invention catalyst precursors can also be activated with cocatalysts or activators that comprise non-coordinating anions containing metalloid-free cyclopentadienide ions. These are described in U.S. Patent Publication 2002/0058765 A1, published on 16 May 2002.

The term "non-coordinating anion" (NCA) means an anion which either does not coordinate to said cation or which is only weakly coordinated to said cation thereby remaining sufficiently labile to be displaced by a neutral Lewis base. "Compatible" non-coordinating anions are those which are not degraded to neutrality when the initially formed complex decomposes. Further, the anion will not transfer an anionic substituent or fragment to the cation so as to cause it to form a neutral four coordinate metallocene compound and a neutral by-product from the anion. Non-coordinating anions include those that are compatible, stabilize the metallocene cation in the sense of balancing its ionic charge at +1, yet retain sufficient lability to permit displacement by an ethylenically, or acetylenically unsaturated monomer during polymerization. These types of cocatalysts sometimes use tri-isobutyl aluminum or tri-octyl aluminum as a scavenger.

Cocatalyst compounds or activator compounds may also be initially neutral Lewis acids, but form a cationic metal complex and a noncoordinating anion, or a zwitterionic complex upon reaction with the invention compounds. For example, tris(pentafluorophenyl) boron or aluminum act to abstract a hydrocarbyl or hydride ligand to yield an invention cationic metal complex and stabilizing noncoordinating anion. (See EP-A-0 427 697 and EP-A-0 520 732 for illustrations of analogous Group-4 metallocene compounds.) Also, see the methods and compounds of EP-A-0 495 375. For formation of zwitterionic complexes using analogous Group 4 compounds, see U.S. Pat. Nos. 5,624,878; 5,486,632; and 5,527,929.

When the cations of noncoordinating anion precursors are Bronsted acids such as protons or protonated Lewis bases (excluding water), or reducible Lewis acids such as ferrocenium or silver cations, or alkali or alkaline earth metal cations such as those of sodium, magnesium or lithium, the catalyst-precursor-to-activator molar ratio may be any ratio. Combinations of the described activator compounds may also be used for activation. For example, tris(perfluorophenyl) boron can be used with methylalumoxane.

When an ionic activator is used, the catalyst-precursor-to-activator molar ratio is from 1:10 to 1.2:1; 1:10 to 10:1; 1:10 to 2:1; 1:10 to 3:1; 1:10 to 5:1; 1:2 to 1.2:1; 1:2 to 10:1; 1:2 to 2:1; 1:2 to 3:1; 1:2 to 5:1; 1:3 to 1.2:1; 1:3 to 10:1; 1:3 to 2:1; 1:3 to 3:1; 1:3 to 5:1; 1:5 to 1.2:1; 1:5 to 10:1; 1:5 to 2:1; 1:5 to 3:1; 1:5 to 5:1.

The catalyst-precursor-to-alkylating-agent molar ratio is from 1:100 to 100:1; 1:50 to 50:1; 1:10 to 10:1; 1:10 to 2:1; 1:10 to 25:1; 1:10 to 3:1; 1:10 to 5:1; 1:2 to 10:1; 1:2 to 2:1; 1:2 to 25:1; 1:2 to 3:1; 1:2 to 5:1; 1:25 to 10:1; 1:25 to 2:1; 1:25 to 25:1; 1:25 to 3:1; 1:25 to 5:1; 1:3 to 10:1; 1:3 to 2:1; 1:3 to 25:1; 1:3 to 3:1; 1:3 to 5:1; 1:5 to 10:1; 1:5 to 2:1; 1:5 to 25:1; 1:5 to 3:1; 1:5 to 5:1.

Preferred activators include methylalumoxane, modified methylalumoxane, and mixtures of methylalumoxane with dimethylanilinium tetrakis(pentafluorophenyl)borate or tris (pentafluorophenyl)boron.

Preferred catalyst compound/activator combinations include:
[N-2,6-dimethylphenyl-2-aminoethyl)(2-picolyl)amine]cobalt dichloride/methylalumoxane,
[N-2,6-dimethylphenyl-2-aminoethyl)(2-picolyl)amine]iron dichloride/methylalumoxane,
[N-2,4-dimethylphenyl-2-aminoethyl)(2-picolyl)amine]cobalt dichloride/methylalumoxane,
[N-2,4-dimethylphenyl-2-aminoethyl)(2-picolyl)amine]iron dichloride/methylalumoxane,
[N-2,6-diisopropylphenyl-2-aminoethyl)(2-picolyl)amine] cobalt dichloride/methylalumoxane,
[N-2,6-diisopropylphenyl-2-aminoethyl)(2-picolyl)amine] iron dichloride/methylalumoxane,
[N-2,4,6-triisopropylphenyl-2-aminoethyl)(2-picolyl) amine]cobalt dichloride/methylalumoxane,
[N-2,4,6-triisopropylphenyl-2-aminoethyl)(2-picolyl) amine]iron dichloride/methylalumoxane,
[N-2,6-dimethylphenyl-N-(6-methylpyrindi-2-ylmethyl) ethane-1,2-diamine]cobalt dichloride/methylalumoxane,
[N-2,6-dimethylphenyl-N-(6-methylpyrindi-2-ylmethyl) ethane-1,2-diamine]iron dichloride/methylalumoxane,
[N-2,4-dimethylphenyl-N-(6-methylpyrindi-2-ylmethyl) ethane-1,2-diamine]cobalt dichloride/methylalumoxane,
[N-2,4-dimethylphenyl-N-(6-methylpyrindi-2-ylmethyl) ethane-1,2-diamine]iron dichloride/methylalumoxane,
[N-2,4,6-trimethylphenyl-N-(6-methylpyrindi-2-ylmethyl) ethane-1,2-diamine]cobalt dichloride/methylalumoxane,
[N-2,4,6-trimethylphenyl-N-(6-methylpyrindi-2-ylmethyl) ethane-1,2-diamine]iron dichloride/methylalumoxane,
[N-2,6-isopropylphenyl-N-(6-methylpyrindi-2-ylmethyl) ethane-1,2-diamine]cobalt dichloride/methylalumoxane,
[N-2,6-diisopropylphenyl-N-(6-methylpyrindi-2-ylmethyl) ethane-1,2-diamine]iron dichloride/methylalumoxane,
[N-2,4,6-triisopropylphenyl-N-(6-methylpyrindi-2-ylmethyl)ethane-1,2-diamine]cobalt dichloride/methylalumoxane,
[N-2,4,6-triisopropylphenyl-N-(6-methylpyrindi-2-ylmethyl)ethane-1,2-diamine]iron dichloride/methylalumoxane,
[N-2,4,6-trimethylphenyl-2-aminoethyl)(2-picolyl)amine] cobalt dichloride/methylalumoxane,
[N-2,4,6-trimethylphenyl-2-aminoethyl)(2-picolyl)amine] iron dichloride/methylalumoxane,
[bis(2-picolyl)(N-2,6-dimethylphenyl-2-aminoethyl)amine] cobalt dichloride/methylalumoxane,
[bis(2-picolyl)(N-2,6-dimethylphenyl-2-aminoethyl)amine] iron dichloride/methylalumoxane,
[bis(2-picolyl)(N-2,4,6-trimethylphenyl-2-aminoethyl) amine]cobalt dichloride/methylalumoxane
[bis(2-picolyl)(N-2,4,6-trimethylphenyl-2-aminoethyl) amine]iron dichloride/methylalumoxane,
[N-(2,6-dimethylphenyl)-N,N-bis(6-methylpyridin-2-ylmethyl)ethane-1,2-diamine]iron dichloride/methylalumoxane,
[N-(2,6-dimethylphenyl)-N,N-bis(6-methylpyridin-2-ylmethyl)ethane-1,2-diamine]cobalt dichloride/methylalumoxane,
[N-(2,4,6-trimethylphenyl)-N,N-bis(6-methylpyridin-2-ylmethyl)ethane-1,2-diamine]iron dichloride/methylalumoxane,
[N-(2,4,6-trimethylphenyl)-N,N-bis(6-methylpyridin-2-ylmethyl)ethane-1,2-diamine]cobalt dichloride/methylalumoxane,
[bis(2-picolyl)(N-2,6-dimethylphenyl-2-aminoethyl)amine] cobalt dichloride dimer/methylalumoxane,
[bis(2-picolyl)(N-2,6-dimethylphenyl-2-aminoethyl)amine] iron dichloride dimer/methylalumoxane,
[bis(2-picolyl)(N-2,4,6-trimethylphenyl-2-aminoethyl) amine]cobalt dichloride dimer/methylalumoxane,
[bis(2-picolyl)(N-2,4,6-trimethylphenyl-2-aminoethyl) amine]iron dichloride dimer/methylalumoxane,
[bis(2-picolyl)(N-2,4,6-trimethylphenyl-2-aminoethyl) amine]manganese dichloride dimer/alulmoxane,
[N-2,6-dimethylphenyl-2-aminoethyl)(2-picolyl)amine]cobalt dichloride/modified methylalumoxane,
[N-2,6-dimethylphenyl-2-aminoethyl)(2-picolyl)amine]iron dichloride/modified methylalumoxane,
[N-2,4-dimethylphenyl-2-aminoethyl)(2-picolyl)amine]cobalt dichloride/modified methylalumoxane,
[N-2,4-dimethylphenyl-2-aminoethyl)(2-picolyl)amine]iron dichloride/modified methylalumoxane,
[N-2,6-diisopropylphenyl-2-aminoethyl)(2-picolyl)amine] cobalt dichloride/modified methylalumoxane,
[N-2,6-diisopropylphenyl-2-aminoethyl)(2-picolyl)amine] iron dichloride/modified methylalumoxane,
[N-2,4,6-triisopropylphenyl-2-aminoethyl)(2-picolyl) amine]cobalt dichloride/modified methylalumoxane,

[N-2,4,6-triisopropylphenyl-2-aminoethyl)(2-picolyl) amine]iron dichloride/modified methylalumoxane,
[N-2,6-dimethylphenyl-N-(6-methylpyrindi-2-ylmethyl) ethane-1,2-diamine]cobalt dichloride/modified methylalumoxane,
[N-2,6-dimethylphenyl-N-(6-methylpyrindi-2-ylmethyl) ethane-1,2-diamine]iron dichloride/modified methylalumoxane,
[N-2,4-dimethylphenyl-N-(6-methylpyrindi-2-ylmethyl) ethane-1,2-diamine]cobalt dichloride/modified methylalumoxane,
[N-2,4-dimethylphenyl-N-(6-methylpyrindi-2-ylmethyl) ethane-1,2-diamine]iron dichloride/modified methylalumoxane,
[N-2,4,6-trimethylphenyl-N-(6-methylpyrindi-2-ylmethyl) ethane-1,2-diamine]cobalt dichloride/modified methylalumoxane,
[N-2,4,6-trimethylphenyl-N-(6-methylpyrindi-2-ylmethyl) ethane-1,2-diamine]iron dichloride/modified methylalumoxane,
[N-2,6-isopropylphenyl-N-(6-methylpyrindi-2-ylmethyl) ethane-1,2-diamine]cobalt dichloride/modified methylalumoxane,
[N-2,6-diisopropylphenyl-N-(6-methylpyrindi-2-ylmethyl) ethane-1,2-diamine]iron dichloride/modified methylalumoxane,
[N-2,4,6-triisopropylphenyl-N-(6-methylpyrindi-2-ylmethyl)ethane-1,2-diamine]cobalt dichloride/modified methylalumoxane,
[N-2,4,6-triisopropylphenyl-N-(6-methylpyrindi-2-ylmethyl)ethane-1,2-diamine]iron dichloride/modified methylalumoxane,
[N-2,4,6-trimethylphenyl-2-aminoethyl)(2-picolyl)amine] cobalt dichloride/modified methylalumoxane,
[N-2,4,6-trimethylphenyl-2-aminoethyl)(2-picolyl)amine] iron dichloride/modified methylalumoxane,
[bis(2-picolyl)(N-2,6-dimethylphenyl-2-aminoethyl)amine] cobalt dichloride/modified methylalumoxane,
[bis(2-picolyl)(N-2,6-dimethylphenyl-2-aminoethyl)amine] iron dichloride/modified methylalumoxane,
[bis(2-picolyl)(N-2,4,6-trimethylphenyl-2-aminoethyl) amine]cobalt dichloride/modified methylalumoxane
[bis(2-picolyl)(N-2,4,6-trimethylphenyl-2-aminoethyl) amine]iron dichloride/modified methylalumoxane,
[N-(2,6-dimethylphenyl)-N,N-bis(6-methylpyridin-2-ylmethyl)ethane-1,2-diamine]iron dichloride/modified methylalumoxane,
[N-(2,6-dimethylphenyl)-N,N-bis(6-methylpyridin-2-ylmethyl)ethane-1,2-diamine]cobalt dichloride/modified methylalumoxane,
[N-(2,4,6-trimethylphenyl)-N,N-bis(6-methylpyridin-2-ylmethyl)ethane-1,2-diamine]iron dichloride/modified methylalumoxane,
[N-(2,4,6-trimethylphenyl)-N,N-bis(6-methylpyridin-2-ylmethyl)ethane-1,2-diamine]cobalt dichloride/modified methylalumoxane,
[bis(2-picolyl)(N-2,6-dimethylphenyl-2-aminoethyl)amine] cobalt dichloride dimer/modified methylalumoxane,
[bis(2-picolyl)(N-2,6-dimethylphenyl-2-aminoethyl)amine] iron dichloride dimer/modified methylalumoxane,
[bis(2-picolyl)(N-2,4,6-trimethylphenyl-2-aminoethyl) amine]cobalt dichloride dimer/modified methylalumoxane,
[bis(2-picolyl)(N-2,4,6-trimethylphenyl-2-aminoethyl) amine]iron dichloride dimer/modified methylalumoxane, and
[bis(2-picolyl)(N-2,4,6-trimethylphenyl-2-aminoethyl) amine]manganese dichloride dimer/modified alulmoxane, Mixed Catalysts Mixed catalyst systems can also be used, for example, the invention catalyst can be used in conjunction with a second catalyst in the same reactor or in a series of reactors where the invention catalyst produces ethylene oligomers and the second catalyst incorporates these oligomers into a polymer backbone as a copolymer with ethylene.

Catalyst systems can comprise additional olefin polymerization catalysts. These additional olefin polymerization catalysts are any of those well known in the art to catalyze the olefin to polyolefin reaction. Some invention catalysts systems include Group-4–6 metallocenes as additional olefin polymerization catalysts. Metallocenes include (un) bridged compounds containing one (mono(cyclopentadienyl) metallocenes) or two (bis(cyclopentadienyl) metallocenes) (un)substituted cyclopentadienyl ligand(s). In bridged metallocenes, a single, cyclopentadienyl ligand connects to a heteroatom ligand with both coordinating to the metal center, or two cyclopentadienyl ligands connect together with both cyclopentadienyl ligands coordinating to the metal center. Typical catalysts and their precursors are well known in the art. Suitable description appears in the patent literature, for example U.S. Pat. Nos. 4,871,705, 4,937,299, 5,324,800, EP-A-0418044, EP-A-0591756, WO-A-92/00333 and WO-A-94/01471. Some embodiments select the metallocene compounds from mono- or bis-cyclopentadienyl-substituted, Group-4, -5, and -6 metals in which cyclopentadienyls are (un)substituted with one or more groups or are bridged to each other or to a metal-coordinated heteroatom. Some embodiments select similar metallocene compounds except they are not necessarily bridged to each other or to a metal-coordinated heteroatom. See U.S. Pat. Nos. 5,278,264 and 5,304,614.

Some invention catalysts systems include the following additional olefin polymerization catalysts. Metallocene compounds suitable for linear polyethylene or ethylene-containing copolymer production (where copolymer means comprising at least two different monomers) are essentially those disclosed in WO-A-92/00333, WO 97/44370 and U.S. Pat. Nos. 5,001,205, 5,057,475, 5,198,401, 5,304,614, 5,308,816 and 5,324,800. Selection of metallocene compounds for isotactic or syndiotactic polypropylene blend production, and their syntheses, are well-known in the patent and academic literature, e.g. Journal of Organometallic Chemistry 369, 359–370 (1989). Typically, those catalysts are stereorigid, asymmetric, chiral, or bridged-chiral metallocenes. Invention activators are suited for activating these types of catalyst precursors.

Likewise, some invention catalysts systems include the following additional olefin polymerization catalysts: mono-cyclopentadienyl metallocenes with Group-15 or -16 heteroatoms connected, through a bridging group, to a cyclopentadienyl-ligand ring carbon. Both the cyclopentadienyl Cp-ligand and the heteroatom connect to a transition metal. Some embodiments select a Group-4 transition metal. Additionally, unbridged monocyclopentadienyl, heteroatom-containing Group-4 components of WO 97/22639 will function with this invention. Moreover, transition metal systems with high-oxidation-state, Group-5–10 transition-metal centers are known and can serve as the additional olefin polymerization catalysts with invention catalyst systems.

Invention catalyst systems can use non-cyclopentadienyl, Group-4–5 precursor compounds as the additional olefin polymerization catalysts. Non-cyclopentadienyl, Group-4–5 precursor compounds that are activable to stable, discrete cationic complexes include those containing chelating, diamide ligands, such as described in U.S. Pat. No. 5,318,935, and "Conformationally Rigid Diamide Complexes: Synthesis and Structure of Tantalum (III) Alkyne Derivatives", D. H. McConville, et al, Organometallics 1995, 14, 3154–3156.

U.S. Pat. No. 5,318,935 describes bridged and unbridged, bis-amido catalyst compounds of Group-4 metals capable of α-olefins polymerization. Bridged bis(arylamido) Group-4 compounds for olefin polymerization are described by D. H. McConville, et al., in Organometallics 1995, 14, 5478–5480. Synthetic methods and compound characterization are described. Further work appearing in D. H. McConville, et al, Macromolecules 1996, 29, 5241–5243, describes bridged bis(arylamido) Group-4 compounds that are polymerization catalysts for 1-hexene. Additional invention-suitable transition-metal compounds include those described in WO 96/40805. Cationic Group-3- or Lanthanide olefin polymerization complexes are disclosed in copending U.S. application Ser. No. 09/408050, filed 29 Sep. 1999, and its equivalent PCT/US99/22690. Other suitable Group-4–5 non-metallocene catalysts are bimetallocyclic catalyst compounds comprising two independently selected Group-4–5 metal atoms directly linked through two bridging groups to form cyclic compounds.

Invention catalyst systems can use other transition metal catalyst precursors that have a 2+ oxidation state as the additional olefin polymerization catalyst. Typical $Ni_2^+$ and $Pd_2^+$ complexes are diimines, see "New Pd(II)- and Ni(II)-Based Catalysts for Polymerization of Ethylene and α-Olefins", M. Brookhart, et al, J. Am. Chem. Soc., 1995, 117, 6414–6415, WO 96/23010 and WO 97/02298. See additionally the related bis(imino) Group-8 and -9 organometallic compounds described by V. C. Gibson and others in "Novel olefin polymerization catalysts based on iron and cobalt", Chem. Commun., 849–850, 1998.

For a review of other potential catalysts used in combination or series with the invention catalysts, see S. D. Ittel and L. K. Johnson, Chem. Rev. 2000, 1000, 1169 and V. C. Gibson and S. K. Spitzmesser, Chem. Rev. 2003, 103, 283.

Some catalyst systems of this invention can produce greater than 95% linear α-olefins.

Supports

The transition metal catalyst components described herein may be supported. For example, one or more transition metal catalyst components and/or one or more activators may be deposited on, contacted with, vaporized with, bonded to, or incorporated within, adsorbed or absorbe supports or carriers.

The support material may be any of the conventional support materials. Preferably the support material is a porous support material, for example, talc, inorganic oxides and inorganic chlorides. Other support materials include resinous support materials such as polystyrene, functionalized or crosslinked organic supports, such as polystyrene divinyl benzene polyolefins or polymeric compounds, zeolites, clays, or any other organic or inorganic support material and the like, or mixtures thereof.

Preferred support materials are inorganic oxides that include those Group 2, 3, 4, 5, 13 or 14 metal oxides. Preferred supports include silica, which may or may not be dehydrated, fumed silica, alumina (WO 99/60033), silica-alumina and mixtures thereof. Other useful supports include magnesia, titania, zirconia, magnesium chloride (U.S. Pat. No. 5,965,477), montmorillonite (European Patent EP-B1 0 511 665), phyllosilicate, zeolites, talc, clays (U.S. Pat. No. 6,034,187) and the like. Also, combinations of these support materials may be used, for example, silica-chromium, silica-alumina, silica-titania and the like. Additional support materials may include those porous acrylic polymers described in EP 0 767 184 B1, which is incorporated herein by reference. Other support materials include nanocomposites as described in PCT WO 99/47598, aerogels as described in WO 99/48605, spherulites as described in U.S. Pat. No. 5,972,510 and polymeric beads as described in WO 99/50311, which are all herein incorporated by reference. Lewis acidic materials such as montmorillonite and similar clays may also serve as a support. In this case, the support can optionally double as the activator component. But additional activator may also be used.

Preferably the support material, most preferably an inorganic oxide, has a surface area in the range of from about 10 to about 700 m2/g, pore volume in the range of from about 0.1 to about 4.0 cc/g, and average particle size in the range of from about 5 to about 500 μm. More preferably, the surface area of the support material is in the range of from about 50 to about 500 m2/g, pore volume of from about 0.5 to about 3.5 cc/g, and average particle size of from about 10 to about 200 μm. Most preferably the surface area of the support material is in the range is from about 100 to about 400 m2/g, pore volume from about 0.8 to about 3.0 cc/g, and average particle size is from about 5 to about 100 μm. The average pore size of the carrier typically has pore size in the range of from 10 to 1000 Å, preferably 50 to about 500 Å, and most preferably 75 to about 350 Å.

As is known in the art, the catalysts may also be supported together on one inert support, or the catalysts may be independently placed on two inert supports and subsequently mixed. Of the two methods, the former is preferred.

In another embodiment the support may comprise one or more types of support material which may be treated differently. For example one could use two different silicas that have different pore volumes or have been calcined at different temperatures. Likewise one could use a silica that has been treated with a scavenger or other additive, and with a silica that has not been treated.

Supported transition metal catalyst compounds, activators, or catalyst systems may be prepared by placing the support material (which may be pre-treated, such as calcined or functionalized) and one or more catalyst compounds, or one or more activators, or both activators and catalyst compounds in a diluent, typically a solvent, and them removing the diluent or solvent. The volume of the liquid may be from 0.5 to 20 time the pore volume of the support or more. Certain embodiments, however, use 1 to 3 times the pore volume of the support or less than 1 times the pore volume of the support.

Typically supported catalyst systems are prepared by methods effective to support other coordination catalyst systems, effective meaning that the catalyst so prepared can be used for oligomerizing or polymerizing monomers in a heterogeneous process. The catalyst precursor, activator, suitable diluent, and support may be added in any order or simultaneously. In one invention embodiment, the activator, dissolved in an appropriate solvent such as toluene is stirred with the support material for 1 minute to 10 hours. The total volume of the activation solution may be greater than the pore volume of the support, but some embodiments limit the total solution volume below that needed to form a gel or slurry (about 100–200% of the pore volume). In some embodiments the volume of the solution is limited to between 1 and 5 times the pore volume of the support, typically between 1.5 and 3. The mixture is optionally heated to 30–200° C. during this time. The catalyst can be added to this mixture as a solid, if a suitable solvent is employed in the previous step, or as a solution. Or alternatively, this mixture can be filtered, and the resulting solid mixed with a catalyst precursor solution. Similarly, the mixture may be vacuum dried and mixed with a catalyst precursor solution. The resulting catalyst mixture is then stirred for 1 minute to 10 hours, and the catalyst is either filtered from the solution and vacuum dried, or vacuum or evaporation alone removes the solvent.

In another invention embodiment, the catalyst precursor and activator are combined in solvent to form a solution. The support is then added to this solution and the mixture is stirred for 1 minute to 10 hours. The total volume of this solution may be greater than the pore volume of the support, but some embodiments limit the total solution volume below that needed to form a gel or slurry (about 100–200% pore volume). In some embodiments the volume of the solution is limited to between 1 and 5 times the pore volume of the support, typically between 1.5 and 3. The residual solvent is then removed, typically under vacuum, typically at ambient temperature and over 10–16 hours. But greater or lesser times are possible.

The catalyst precursor may also be supported in the absence of the activator, in which case the activator may be added to the liquid phase of a slurry process. For example, a solution of catalyst precursor may be mixed with support material for a period of up to 10 hours. The resulting catalyst precursor mixture is then filtered from the solution and dried under vacuum, or vacuum or evaporation alone removes the solvent. The total volume of the catalyst precursor solution may be greater than the pore volume of the support, but some embodiments limit the total solution volume below that needed to form a gel or slurry (about 100–200% of the pore volume). In some embodiments the volume of the solution is limited to between 1 and 5 times the pore volume of the support, typically between 1.5 and 3. Additionally, two or more different catalyst precursors may be placed on the same support using any of the support methods disclosed above. Likewise, two or more activators may be placed on the same support.

As is well know in the art, the support material may be pretreated by any number of methods. For example, inorganic oxides may be calcined, and/or chemically treated with dehydroxylating agents such as aluminum alkyls and the like.

Some embodiments select the carrier of invention catalysts to have a surface area of 10–700 m2/g, or pore volume of 0.1–4.0 cc/g, and average particle size from 10–500 microns. But greater or lesser values may also be used.

The transition metal catalyst compounds may generally be deposited on the support at a loading level of 10–100 micromoles of catalyst precursor per gram of solid support; alternately from 20–80 micromoles of catalyst precursor per gram of solid support; or from 40–60 micromoles of catalyst precursor per gram of support. But greater or lesser values may be used. Some embodiments select greater or lesser values, but require that the total amount of solid catalyst precursor does not exceed the support's pore volume.

Additionally, oxidizing agents may be added to the supported or unsupported catalyst as described in WO 01/68725.

In another embodiment the activator is bound to the support prior to combination with the transition metal catalyst compound. For more information on support bound activators, see U.S. Pat. No. 5,643,847, U.S. Pat. No. 5,972,823, EP 0 775 164 B1, WO 00/4059 A1, and WO 95/9578 A1.

Oligomerization or Polymerization Process

The catalyst compositions described above may be used to oligomerize or polymerize any unsaturated monomer, however they are preferably used to oligomerize olefins, typically alpha-olefins. In the instant oligomerization processes, the process temperature is preferably from −100° C. to 300° C., −20° C. to 200° C., or 0° C. to 150° C. Some embodiments select oligomerization pressures (gauge) from 0 kPa–35 MPa or 500 kPa–15 MPa. A preferred feedstock for the oligomerization process is the alpha-olefin, ethylene. But other alpha-olefins, including but not limited to propylene and 1-butene, may also be used alone or combined with ethylene. Preferred alpha-olefins include any $C_2$ to $C_{40}$ alpha-olefin, preferably and $C_2$ to $C_{20}$ alpha-olefin, more preferably any $C_2$ to $C_{12}$ alpha-olefin, more preferably ethylene, propylene, and butene, most preferably ethylene. Dienes may be used in the processes described herein, preferably alpha, omega-dienes are used alone or in combination with mono-alpha olefins.

Preferred oligomerization processes may be run in the presence of various liquids, particularly aprotic organic liquids. Preferably the homogeneous catalyst system, ethylene, alpha-olefins, and product are soluble in these liquids. A supported (heterogeneous) catalyst system may also be used. Suitable liquids for both homo- and heterogeneous catalyst systems, include alkanes, alkenes, cycloalkanes, selected halogenated hydrocarbons, aromatic hydrocarbons, and in some cases, hydrofluorocarbons. Useful solvents specifically include hexane, toluene, cyclohexane, and benzene.

The instant invention may also be used to obtain mixtures of alpha-olefins containing desirable numbers of carbon atoms. Factor K from the Schulz-Flory theory (see for instance B. Elvers, et al., Ed. Ullmann's Encyclopedia of Industrial Chemistry, Vol. A13, VCH Verlagsgesellschaft mbH, Weinheim, 1989, p. 243–247 and 275–276) serves as a measure of these α-olefins' molecular weights. From this theory, $K=n(Cn+2 \text{ olefin})/n(Cn \text{ olefin})$, where n(Cn olefin) is the number of moles of olefin containing n carbon atoms, and n(Cn+2 olefin) is the number of moles of olefin containing n+2 carbon atoms, or in other words the next higher oligomer of Cn olefin. From this can be determined the weight (mass) fractions of the various olefins in the resulting product. The ability to vary this factor provides the ability to choose the then-desired olefins.

Invention-made alpha-olefins may be further polymerized with other olefins to form more oligomers or even form homopolymers and copolymers of the alpha olefins produced. These polymers may be made by a number of known methods, such as Ziegler-Natta-type polymerization, metallocene catalyzed polymerization, and other methods. See for instance WO 96/23010, and Angew. Chem., Int. Ed. Engl., vol. 34, p. 1143–1170 (1995); European Patent Application, 416,815; and U.S. Pat. No. 5,198,401, for information about metallocene-type catalysts, and J. Boor Jr., Ziegler-Natta Catalysts and Polymerizations, Academic Press, New York, 1979 and G. Allen, et al., Ed., Comprehensive Polymer Science, Vol. 4, Pergamon Press, Oxford, 1989, pp. 1–108, 409–412 and 533–584. For information about Ziegler-Natta-type catalysts, see H. Mark, et al., Ed., Encyclopedia of Polymer Science and Engineering, Vol. 6, John Wiley & Sons, New York, 1992, p. 383–522.

Preferred oligomerization processes include oligomerizing ethylene to C4–C26 linear alpha-olefins.

Oligomers produced herein may be used as polyolefin feed stocks. They may be used as a mixture of olefins alone, as a mixture of olefins added to other olefins, or they may be separated into fractions, and then used alone or in combination with other olefins to form polyolefins. Additionally, alpha-olefins produced herein may be converted to alcohols by known processes, these alcohols being useful for a variety of applications such as intermediates for detergents or plasticizers. Typical processes for the conversion of alpha-olefins to alcohols include, but are not limited to, the oxo process followed by hydrogenation, or by a modified, single-step oxo process, see for instance B. Elvers, et al., Ed., Ullmann's Encyclopedia of Chemical Technology, 5th Ed., Vol. A18, VCH Verlagsgesellschaft mbH, Weinheim, 1991, p. 321–327.

EXAMPLES

Preparation of Ligands

The electrospray (ES) mass spectra were recorded using a micromass Quattra LC mass spectrometer with methanol as the matrix [Masslynx software; open-access autosampler injection]. The infrared spectra were recorded as Nujol mulls between 0.5 mm NaCl plates on a Perkin Elmer 1600 series. 1H and 13C NMR spectra were recorded on a Bruker ARX spectrometer 250/300 Hz; chemical shifts (ppm) are referred to the residual protic solvent peaks. The reagents, sodium t-butoxide the aryl bromides were purchased from Aldrich Chemical Co. and used without further purification. rac-BINAP (rac-2,2'-bi(diphenylphosphino)-1,1'-binaphthyl) was purchased from Strem Chemical Co. The compounds, $Pd_2(dba)_3$ (tris(dibenzylideneacetone)dipalladium(0) used as the chloroform solvate) [1], $\{(2-C_5H_4N)CH_2\}_2NH$ (dpa) [2], $(H_2NCH_2CH_2)\{2-C_5H_4N)CH_2\}NH$ [3], 2-Bromo-1,3,5-i-$Pr_3C_6H_2$ [4], and N-tosylaziridine [5] were prepared according to a previously reported procedures referenced below. $Pd_2(dba)_3$ can also be purchased from Strem Chemical Co. All other chemicals were obtained commercially and used without further purification.

[1] T. Ukai, H. Kawazura, Y. Ishii, J. Bonnet and J. A. Ibers, J. Organomet. Chem., 1974, 65, 253; [2] H. J. Hoom, P. de. Joode, W. L. Driessen and J. Reedijk, Recueil des Travaux. Chim. Des. Pays-Bas., 1996, 115, 191; [3] Y. Maeda, K. Kawano and T. Oniki, J. Chem. Soc., Dalton Trans., 1995, 3533; [4] G. M. Whitesides, M. Eisenhut and W. M. Bunting, J. Amer. Chem. Soc., 1974, 96, 5398; [5] B. Dietrich, M. W. Hossein, J.-M. Lehn and R. B. Sessions, Helv. Chim. Acta, 1985, 68, 289.

Examples 1–3, 5–7

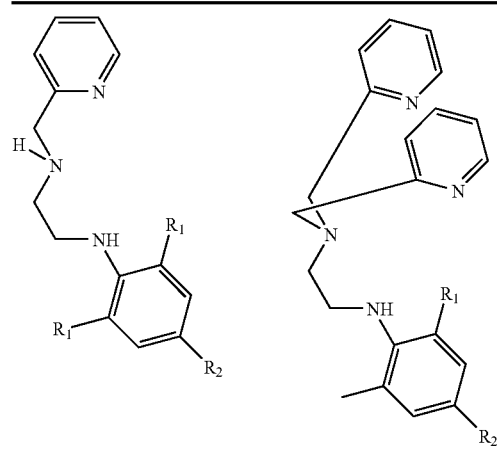

Example 1 (1a) $R_1$ = Me, $R_2$ = H    Example 5 (2a) $R_1$ = Me, $R_2$ = H
Example 2 (1b) $R_1$ = $R_2$ = Me       Example 6 (2b) $R_1$ = $R_2$ = Me
Example 3 (1c) $R_1$ = $R_2$ = i-Pr     Example 7 (2c) $R_1$ = H, $R_2$ = Me

Example 1

Preparation of (N-2,6-dimethylphenyl-2-aminoethyl)(2-picolyl)amine (1a)

A Schlenk tube was charged with $(H_2NCH_2CH_2\{2-C_5H_4N)CH_2\}NH$ (1.00 g, 6.62 mmol), 2-bromo-m-xylene (0.88 cm3, 1.23 g, 6.62 mmol), $Pd_2(dba)_3$ (0.030 g, 0.033 mmol, 0.005 equiv.), rac-BINAP (0.062 g, 0.099 mmol, 0.015 equiv.), NaOBut (1.91 g, 19.9 mmol, 3 equiv.) and toluene (40 cm3). The reaction mixture was heated to 100° C. and stirred for a period of 4 days. After cooling to room temperature, the solvent was removed under reduced pressure to afford an oily residue. The residue was dissolved in diethyl ether (30 cm3) and washed with water (3×30 cm3) and saturated sodium chloride solution (3×30 cm3). The organic layer was separated and dried over magnesium sulfate. The volatiles were removed under reduced pressure and the residue left under vacuum at 70° C. 24 h to give 1.33 g (79%) of 1a as a viscous oil.

Compound 1a: ES mass spectrum, m/z 256 [M+H]+. IR (nujol mull, cm−1), ν 3350 (N—H, medium). 1H NMR (CDCl$_{13}$, 250 MHz, ppm), δ 2.20 (s, 6H, Meo), 2.77 (t, 2H, 3JH-H 5.7 Hz, $CH_2$), 3.02 (t, 2H, 3JH-H 5.7 Hz, $CH_2$), 3.85 (s, 2H, Py-$CH_2$), 6.70 (m, 1H, Ar—CH), 6.88 (m, 2H, Ar—CH), 7.06 (m, 1H, Py-CH), 7.20 (d, 1H, 3JH-H 7.8 Hz, Py-CH), 7.52 (dt, 1H, 3JH-H 7.8 Hz, Py-CH), 8.50 (dd, 1H, 3JH-H 4.4 Hz, Py-CH). 13C NMR (CDCl$_3$, 250 MHz, ppm, 1H composite pulse decoupled): δ 19.0 (2C, Meo), 48.4 (1C, $CH_2$), 50.0 (1C, $CH_2$), 55.4 (1C, Py-$CH_2$), 121.9 (1C, Py-CH), 122.4 (1C, Py-CH), 122.6 (1C, Ar—CH), 129.2 (2C, Ar—CH), 129.7 (2C, Ar—C), 136.9 (1C, Py-CH), 146.8 (1C, Ar—C), 149.7 (1C, Py-CH), 160.3 (1C, Py-C).

Example 2

Preparation of (N-2,4,6-trimethylphenyl-2-aminoethyl)(2-picolyl)amine (1b)

Compound 1b: ES mass spectrum, m/z 270 [M+H]+. NMR (CDCl$_3$, 293 K): 1H NMR δ 8.7–7.1 (m, 4H, Py-H), 6.84 (s, 2H, Ar—H), 3.98 (s, 2H, Py-$CH_2$, 2H), 3.09 (t, 2H, $CH_2$), 2.89 (t, 2H, $CH_2$), 2.29 (s, 6H, Meo) and 2.21 (s, 3H, Mep). 13C (1H composite pulse decoupled), δ 159.9 (s, C, Py), 149.4 (s, C, Py), 143.8 (s, C, Ar), 136.5 (s, C, Py), 129.5 (s, C, Ar), 129.1 (s, C, Ar), 122.2 (s, C, Py), 122.1 (s, C, Py), 122.0 (s, C, Ar), 55.1 (s, $CH_2$), 49.7 (s, $CH_2$), 48.4 (s, $CH_2$), 20.6 (s, Mep) and 18.5 (s, Meo).

Example 3

Preparation of (N-2,4,6-triisopropylphenyl-2-aminoethyl)(2-picolyl)amine (1c)

Compound 1c was prepared using a similar route and the same molar quantities of reagents as that outlined for 1a (Example 1) employing 2-bromo-1,3,5triisopropylbenzene (1.87 g, 6.62 mmol) as the aryl bromide. Compound 1c was obtained analytically pure in reasonable yield (1.17 g, 50%) as a red oil.

Compound 1c: ES mass spectrum, m/z 353 [M+H]+.

Example 4

Preparation of bis(2-picolyl)(2-aminoethyl) amine (dpea)

The compound was prepared via a two-step procedure:
(i) To a three-necked round bottom flask equipped with a reflux condenser, dropping funnel and a magnetic stirrer was added {(2-C$_5$H$_4$N)CH$_2$}$_2$NH (19.900 g, 100 mmol) dissolved in acetonitrile (250 cm$^3$). The yellow solution was brought to reflux and N-tosylaziridine in acetonitrile (200 cm$^3$) was added dropwise over 1 h, to give a dark red solution, which was heated to reflux for an additional 5 h. The dark red solution was concentrated on a rotary evaporator and dried under reduced pressure overnight to give 39.204 g (99%) of (TsNHCH$_2$CH$_2$){(2-C$_5$H$_4$N)CH$_2$}$_2$N as a dark red oil.

Compound (TsNHCH$_2$CH$_2$){(2-C$_5$H$_4$N)CH$_2$}$_2$N: ES mass spectrum, m/z 419, [M+Na]$^+$, 397 [M+H]$^{3O}$. $^1$H NMR (CDCl$_3$, 250 MHz, ppm): δ 2.36 (s, 3H, CH$_3$), 2.77 (t, 2H, $^3J_{H-H}$ 5.25 Hz, CH$_2$), 3.03 (q, 2H, $^3J_{H-H}$ 5.25 Hz, CH$_2$), 3.76 (s, 4H, CH$_2$), 7.16 (m, 6H, CH), 7.57 (m, 2H, $^3J_{H-H}$ 6 Hz, CH), 7.71 (d, 2H, $^3J_{H-H}$ 8 Hz, CH), 8.58 (d, 2H, $^3J_{H-H}$ 4.6 Hz, CH).

(ii) To (N-tosyl-2-aminoethyl)bis(2-pyridylmethyl)amine (39.204 g, 99.0 mmol) in a round bottom flask equipped with reflux condenser was added concentrated H$_2$SO$_4$ (300 cm$^3$). The dark red solution was heated at 130° C. After 3 days the reaction mixture was cooled in an ice bath. The dropwise addition of diethyl ether (4000 cm$^3$) and absolute ethanol (3000 cm$^3$) gave a dark brown precipitate. The brown precipitate was filtered and immediately dissolved in saturated NaOH. The organic layer was extracted by washing with chloroform, the resulting red organic phase dried over MgSO$_4$ and concentrated on a rotary evaporator, to give 17.449 g (73%) of (H$_2$NCH$_2$CH$_2$){(2-C$_5$H$_4$N)CH$_2$}$_2$N as a red oil.

Compound (H$_2$NCH$_2$CH$_2$){2-C$_5$H$_4$N)CH$_2$}2N: ES mass spectrum, m/z 243, [M+H]+. IR (CH$_2$Cl$_2$, cm-1): ν 3360 (N—H), 3288 (N—H, C—H). 1H NMR (CDCl$_3$, 250 MHz, ppm): δ 1.65 (s, 2H, NH$_2$), 2.67 (t, 2H, 3JH-H 5.7 Hz, CH$_2$), 2.80 (t, 2H, 3JH-H 5.6 Hz, CH$_2$), 3.85 (s, 4H, Py-CH$_2$), 7.14 (dt, 2H, 3JH-H 7.5, 5 Hz, 4JH—H 1.4 Hz, Py-CH), 7.49 (d, 2H, 3JH-H 7.75 Hz, Py-CH), 7.65 (dt, 2H, 3JH-H 7.5 Hz, 4JH—H 1.6 Hz, Py-CH), 8.53 (d, 2H, 3JH-H 5 Hz, 4JH—H 1.6 Hz, Py-CH). 13C NMR (CDCl$_3$, 300 MHz, ppm, 1H composite pulse decoupled): δ 39.9 (1C, CH$_2$), 57.8 (1C, CH$_2$), 61.1 (2C, Py-CH$_2$), 122.4 (2C, Py-CH), 123.4 (2C, Py-CH), 136.8 (2C, Py-CH), 149.4 (2C, Py-CH), 160.0 (2C, Py-C).

Example 5

Preparation of bis(2-picolyl)(N-2,6-dimethylphenyl-2-aminoethyl)amine (2a)

A Schlenk tube was charged with (H$_2$NCH$_2$CH$_2$){2-C$_5$H$_4$N)CH$_2$}2N (1.60 g, 6.62 mmol), 2-bromo-m-xylene (0.88 cm3, 1.23 g, 6.62 mmol), Pd2(dba)3 (0.030 g, 0.033 mmol, 0.005 equiv.), rac-BINAP (0.062 g, 0.099 mmol, 0.015 equiv.), NaOBut (1.91 g, 19.9 mmol, 3 equiv.) and toluene (40 cm3). The reaction mixture was heated to 100° C. and stirred for a period of 4 days. After cooling to room temperature, the solvent was removed under reduced pressure to afford an oily residue. The residue was dissolved in diethyl ether (30 cm3) and washed with water (3×30 cm3) and saturated sodium chloride solution (3×30 cm3). The organic layer was separated and dried over magnesium sulfate. The volatiles were removed under reduced pressure and the residue left under vacuum at 70° C. for 24 h to give 1.71 g (75%) of 2a as a viscous red oil.

Compound 2a: ES mass spectrum: m/z 369 [M+Na]+, 347 [M+H]+. IR (nujol mull, cm-1): ν 3354 (C—N), 1589 (pyridine C═N, C═C), 1H NMR (CDCl$_3$, 250 MHz, ppm): δ 2.2 (s, 6H, CH$_3$), 2.8 (t, 2H, 3JH-H 6 Hz, CH$_2$), 3.1 (t, 2H, 3JH-H 6 Hz, CH$_2$), 3.8 (s, 4H, CH$_2$), 6.68 (m, 1H, 3JH-H 7.56, 7.12 Hz, CH), 6.87 (t, 1H, 3JH-H 7.37 Hz, CH), 7.07 (m, 2H, 3JH-H 4.8, 6 Hz, CH), 7.42 (d, 2H, 3JH-H 8.1 Hz, C$_4$H), 7.6 (t, 2H, 3JH-H 6, 7.8 Hz, CH), 8.47 (d, 2H, 3JH-H 4.8 Hz, CH). 13C NMR (CDCl$_3$, 250 MHz, ppm): δ 19.2 (2C, CH$_3$), 46.2 (1C, CH$_2$), 55.0 (1C, CH$_2$), 60.8 (2C, CH$_2$), 121.5 (1C, CH), 122.5 (2C, CH), 123.5 (2C, CH), 129.2 (2C, CH), 136.8 (2C, CH), 128.9 (2C, C), 147.0 (1C, C), 149.6 (2C, CH), 159.7 (2C, C).

Example 6

Preparation of bis(2-picolyl)(N-2,4,6-trimethylphenyl-2-aminoethyl)amine (2b)

Compound 2b was prepared using a similar route and the same molar quantities of reagents as that outlined for 2a (Example 5) employing 2-bromomesitylene (1.00 cm3, 1.32 g, 6.62 mmol) as the aryl bromide. Compound 2b was obtained as a red oil in moderate yield (0.99 g, 42%).

Compound 2b: ES mass spectrum: m/z 383 [M+Na]+, 361 [M+H]+. IR (nujol mull, cm-1): ν 3355 (C—N), 1589 (pyridine C═N, C═C). 1H NMR (CDCl$_3$, 250 MHz, ppm): δ 2.12 (s, 9H, CH$_3$), 2.76 (t, 2H, 3JH-H 6 Hz, CH$_2$), 3.02 (t, 2H, 3JH-H 6 Hz, CH$_2$), 3.81 (s, 4H, CH$_2$), 6.69 (s, 2H, CH), 7.06 (t, 2H, 3JH-H 7.5, 5 Hz, CH), 7.42 (d, 2H, 3JH-H 8 Hz, CH), 7.56 (m, 2H, 3JH—H 7.5 Hz, CH), 8.46 (d, 2H, 3JH-H 5 Hz, CH). 13C NMR (CDCl$_3$, 250 MHz, ppm): δ 17.6 (2C, CH$_3$), 19.5 (1C, CH$_3$), 45.1 (1C, CH$_2$), 53.6 (1C, CH$_2$), 59.3 (2C, CH$_2$), 121.0 (2C, CH), 122.1 (2C, CH), 127.9 (2C, C), 128.4 (2C, CH), 129.5 (1C, C), 135.3 (2C, CH), 142.9 (1C, C), 148.1 (2C, CH), 158.3 (2C, C).

Example 7

Preparation of bis(2-picolyl)(N-2,4-dimethylphenyl-2-aminoethyl)amine (2c)

Compound 2c was prepared using a similar route and the same molar quantities of reagents as that outlined for 2a (Example 5) employing 5-bromo-m-xylene (0.88 cm3, 1.23 g, 6.62 mmol) as the aryl bromide. Compound 2c was obtained as a red oil in good yield (1.56 g, 68%).

Compound 2c: ES mass spectrum: m/z 369 [M+Na]+, 347 [M+H]+. IR (nujol mull, cm-1): ν 3350 (C—N), 1588 (pyridine C═N, C═C). 1H NMR (CDCl$_3$, 250 MHz, ppm): δ 2.10 (s, 3H, CH$_3$), 2.13 (s 3H, CH$_3$), 2.83 (t, 2H, 3JH-H 6 Hz, CH$_2$), 3.12 (t, 2H, 3JH-H 6 Hz), 3.79 (s, 4H,) 6.35 (d, 1H, 3JH-H 8.47 Hz, CH), 6.79 (m, 2H, 3JH-H 6 Hz, CH), 7.05 (t, 2H, 3JH-H 7, 6, 5 Hz, CH), 7.37 (d, 2H, 3JH-H 7.8 Hz, CH), 7.53 (t, 2H, 3JH-H 7.5 Hz, CH), 8.45 (d, 2H, 3JH-H 4.8 Hz, CH). 13C NMR (CDCl$_3$, 250 MHz, ppm): δ 17.9 (1C, CH$_3$), 20.73 (1C, CH$_3$), 41.7 (1C), 53.1 (1C, CH$_2$), 60.6 (2C, CH$_2$), 110.3 (1C, CH), 122.5 (2C, CH), 122.5 (2C, C), 123.4 (2C, CH), 126.1 (1C, C), 127.7 (1C, CH), 131.2 (1C, CH), 136.8 (2C, CH), 144.7 (1C, C), 149.6 (2C, CH), 159.8 (2C, C).

Preparation of Complexes

All complexation reactions were carried out under an atmosphere of dry, oxygen-free nitrogen, using standard Schlenk tube techniques or in a nitrogen purged glove box. n-Butanol was dried and deoxygenated by distillation over sodium metal under nitrogen. The metal dichlorides were purchased from Aldrich Chemical Co. and used without any further purification. FAB mass spectra were recorded using a Kratos Concept spectrometer with NBA (nitrobenzyl alcohol) as the matrix [samples placed on the end of probe within matrix and bombarded with xenon atoms at ca. 7 kV; Mach3 software, probe temperature 50° C.]. Elemental analyses were performed by S. Boyer at the Department of Chemistry, University of North London (UK). Data for the crystal structure determinations were collected on a Bruker APEX 2000 CCD diffractometer and solved using SHELXTL version 6.10. Magnetic susceptibility studies were performed using an Evans Balance at ambient temperature.

Examples 8–20 stirred overnight, filtered, washed with hexane (2×30 cm3) and dried under reduced pressure to afford 0.121 g (80%) of 3a as a pale green solid.

Complex 3a: FAB mass spectrum: m/z 385 [M]+, 350 [M−Cl]+ $\mu_{eff}$ (Evans Balance) 3.8 BM. $Cl_6H_{21}N_3CoCl_2$: calcd. C, 49.89; H, 5.49; N, 10.91. found C, 50.01; H, 5.61; N, 10.80%.

Layering of an acetonitrile solution of 3a with hexane gave blue crystals suitable for a single crystal X-ray diffraction study (FIG. 1).

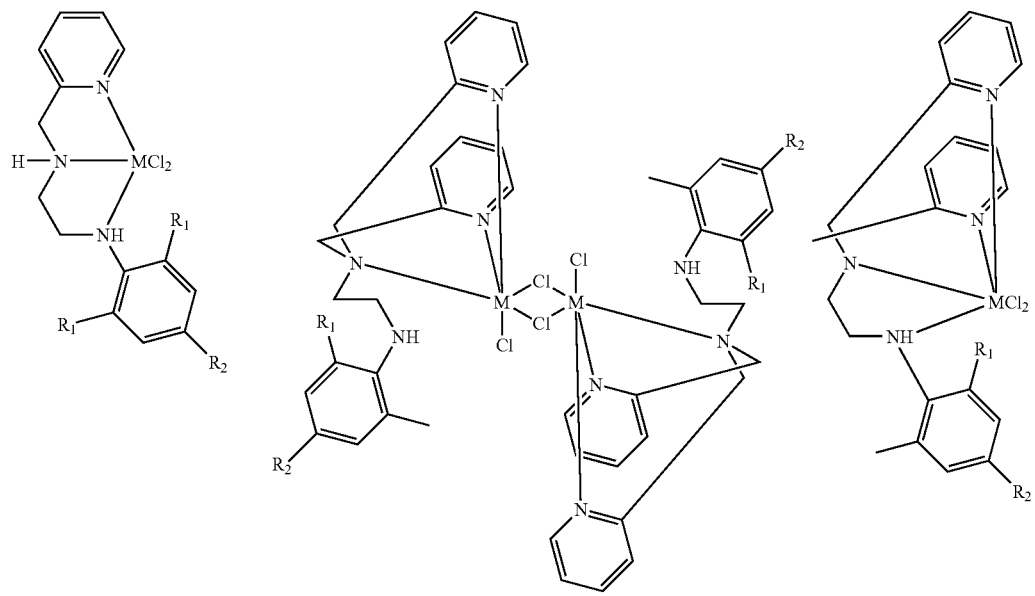

Example 8:
(3a) $R_1$ = Me, $R_2$ = H, M = Co
Example 9:
(3b) $R_1$ = $R_2$ = Me, M = Co
Example 10:
(3c) $R_1$ = $R_2$ = i-Pr, M = Co
Example 11:
(4a) $R_1$ = Me, $R_2$ = H, M = Fe
Example 12:
(4b) $R_1$ = $R_2$ = Me, M = Fe
Example 13:
(4c) $R_1$ = $R_2$ = i-Pr, M = Fe Example 14:
(5a) $R_1$ = Me, $R_2$ = H, M = Co
Example 15:
(5b) $R_1$ = $R_2$ = Me, M = Co
Example 17:
(6a) $R_1$ = Me, $R_2$ = H, M = Fe
Example 18:
(6b) $R_1$ = $R_2$ = Me, M = Fe
ExampLe 20:
(7a) $R_1$ = Me, $R_2$ = H, M = Mn Example 16:
(5c) $R_1$ = H, $R_2$ = Me, M = Co
Example 19:
(6c) $R_1$ = H, $R_2$ = Me, M = Fe Example 8

Synthesis of [(N-2,6-dimethylphenyl-2-aminoethyl)(2-picolyl)amine]cobalt dichloride (3a)

A solution of 1a (0.100 g, 0.39 mmol) in n-butanol (5 cm3) was introduced dropwise to a solution of $CoCl_2$ (0.051 g, 0.39 mmol) in n-butanol (5 cm3) at 90° C. to form a green/blue solution. After being stirred at 90° C. for 1 h, the reaction was allowed to cool to room temperature. The reaction mixture was concentrated and hexane added to induce precipitation of the product. The suspension was Example 9

Synthesis of [(N-2,4,6-trimethylphenyl-2-aminoethyl)(2-picolyl)amine]cobalt dichloride (3b)

Using the same procedure and molar quantities of reagents as that outlined for 3a (Example 8) with 1b (0.105 g, 0.39 mmol) as the ligand, complex 3b was obtained as a pale green powder in good yield (0.118 g, 75%).

Complex 3b: FAB mass spectrum: m/z 399 [M]+, 364 [M−Cl]+ $\mu_{eff}$ (Evans Balance) 3.7 BM. $Cl_7H_{23}N_3CoCl_2$. $CH_3CN$ calcd. C, 51.83; H, 5.95; N, 12.73. found C, 51.84; H, 5.97; N, 12.61%.

Figure 2:
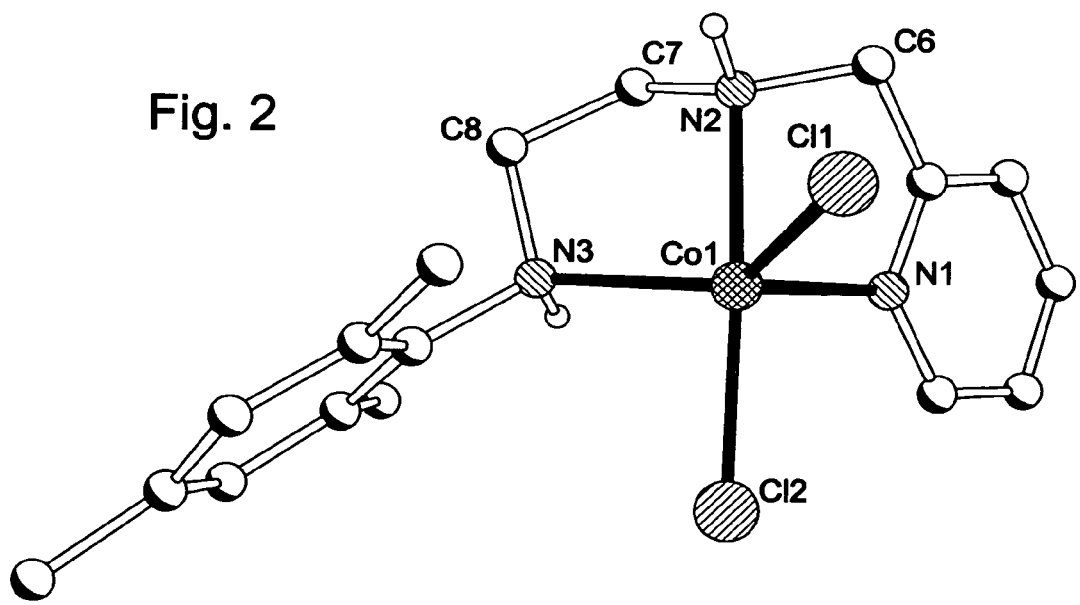
FIG. 2 represents the molecular structure of 3b.

Layering of an acetonitrile solution of 3b with hexane gave blue crystals suitable for a single crystal X-ray diffraction study (FIG. 2).

Example 10

Synthesis of [(N-2,4,6-triisopropylphenyl-2-aminoethyl)(2-picolyl)amine]cobalt dichloride (3c)

Using the same procedure and molar quantities of reagents as that outlined for 3a (Example 8) with 1c (0.137 g, 0.39 mmol) as the ligand, complex 3c was obtained as a pale green powder in good yield (0.140 g, 75%).

Complex 3c: FAB mass spectrum: m/z 483 [M]+, 448 [M−Cl]+.$\mu_{eff}$ (Evans Balance) 3.9 BM.

Example 11

Synthesis of [(N-2,6-dimethylphenyl-2-aminoethyl)(2-picolyl)amine]iron dichloride (4a)

A solution of 1a (0.100 g, 0.39 mmol) in n-butanol (5 cm3) was introduced dropwise to a solution of FeCl2 (0.049 g, 0.39 mmol) in n-butanol (5 cm3) at 90° C. to form a green solution. After being stirred at 90° C. for 1 h, the reaction was allowed to cool to room temperature. The reaction mixture was concentrated and hexane added to induce precipitation of the product. The suspension was stirred overnight, filtered, washed with hexane (2×30 cm3) and dried under reduced pressure to afford 0.115 g (77%) of 4a as a yellow-green solid.

Complex 4a: FAB mass spectrum: m/z 382 [M]+, 347 [M−Cl]+ $\mu_{eff}$ (Evans Balance) 4.9 BM. $Cl_6H_{21}N_3FeCl_2$: calcd. C, 50.29; H, 5.54; N, 11.00. found C, 49.65; H, 5.62; N, 10.62%.

Figure 3:
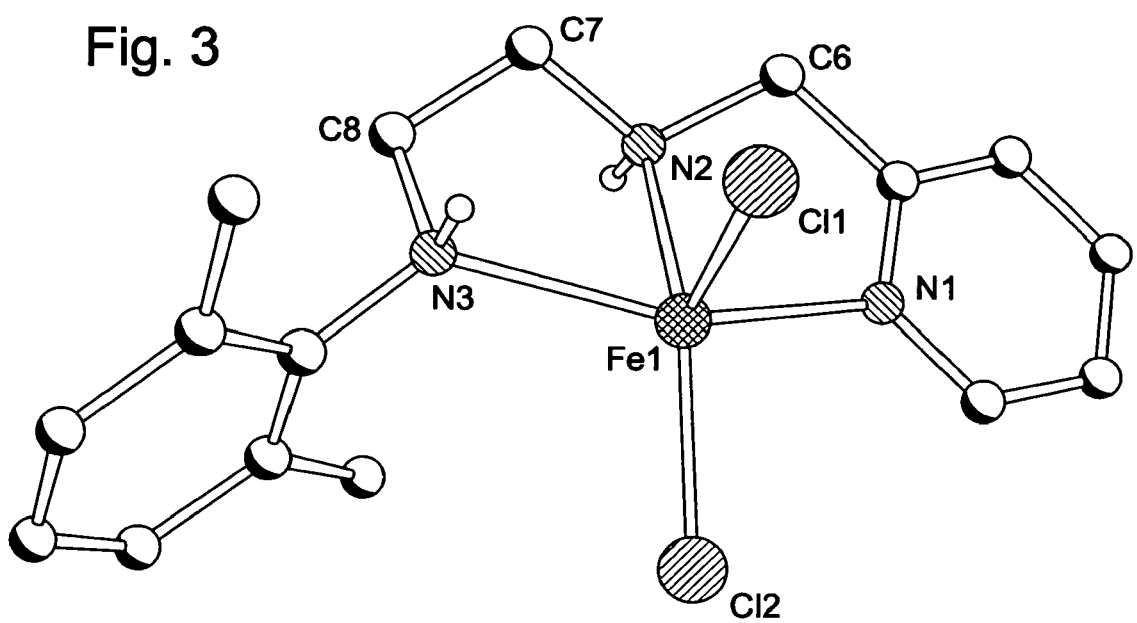

Layering of an acetonitrile solution of 4a with hexane gave yellow crystals suitable for a single crystal X-ray diffraction study (FIG. 3).

Example 12

Synthesis of [(N-2,4,6-trimethylphenyl-2-aminoethyl)(2-picolyl)amine]iron dichloride (4b)

Using the same procedure and molar quantities of reagents as that outlined for 4a (Example 11) with 1b (0.105 g, 0.39 mmol) as the ligand, complex 4b was obtained as a yellow-brown powder in good yield (0.110 g, 71%). Recrystallization of 4b could be achieved by the slow cooling of a hot acetonitrile solution of 4b.

Complex 4b: FAB mass spectrum: m/z 396 [M]+, 361 [M−Cl]+ $\mu_{eff}$ (Evans Balance) 5.0 BM. $C_{17}H_{22}N_3FeCl_2$: calcd. C, 51.68; H, 5.61; N, 10.63. found C, 51.59; H, 5.51; N, 10.63%.

Example 13

Synthesis of [(N-2,4,6-triisopropylphenyl-2-aminoethyl)(2-picolyl)amine]iron dichloride (4c)

Using the same procedure and molar quantities of reagents as that outlined for 4a (Example 11) with 1c (0.137 g, 0.39 mmol) as the ligand, complex 4c was obtained as a yellow-brown powder in good yield (0.102 g, 55%). Recrystallization of 4c could be achieved by the slow cooling of a hot acetonitrile solution of 4c.

Complex 4c: FAB mass spectrum: m/z 480 [M]+, 445 [M−Cl]+.$\mu_{eff}$ (Evans Balance) 5.1 BM.

Example 14

Synthesis of [{bis(2-picolyl) (N-2,6-dimethylphenyl-2-aminoethyl) amine}cobalt dichloride]$_2$ (5a)

A solution of 2a (0.100 g, 0.29 mmol) in n-butanol (5 cm3) was added dropwise to a solution of CoCl$_2$ (0.037 g, 0.32 mmol) in n-butanol (5 cm3) at 90° C. to yield a green solution. After being stirred at 90° C. for 1 h, the reaction was allowed to cool to room temperature. The reaction mixture was concentrated and hexane added to induce precipitation of the product. The suspension was stirred overnight, filtered, washed with hexane (2×30 cm3) and dried under reduced pressure to afford 5a as a pale green solid (0.110 g, 80%).

Complex 5a: FAB mass spectrum: m/z 917 [M−Cl]+, 441 [M/2−Cl]+.□

Example 15

Preparation of [{bis(2-picolyl)(N-2,4,6-trimethylphenyl-2-aminoethyl)amine}cobalt dichloride]$_2$ (5b)

Using the same procedure and molar quantities of reagents as that outlined for 5a (Example 14) with 2b (0.104 g, 0.29 mmol) as the ligand, complex 5b was obtained as a green solid in good yield (0.094 g, 67%).

Complex 5b: FAB mass spectrum: m/z 945 [M−Cl]+, 455 [M/2−Cl]+. $\mu_{eff}$ (Evans Balance) 3.8 BM (per Co center).

Example 16

Preparation of [bis(2-picolyl)(N-2,4-dimethylphenyl-2-aminoethyl)amine]cobalt dichloride (5c)

Using the same procedure and molar quantities of reagents as that outlined for 5a (Example 14) with 2c (0.100 g, 0.29 mmol) as the ligand, complex 5c was obtained as a green solid in good yield (0.102 g, 67%).

Complex 5c: FAB mass spectrum: m/z 475 [M]+, 440 [M−Cl]+. $\mu_{eff}$ (Evans Balance) 4.2 BM.

Example 17

Synthesis of [{bis(2-picolyl)(N-2,6-dimethylphenyl-2-aminoethyl)amine}iron dichloride]$_2$ (6a)

A solution of 2a (0.100 g, 0.29 mmol) in n-butanol (5 cm$^3$) was added dropwise to a solution of FeCl$_2$ (0.037 g, 0.29 mmol) in n-butanol (5 cm$^3$) at 90° C. to yield a green solution. After being stirred at 90° C. for 1 h, the reaction was allowed to cool to room temperature. The reaction mixture was concentrated and hexane added to induce precipitation of the product. The suspension was stirred overnight, filtered, washed with hexane (2×30 cm$^3$) and dried under reduced pressure to afford 6a as a yellow green solid (0.102 g, 75%).

Complex 6a: FAB mass spectrum: m/z 910 [M−Cl]$^+$, 437 [M/2−Cl]$^+$.

Example 18

Preparation of [{bis(2-picolyl)(N-2,4,6-trimethylphenyl-2-aminoethyl)amine}iron dichloride]$_2$ (6b)

Using the same procedure and molar quantities of reagents as that outlined for 6a (Example 17) with 2b (0.104 g, 0.29 mmol) as the ligand, complex 6b was obtained as a yellow green solid in good yield (0.094 g, 67%).

Complex 6b: FAB mass spectrum: m/z 939 [M–Cl]$^+$, 487 [M/2]$^+$, 452 [M/2–Cl]$^+$.

Example 19

Preparation of [bis(2-picolyl)(N-2,4-dimethylphenyl-2-aminoethyl)amine]iron dichloride (6c)

Using the same procedure and molar quantities of reagents as that outlined for 6a (Example 17) with 2c (0.100 g, 0.29 mmol) as the ligand, complex 6c was obtained as a yellow green solid in good yield (0.079 g, 58%).

Complex 6c: FAB mass spectrum: m/z 473 [M]$^+$, 438 [M–Cl]$^+$. $C_{22}H_{26}N_4FeCl_2$. calcd. C, 55.84; H, 5.54; N, 11.84. found C, 55.79; H, 5.59; N, 11.84%.

Figure 4:
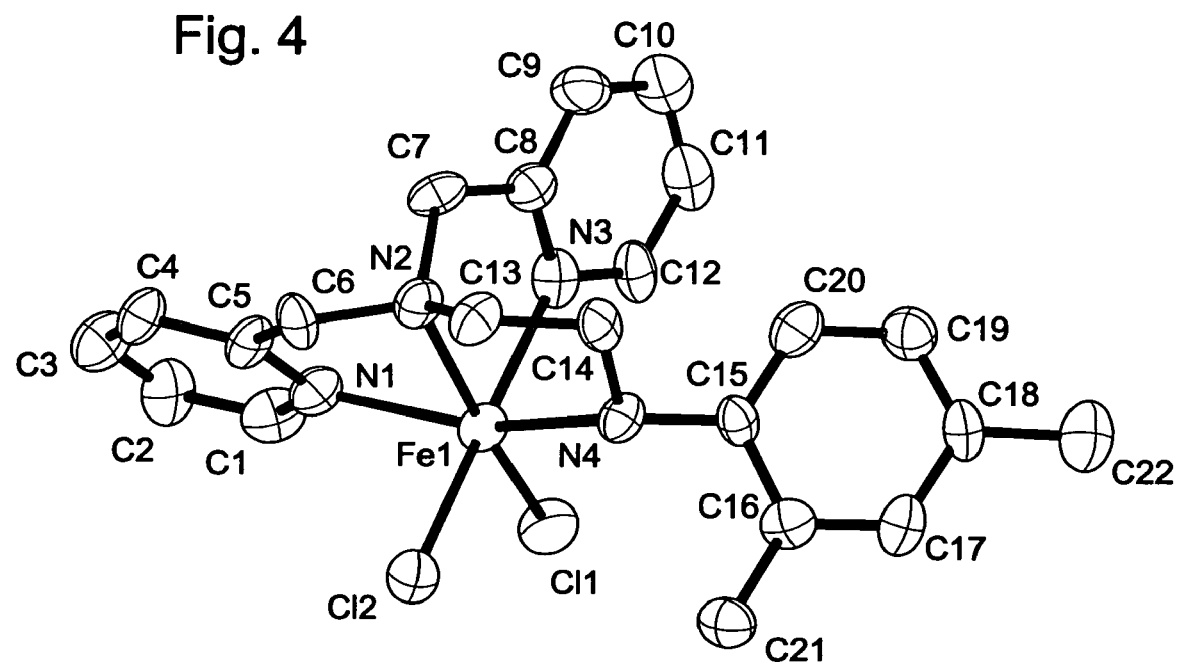
FIG. 4 represents the molecular structure of 6c.

Layering of an acetonitrile solution of 6c with hexane gave yellow crystals suitable for a single X-ray diffraction study (FIG. 4).

Example 20

Preparation of [{bis(2-picolyl)(N-2,6-dimethylphenyl-2aminoethyl)amine}manganese dichloride]$_2$ (7a)

A solution of 2a (0.100 g, 0.29 mmol) in n-butanol (5 cm$^3$) was added dropwise to a solution of MnCl$_2$ (0.049 g, 0.29 mmol) in n-butanol (5 cm$^3$) at 90° C. to yield a green solution. After being stirred at 90° C. for 1 h, the reaction was allowed to cool to room temperature. The reaction mixture was concentrated and hexane added to induce precipitation of the product. The suspension was stirred overnight, filtered, washed with hexane (2×30 cm$^3$) and dried under reduced pressure to afford 7a as a pale pink solid (0.099 g, 70%).

Complex 7a: FAB mass spectrum: m/z 908 [M–Cl]$^+$, 436 [M/2–Cl]$^+$.

Figure 5:
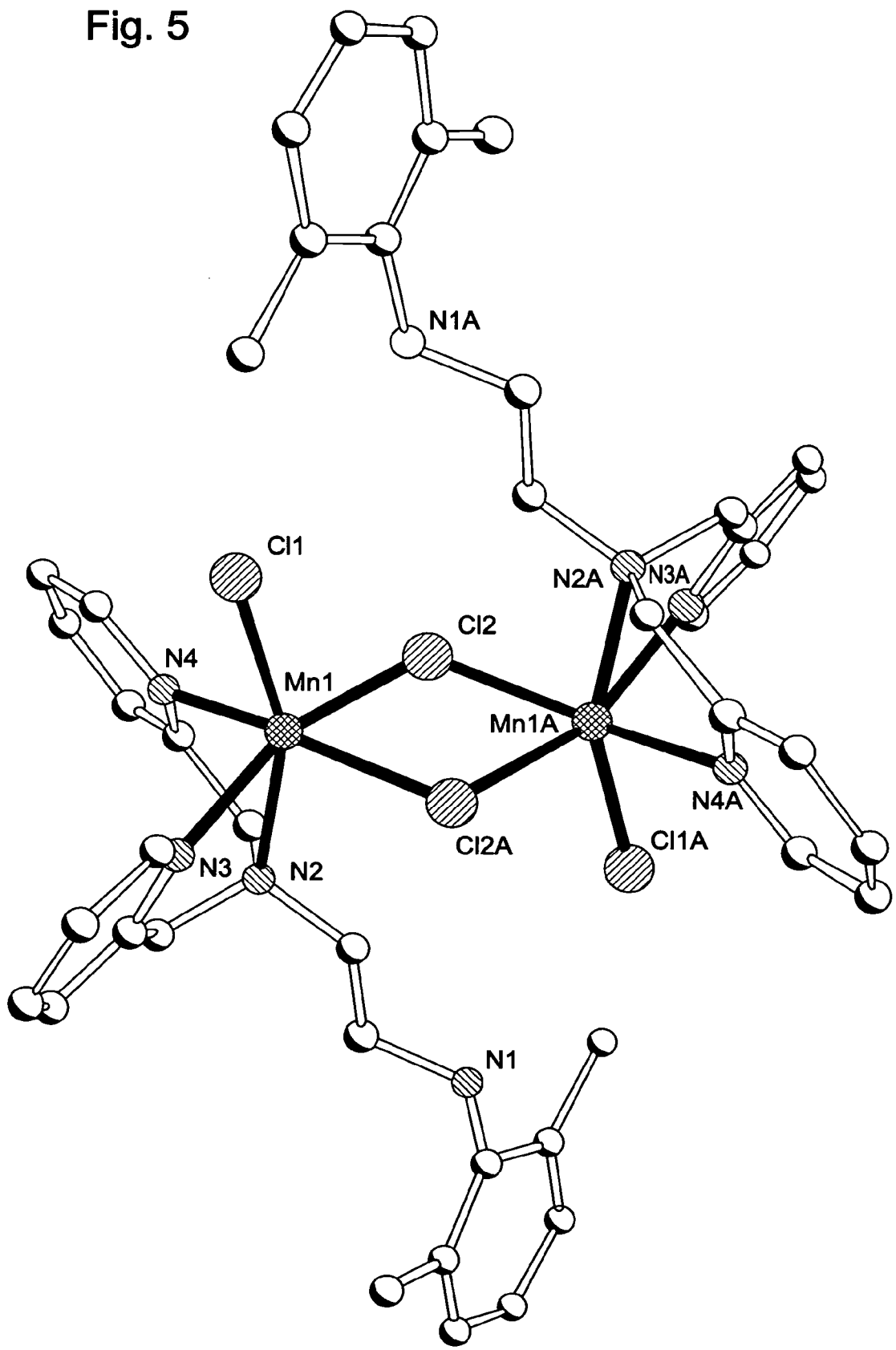

Layering of an acetonitrile solution of 7a with hexane gave clear crystals on prolonged standing (FIG. 5).

Oligomerizations

The reagents used in the oligomerization tests were Ethylene Grade 3.5 (supplied from BOC) and methylalumoxane (MAO, 10% wt solution in toluene, supplied by Aldrich). GC measurements were obtained using either a Perkin Elmer Autosystem XL chromatogram (University of Leicester) [Column type ZB-5; Column length 30 m; Column diameter 0.25 mm; Initial column temperature 50–100° C.] with a Mass Spectrometer detector [Perkin Elmer Tubo; Ionization mode, electron impact; Mass range 50–500 amu; Solvent CH$_2$Cl$_2$] or using an HP 5890 chromatogram (ExxonMobil) [Column type SGE HT-5; Column length 12 m; Column diameter 0.53 mm; Initial column temperature 55° C.] with a flame ionization detector (FID).

Example 21

Schlenk Tube Oligomerization

Figure 6:
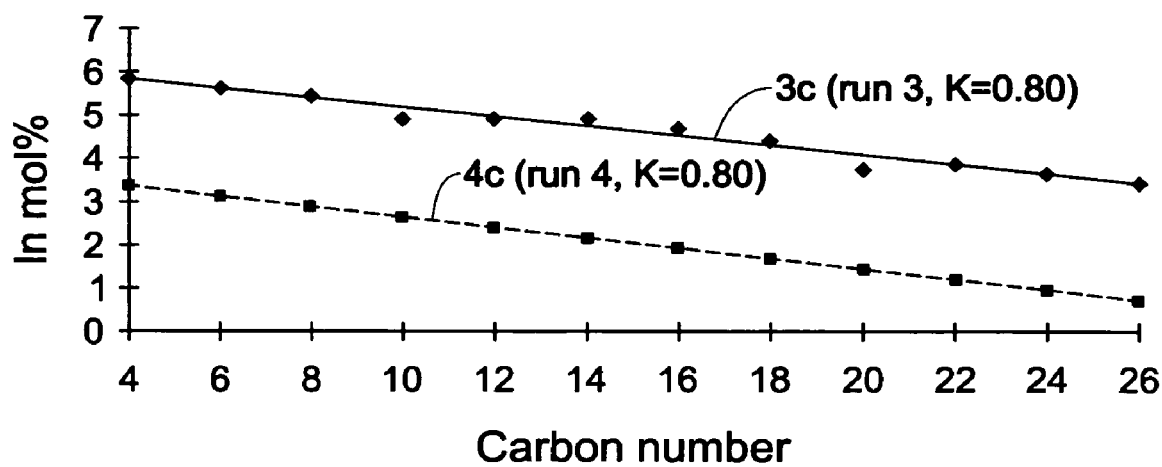
FIG. 6 depicts the Schulz-Flory distribution for runs 3 and 4 using pre-catalysts, 3c and 4c, respectively.
Figure 7:
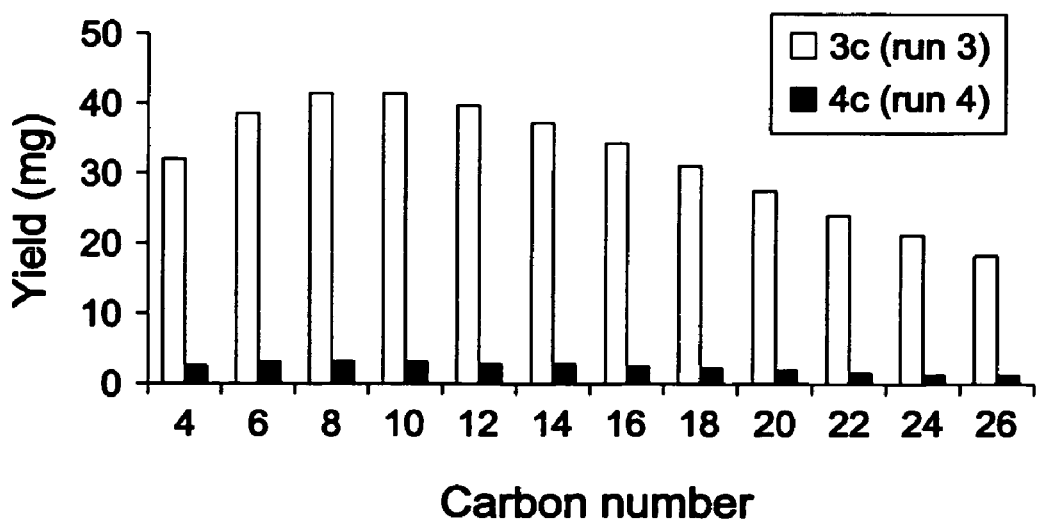
FIG. 7 depicts the oligomer distribution of oligomer fractions versus carbon number for runs 3 and 4 using pre-catalysts 3c and 4c, respectively.

The complexes 3 and 4 made in Examples 8–12 above were dissolved or suspended in toluene (40 cm$^3$) and MAO introduced. The tube was purged with ethylene and the contents stirred under one bar of ethylene pressure at 25° C. for the duration of the oligomerization. After half an hour the oligomerization was terminated by the addition of aqueous HCl. The aqueous phase was separated and washed with toluene (2×25 ml) and all organic layers combined and dried over anhydrous magnesium sulfate. The solutions were prepared for quantitative GC analysis by diluting the organic phases to 100 ml with toluene in a volumetric flask and adding 1-heptadecene (50 μl) as an internal standard. The runs are summarized in Table 2. FIG. 6 shows the Schulz-Flory distribution for runs 3 and 4 using pre-catalysts, 3c and 4c, respectively. FIG. 7 shows the oligomer distribution of oligomer fractions versus carbon number for runs 3 and 4 using pre-catalysts 3c and 4c, respectively.

TABLE 2

Ethylene oligomerization results from precatalysts 3 and 4.[a]

| Run | Precatalyst (mmol) | Activator[b] (mmol/equiv.) | Oligomers (g)[c] | Activity (g/mmol/h/bar) | K (ʀ)[d] | β[e] |
|---|---|---|---|---|---|---|
| 1 | 3a (0.010) | MAO (4/400) | 0.295 | 59 | 0.76 | 0.32 |
| 2 | 3b (0.010) | MAO (4/400) | 0.131 | 26 | 0.76 | 0.32 |
| 3 | 3c (0.010) | MAO (4/400) | 0.381 | 76 | 0.80 | 0.25 |
| 4 | 4c (0.010) | MAO (4/400) | 0.0295 | 6 | 0.80 | 0.25 |
| 5 | 4c (0.010) | MAO (10/1000) | 0.0260 | 5 | 0.74 | 0.35 |

[a]General Conditions: Toluene solvent (40 cm$^3$), 25° C., reaction time 30 min, ethylene pressure 1 bar, reaction quenched with dilute HCl;
[b]MAO = methylalumoxane;
[c]Determined from GC using extrapolated values based on a Schulz-Flory distribution for $C_4$–$C_8$ and $C_{22}$–$C_{26}$ for runs 1–3 and $C_4$–$C_{10}$ for $C_{26}$ for runs 4/5 employing 1-heptadecene as an internal standard.
[d]K = ʀ = n($C_{n+2}$ olefine/n($C_n$ olefin), where n($C_n$ olefin) is the number of moles of olefin containing n carbon atoms, and n($C_{n+2}$ olefin) is the number of moles of olefin containing n + 2 carbon atoms, and is the rate of propagation over the sum of the rate of propagation and the rate of chain transfer.
[e]β = (1 − ʀ)/ʀ and is the rate of chain transfer over the rate of propagation.

All documents described herein are incorporated by reference herein, including any priority documents and testing procedures for all jurisdictions in which such incorporation is permitted. As is apparent from the foregoing general description and the specific embodiments, while forms of the invention have been illustrated and described, various modifications can be made without departing from the spirit and scope of the invention. Accordingly, it is not intended that the invention be limited thereby. Certain features of the present invention are described in terms of a set of numerical upper limits and a set of numerical lower limits. This specification discloses all ranges formed by any combination of these limits. All combinations of these limits are within the scope of the invention unless otherwise indicated.

We claim:

1. A catalyst system comprising an activator and a compound represented by the formula: $LMX_2$ or the formula $(LMX_2)_2$ wherein:
   each M is, independently, a Group 7, 8, 9, 10 or 11 transition metal;
   L is, independently, a tridentate or tetradentate neutrally charged ligand that is bonded to M by at least three nitrogen atoms;
   at least one of the nitrogen atoms is a central non-pyridinal nitrogen atom and is not bonded to its adjacent atoms by a multibond,
   at least two of the nitrogen atoms are terminal nitrogen atoms;
   at least one terminal nitrogen atom is part of a pyridinyl ring;
   at least one other terminal nitrogen atom is substituted with at least one $C_3$–$C_{50}$ hydrocarbyl or halohydrocarbyl;
   the central nitrogen atom is bonded to at least two different carbon atoms; and
   each X is, independently, an anionic monodentate ligand or two X may join together to form a bidentate dianionic ligand.

2. The catalyst precursor of claim 1, wherein the compound is represented by the formula:

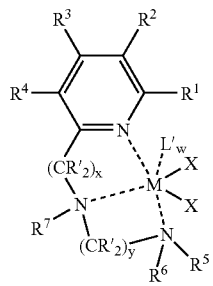

wherein:
   R' is, independently, a hydrogen, a hydrocarbyl, a substituted hydrocarbyl, a halocarbyl, a substituted halocarbyl, a cyclic ring comprising two R' groups on the same carbon, a polycyclic ring comprising two R' groups on the same carbon, a cyclic ring comprising two or more R' groups on adjacent carbons, or a polycyclic ring comprising two or more R' groups on adjacent carbons;
   x is 1, 2, 3, or 4;
   y is 1, 2, 3, or 4,
   $R^1$, $R^2$, $R^3$ and $R^4$ are, independently, a hydrogen, a hydrocarbyl, a substituted a hydrocarbyl, a halocarbyl, a substituted halocarbyl, a cyclic ring structure comprising two adjacent $R^1$, $R^2$, $R^3$ or $R^4$, or a polycyclic ring structure comprising two adjacent $R^1$, $R^2$, $R^3$ or $R^4$;
   $R^5$ is a hydrogen, a hydrocarbyl or a halocarbyl;
   $R^6$ is a $C_3$ to $C_{50}$ hydrocarbyl or a $C_3$ to $C_{50}$ halocarbyl;
   $R^7$ is a hydrogen, a hydrocarbyl, a substituted hydrocarbyl, a halocarbyl, a substituted halocarbyl; a substituted hydrocarbyl comprising a heteroatom, wherein the heteroatom is bonded to M, or a substituted halocarbyl comprising a heteroatom, wherein the heteroatom is bonded to M;
   each L' is a neutral ligand bonded to M; and
   w is 0 or 1.

3. The catalyst precursor of claim 1, wherein the compound is represented by the formula:

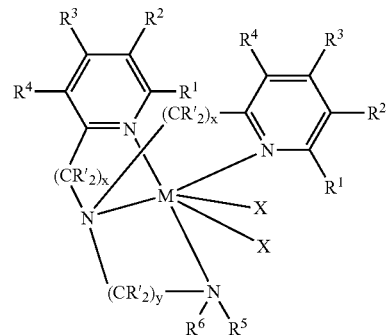

wherein:
   each R' is, independently, a hydrogen, a hydrocarbyl, a substituted hydrocarbyl, a halocarbyl, a substituted halocarbyl, a cyclic ring comprising two R' groups on the same carbon, a polycyclic ring comprising two R' groups on the same carbon, a cyclic ring comprising two or more R' groups on adjacent carbons, or a polycyclic ring comprising two or more R' groups on adjacent carbons;
   x is 1, 2, 3 or 4;
   y is 1, 2, 3 or 4;
   $R^1$, $R^2$, $R^3$ and $R^4$ are, independently, a hydrogen, a hydrocarbyl, a substituted a hydrocarbyl, a halocarbyl, a substituted halocarbyl, a cyclic ring structure comprising two adjacent $R^1$, $R^2$, $R^3$ or $R^4$, or a polycyclic ring structure comprising two adjacent $R^1$, $R^2$, $R^3$ or $R^4$;
   each $R^5$ is a hydrogen, hydrocarbyl or halocarbyl; and
   $R^6$ is a $C_3$ to $C_{50}$ hydrocarbyl or a $C_3$ to $C_{50}$ halocarbyl.

4. The catalyst precursor of claim 1, wherein the compound is represented by the formula:

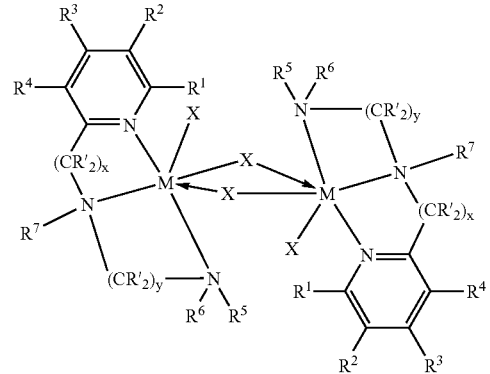

wherein:
   each R' is, independently, a hydrogen, a hydrocarbyl, a substituted hydrocarbyl, a halocarbyl, a substituted halocarbyl, a cyclic ring comprising two R' groups on the same carbon, a polycyclic ring comprising two R' groups on the same carbon, a cyclic ring comprising two or more R' groups on adjacent carbons, or a polycyclic ring comprising two or more R' groups on adjacent carbons;

x is, independently, 1, 2, 3 or 4;

y is, independently, 1, 2, 3 or 4;

each $R^1$, $R^2$, $R^3$ and $R^4$ are, independently, a hydrogen, a hydrocarbyl, a substituted a hydrocarbyl, a halocarbyl, a substituted halocarbyl, a cyclic ring structure comprising two adjacent $R^1$, $R^2$, $R^3$ or $R^4$, or a polycyclic ring structure comprising two adjacent $R^1$, $R^2$, $R^3$ or $R^4$;

each $R^5$ is, independently, a hydrogen, hydrocarbyl or halocarbyl;

$R^6$ is, independently, a $C_3$ to $C_{50}$ hydrocarbyl or a $C_3$ to $C_{50}$ halocarbyl; and each $R^7$ is a hydrogen, a hydrocarbyl, a substituted hydrocarbyl, a halocarbyl, a substituted halocarbyl; a substituted hydrocarbyl comprising a heteroatom, wherein the heteroatom is bonded to M, or a substituted halocarbyl comprising a heteroatom, wherein the heteroatom is bonded to M.

5. The catalyst precursor of claim 1, wherein the compound is represented by the formula:

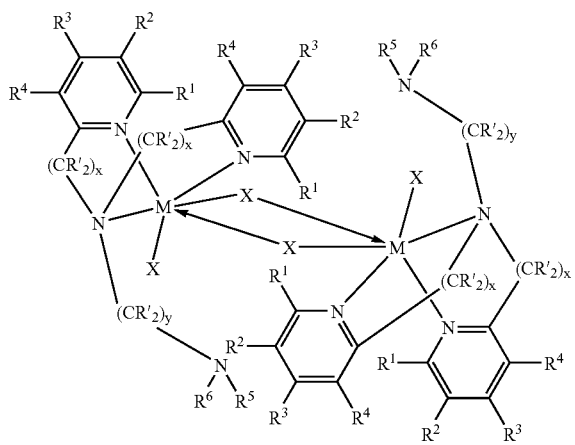

wherein:
each R' is, independently, a hydrogen, a hydrocarbyl, a substituted hydrocarbyl, a halocarbyl, a substituted halocarbyl, a cyclic ring comprising two R' groups on the same carbon, a polycyclic ring comprising two R' groups on the same carbon, a cyclic ring comprising two or more R' groups on adjacent carbons, or a polycyclic ring comprising two or more R' groups on adjacent carbons;

x is 1, 2, 3 or 4;

y is 1, 2, 3 or 4;

each $R^1$, $R^2$, $R^3$ and $R^4$ are, independently, a hydrogen, a hydrocarbyl, a substituted a hydrocarbyl, a halocarbyl, a substituted halocarbyl, a cyclic ring structure comprising two adjacent $R^1$, $R^2$, $R^3$ or $R^4$, or a polycyclic ring structure comprising two adjacent $R^1$, $R^2$, $R^3$ or $R^4$;

each $R^5$ is a hydrogen, hydrocarbyl or halocarbyl; and each $R^6$ is a $C_3$ to $C_{50}$ hydrocarbyl or a $C_3$ to $C_{50}$ halocarbyl.

6. The catalyst precursor of claim 1, wherein the compound is represented by the formula:

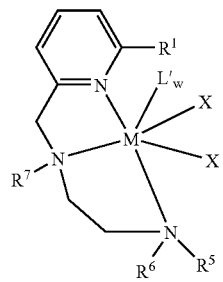

wherein:
$R^1$ is a hydrogen, a hydrocarbyl, a substituted a hydrocarbyl, a halocarbyl, or a substituted halocarbyl;

$R^5$ is a hydrogen, hydrocarbyl or halocarbyl;

$R^6$ is a $C_3$ to $C_{50}$ hydrocarbyl or a $C_3$ to $C_{50}$ halocarbyl;

$R^7$ is a hydrogen, a hydrocarbyl, a substituted hydrocarbyl, a halocarbyl, a substituted halocarbyl; a substituted hydrocarbyl comprising a heteroatom, wherein the heteroatom is bonded to M, or a substituted halocarbyl comprising a heteroatom, wherein the heteroatom is bonded to M;

L' is a neutral ligand bonded to M; and w is 0 or 1.

7. The catalyst precursor of claim 1, wherein the compound is represented by the formula:

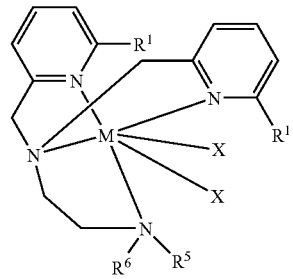

wherein:
each $R^1$ is, independently, a hydrogen, a hydrocarbyl, a substituted a hydrocarbyl, a halocarbyl, or a substituted halocarbyl;

$R^5$ is a hydrogen, hydrocarbyl or halocarbyl; and $R^6$ is a $C_3$ to $C_{50}$ hydrocarbyl or a $C_3$ to $C_{50}$ halocarbyl.

8. The catalyst system of claim 1, wherein the compound is represented by the formula:

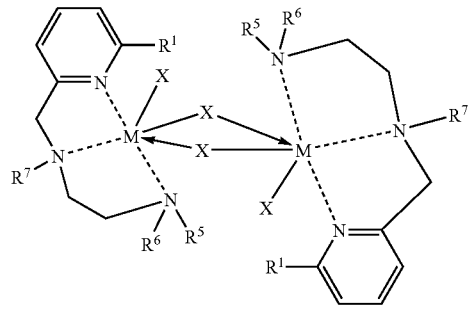

wherein:
each $R^1$ is a hydrogen, a hydrocarbyl, a substituted a hydrocarbyl, a halocarbyl, or a substituted halocarbyl;

each $R^5$ is, independently, a hydrogen, hydrocarbyl or halocarbyl;

each $R^6$ is, independently, a $C_3$ to $C_{50}$ hydrocarbyl or a $C_3$ to $C_{50}$ halocarbyl; and each $R^7$ is a hydrogen, a hydrocarbyl, a substituted hydrocarbyl, a halocarbyl, a substituted halocarbyl; a substituted hydrocarbyl comprising a heteroatom, wherein the heteroatom is bonded to M, or a substituted halocarbyl comprising a heteroatom, wherein the heteroatom is bonded to M.

9. The catalyst precursor of claim 1, wherein the compound is represented by the formula:

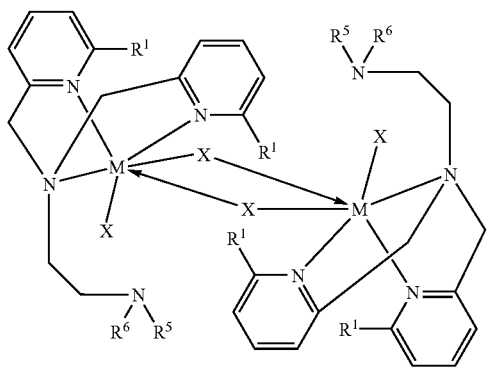

wherein:
each $R^1$ is a hydrogen, a hydrocarbyl, a substituted a hydrocarbyl, a halocarbyl, or a substituted halocarbyl;
each $R^5$ is, independently, a hydrogen, a hydrocarbyl or a halocarbyl;
each $R^6$ is, independently, a $C_3$ to $C_{50}$ hydrocarbyl or a $C_3$ to $C_{50}$ halocarbyl.

10. The catalyst precursor of claim 1, wherein M is a group 7, 8, 9, or 10 transition metal.

11. The catalyst precursor of claim 1, wherein M comprises one or more of nickel, cobalt, iron or manganese.

12. The catalyst precursor of claim 1, wherein X is a hydride, a hydrocarbyl, a substituted hydrocarbyl, a halocarbyl, a substituted halocarbyl, or wherein two X groups together are a hydrocarbdiyl, a halocarbdiyl, a substituted hydrocarbdiyl, or a substituted halocarbdiyl.

13. The catalyst precursor of claim 1, wherein two X groups together are joined, and wherein the two X groups are independently selected from the group consisting of methylidene, ethylidene, propylidene, tetramethylene, pentamethylene, hexamethylene, butadiene, methylbutadiene, dimethylbutadiene, pentadiene, methylpentadiene, dimethylpentadiene, hexadiene, methylhexadiene, and dimethylhexadiene.

14. A catalyst system according to claim 1, wherein the activator comprises an alkyl aluminum compound.

15. A catalyst system according to claim 1, further comprising a support.

16. The catalyst system of claim 15, wherein the support comprises silica.

17. The catalyst system of claim 15, wherein the activator is bound to the support prior to the activator being combined with the catalyst precursor.

18. A process to polymerize an unsaturated monomer comprising contacting the unsaturated monomer with the catalyst system of claim 1.

19. The process of claim 18, wherein the unsaturated monomer comprises ethylene, propylene, a butene, a pentene, a hexene, a heptene, an octene, a nonene, a decene, a dodecene, or a combination thereof.

20. The process of claim 18, wherein the unsaturated monomer further comprises one or more dienes.

21. A process to oligomerize an unsaturated monomer comprising contacting the unsaturated monomer with the catalyst system of claim 1.

22. The process of claim 21, wherein the unsaturated monomer comprises ethylene, propylene, a butene, a pentene, a hexene, a heptene, an octene, a nonene, a decene, a dodecene, or a combination thereof.

23. The process of claim 21, wherein the unsaturated monomer further comprises one or more dienes.

* * * * *

UNITED STATES PATENT AND TRADEMARK OFFICE
CERTIFICATE OF CORRECTION

PATENT NO. : 7,217,675 B2  Page 1 of 1
APPLICATION NO. : 10/802514
DATED : May 15, 2007
INVENTOR(S) : Gregory Adam Solan and Christopher James Davies It is certified that error appears in the above-identified patent and that said Letters Patent is hereby corrected as shown below:

Claim 2, col. 49, line 1, delete "precursor" and substitute therefor -- system --.
Claim 3, col. 50, line 1, delete "precursor" and substitute therefor -- system --.
Claim 4, col. 50, line 1, delete "precursor" and substitute therefor -- system --.
Claim 5, col. 51, line 1, delete "precursor" and substitute therefor -- system --.
Claim 6, col. 52, line 1, delete "precursor" and substitute therefor -- system --.
Claim 7, col. 52, line 1, delete "precursor" and substitute therefor -- system --.
Claim 9, col. 53, line 1, delete "precursor" and substitute therefor -- system --.
Claim 10, col. 53, line 1, delete "precursor" and substitute therefor -- system --.
Claim 11, col. 53, line 1, delete "precursor" and substitute therefor -- system --.
Claim 12, col. 53, line 1, delete "precursor" and substitute therefor -- system --.
Claim 13, col. 54, line 1, delete "precursor" and substitute therefor -- system --.

Signed and Sealed this
First Day of May, 2012

David J. Kappos
*Director of the United States Patent and Trademark Office*

UNITED STATES PATENT AND TRADEMARK OFFICE
CERTIFICATE OF CORRECTION

PATENT NO. : 7,217,675 B2  Page 1 of 1
APPLICATION NO. : 10/802514
DATED : May 15, 2007
INVENTOR(S) : Gregory Adam Solan and Christopher James Davies It is certified that error appears in the above-identified patent and that said Letters Patent is hereby corrected as shown below:

Column 49, line 38 (Claim 2, line 1) delete "precursor" and substitute therefor -- system --.
Column 50, line 11 (Claim 3, line 1) delete "precursor" and substitute therefor -- system --.
Column 50, line 46 (Claim 4, line 1) delete "precursor" and substitute therefor -- system --.
Column 51, line 25 (Claim 5, line 1) delete "precursor" and substitute therefor -- system --.
Column 52, line 1 (Claim 6, line 1) delete "precursor" and substitute therefor -- system --.
Column 52, line 29 (Claim 7, line 1) delete "precursor" and substitute therefor -- system --.
Column 53, line 11 (Claim 9, line 1) delete "precursor" and substitute therefor -- system --.
Column 53, line 37 (Claim 10, line 1) delete "precursor" and substitute therefor -- system --.
Column 53, line 39 (Claim 11, line 1) delete "precursor" and substitute therefor -- system --.
Column 53, line 41 (Claim 12, line 1) delete "precursor" and substitute therefor -- system --.
Column 54, line 4 (Claim 13, line 1) delete "precursor" and substitute therefor -- system --.

This certificate supersedes the Certificate of Correction issued May 1, 2012.

Signed and Sealed this
Twenty-ninth Day of May, 2012

David J. Kappos
*Director of the United States Patent and Trademark Office*